(12) United States Patent
Gallo et al.

(10) Patent No.: US 11,439,659 B2
(45) Date of Patent: Sep. 13, 2022

(54) METHODS AND COMPOSITIONS TO PREVENT AND TREAT INFLAMMATION AND ALLERGIC REACTIONS

(71) Applicant: The Regents of the University of California, Oakland, CA (US)

(72) Inventors: Richard L. Gallo, San Diego, CA (US); Tatsuya Dokoshi, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 290 days.

(21) Appl. No.: 16/702,525

(22) Filed: Dec. 3, 2019

(65) Prior Publication Data

US 2020/0188420 A1    Jun. 18, 2020

Related U.S. Application Data

(60) Provisional application No. 62/774,426, filed on Dec. 3, 2018.

(51) Int. Cl.
| | |
|---|---|
| *A61K 31/702* | (2006.01) |
| *A61K 31/728* | (2006.01) |
| *A61K 31/713* | (2006.01) |
| *A61P 31/04* | (2006.01) |
| *C12N 9/16* | (2006.01) |
| *C12N 9/26* | (2006.01) |
| *A61K 38/47* | (2006.01) |

(52) U.S. Cl.
CPC .......... *A61K 31/713* (2013.01); *A61K 31/702* (2013.01); *A61K 31/728* (2013.01); *A61K 38/47* (2013.01); *A61P 31/04* (2018.01); *C12N 9/16* (2013.01); *C12N 9/2474* (2013.01)

(58) Field of Classification Search
None
See application file for complete search history.

(56) References Cited

U.S. PATENT DOCUMENTS

| | | | | |
|---|---|---|---|---|
| 5,747,027 | A * | 5/1998 | Stern | C12N 9/2408 424/94.62 |
| 6,123,938 | A * | 9/2000 | Stern | C12Y 302/01035 424/94.62 |
| 6,193,963 | B1 * | 2/2001 | Stern | C07K 16/40 424/94.6 |
| 7,105,330 | B2 * | 9/2006 | Stern | C12Y 302/01036 435/200 |
| 7,781,397 | B2 * | 8/2010 | Stern | C12Y 302/01036 424/94.62 |

(Continued)

OTHER PUBLICATIONS

Fronza et al., "Hyaluronidase Modulates Inflammatory Response and Accelerates the Cutaneous Wound Healing" PLoS One vol. 9 issue 11 pp. 1-12 doi:10.1371/journal.pone.0112297 (Year: 2014).*

(Continued)

*Primary Examiner* — Eric Olson
(74) *Attorney, Agent, or Firm* — Gavrilovich, Dodd & Lindsey LLP

(57) ABSTRACT

The disclosure relates to compositions and methods for treating infection, allergic reactions, colitis, IBD, contact dermatitis, psoriasis, atopic dermatitis, graft vs. host disease and disorders and other disease and disorders comprising dendritic cell activation as well as compositions and method to improve allergen sensitization.

16 Claims, 37 Drawing Sheets
Specification includes a Sequence Listing.

(56) References Cited

U.S. PATENT DOCUMENTS

| | | | | |
|---|---|---|---|---|
| 8,298,556 | B2* | 10/2012 | Kolodney | A61K 9/0019 |
| | | | | 424/401 |
| 9,757,468 | B2* | 9/2017 | Esko | A61K 47/67 |
| 9,889,182 | B2* | 2/2018 | Esko | A61K 47/61 |
| 2010/0184854 | A1* | 7/2010 | Du Preez | C07F 15/0093 |
| | | | | 514/492 |
| 2015/0018305 | A1* | 1/2015 | Asari | A61Q 19/00 |
| | | | | 514/54 |

OTHER PUBLICATIONS

Tolg et al., "Specific Sizes of Hyaluronan Oligosaccharides Stimulate Fibroblast Migration and Excisional Wound Repair" PLoS One vol. 9 issue 2 pp. 1-10 doi:10.1371/journal.pone.0088479 (Year: 2014).*

Winkler et al., "Hyaluronan Anchored to Activated CD44 on Central Nervous System Vascular Endothelial Cells Promotes Lymphocyte Extravasation in Experimental Autoimmune Encephalomyelitis" Journal of Biological Chemistry vol. 287 no. 40 pp. 33237-33251 DOI 10.1074/jbc.M112.356287 (Year: 2012).*

Winkler et al. "Hyaluronan oligosaccharides perturb lymphocyte slow rolling on brain vascular endothelial cells: Implications for inflammatory demyelinating disease" Matrix Biology vol. 21 pp. 160-168 http://dx.doi.org/10.1016/j.matbio.2013.01.002 (Year: 2013).*

Vinukonda et al., "Hyaluronidase and Hyaluronan Oligosaccharides Promote Neurological Recovery after Intraventricular Hemorrhage" The Journal of Neuroscience vol. 36 No. 3 pp. 872-889 (Year: 2016).*

* cited by examiner

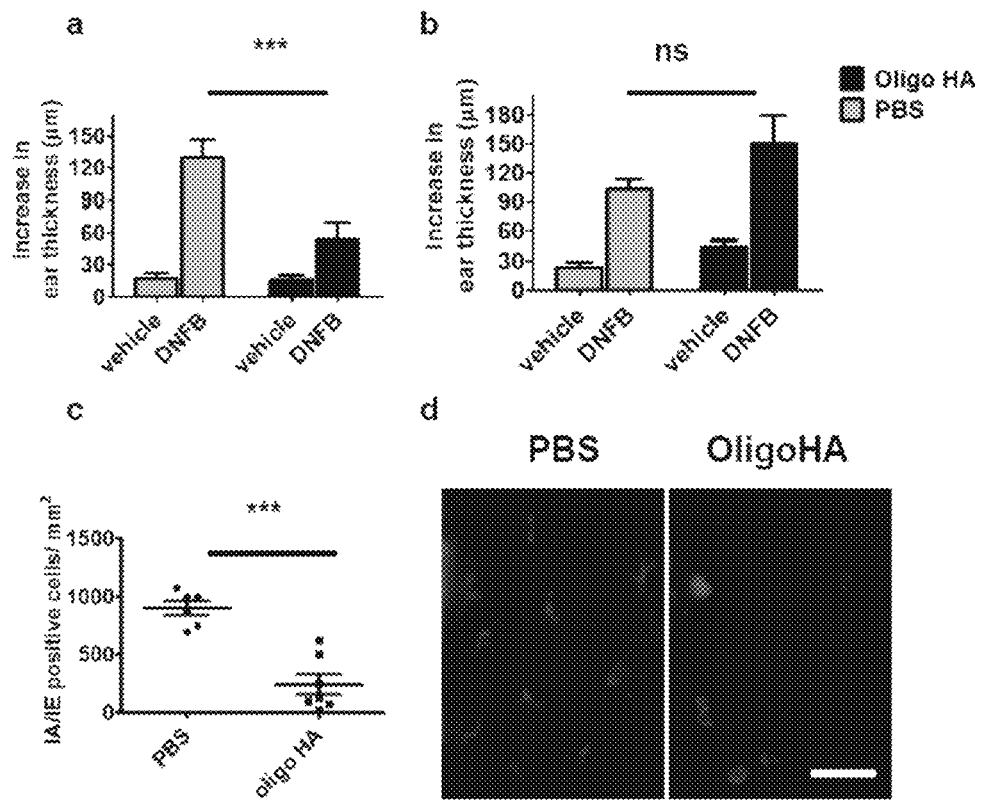
FIGURE 1A-D
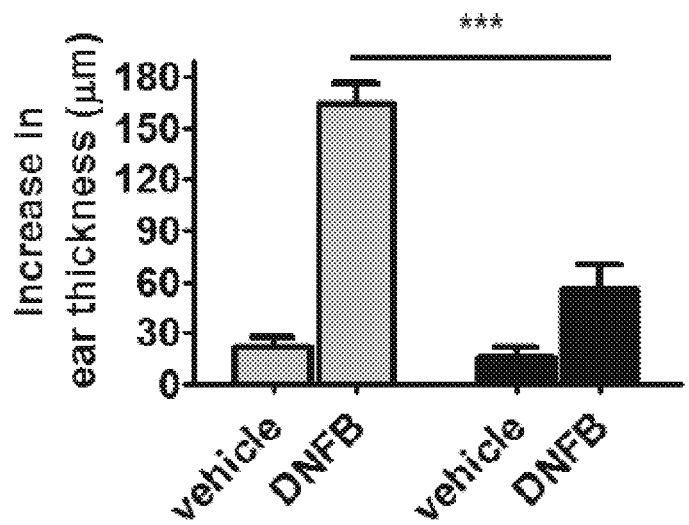
FIGURE 2

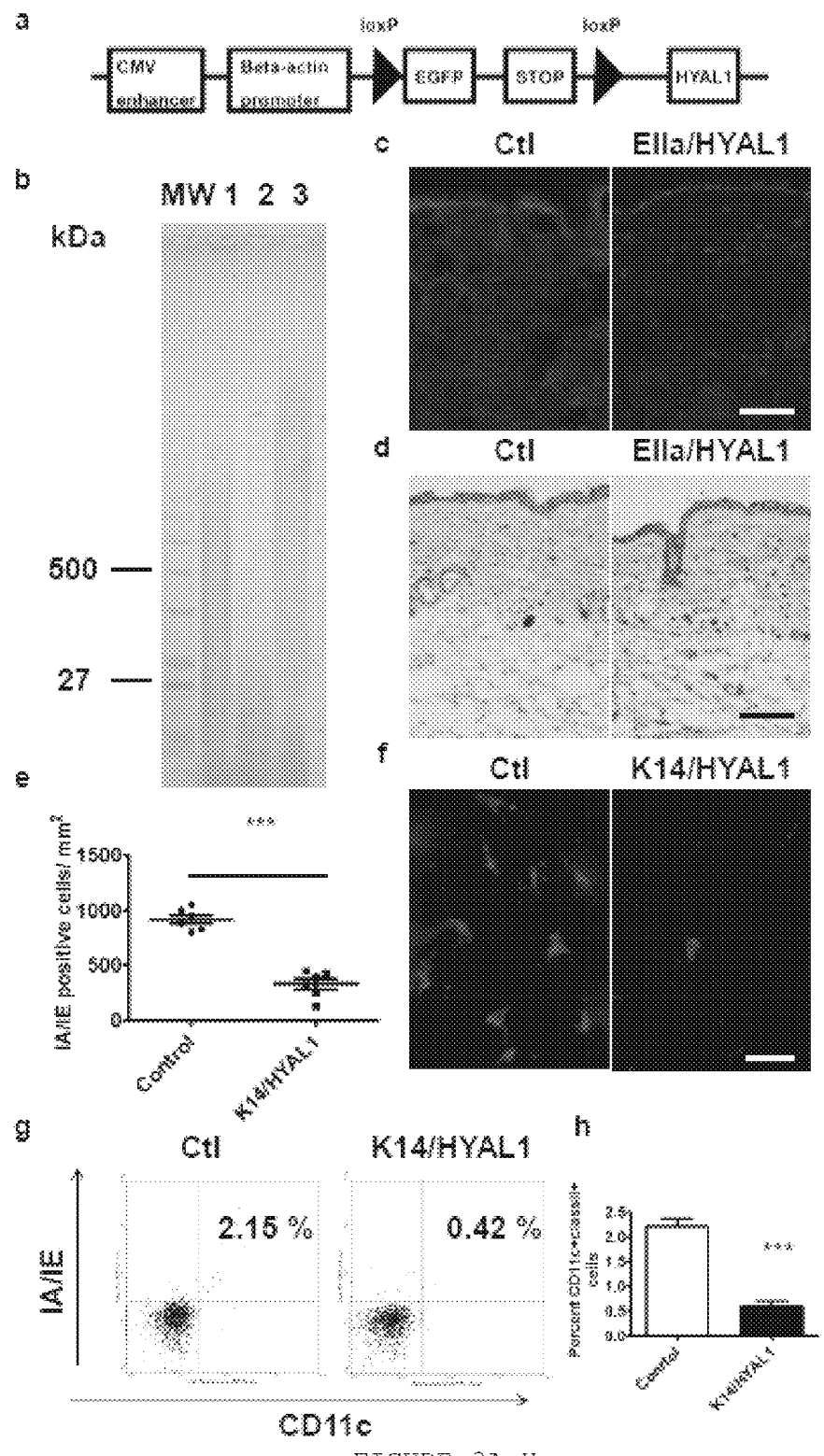
FIGURE 3A-H

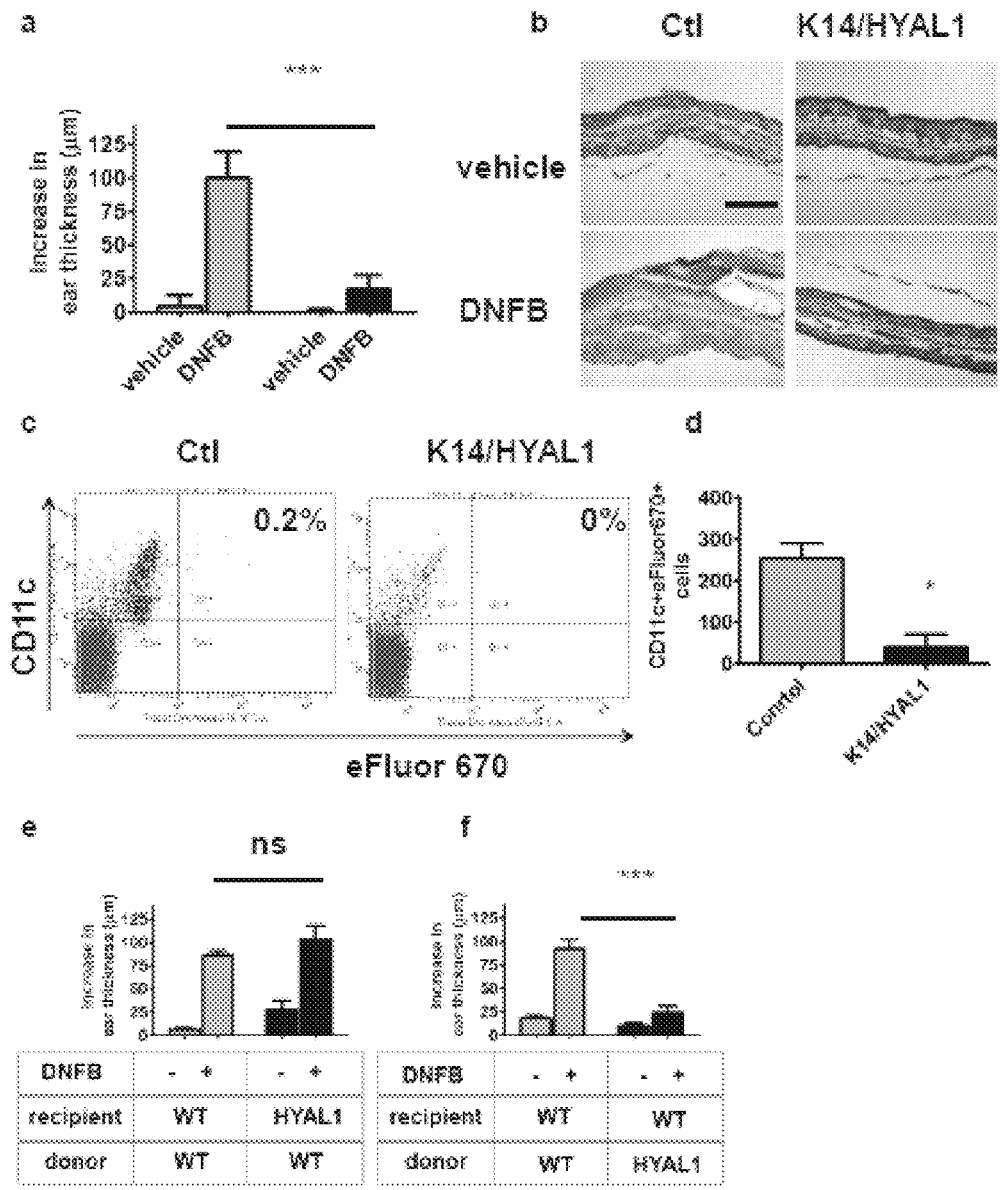
FIGURE 4A-F

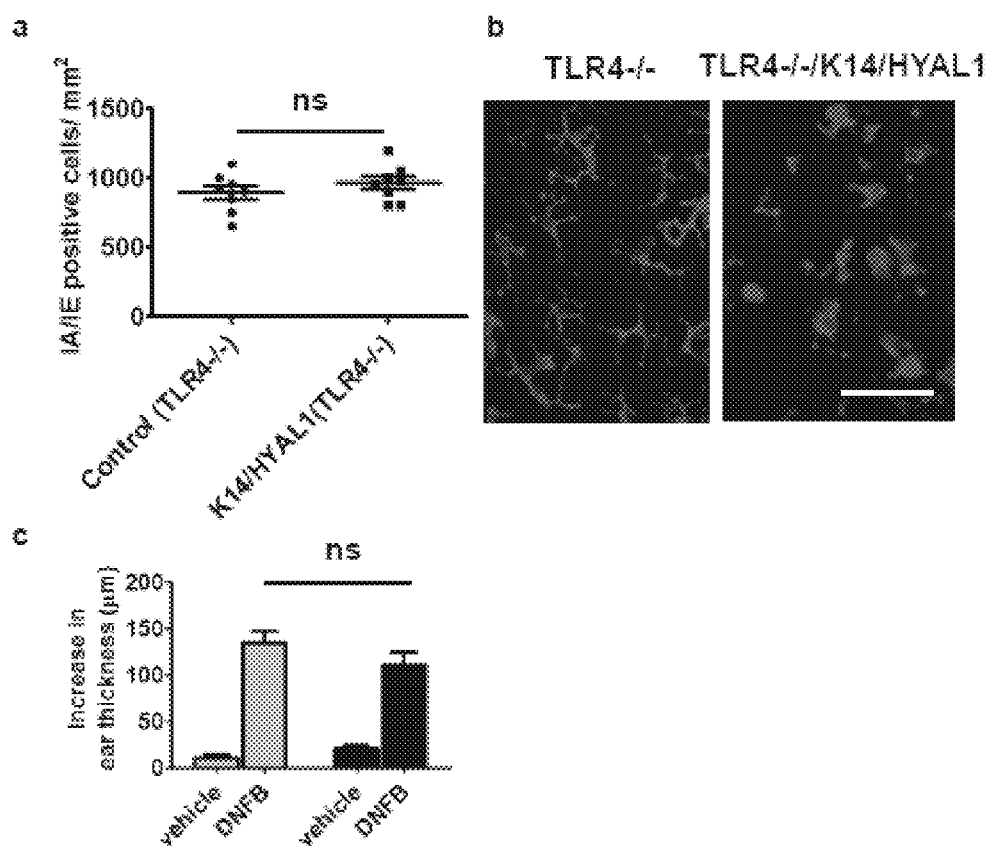
FIGURE 5A-C

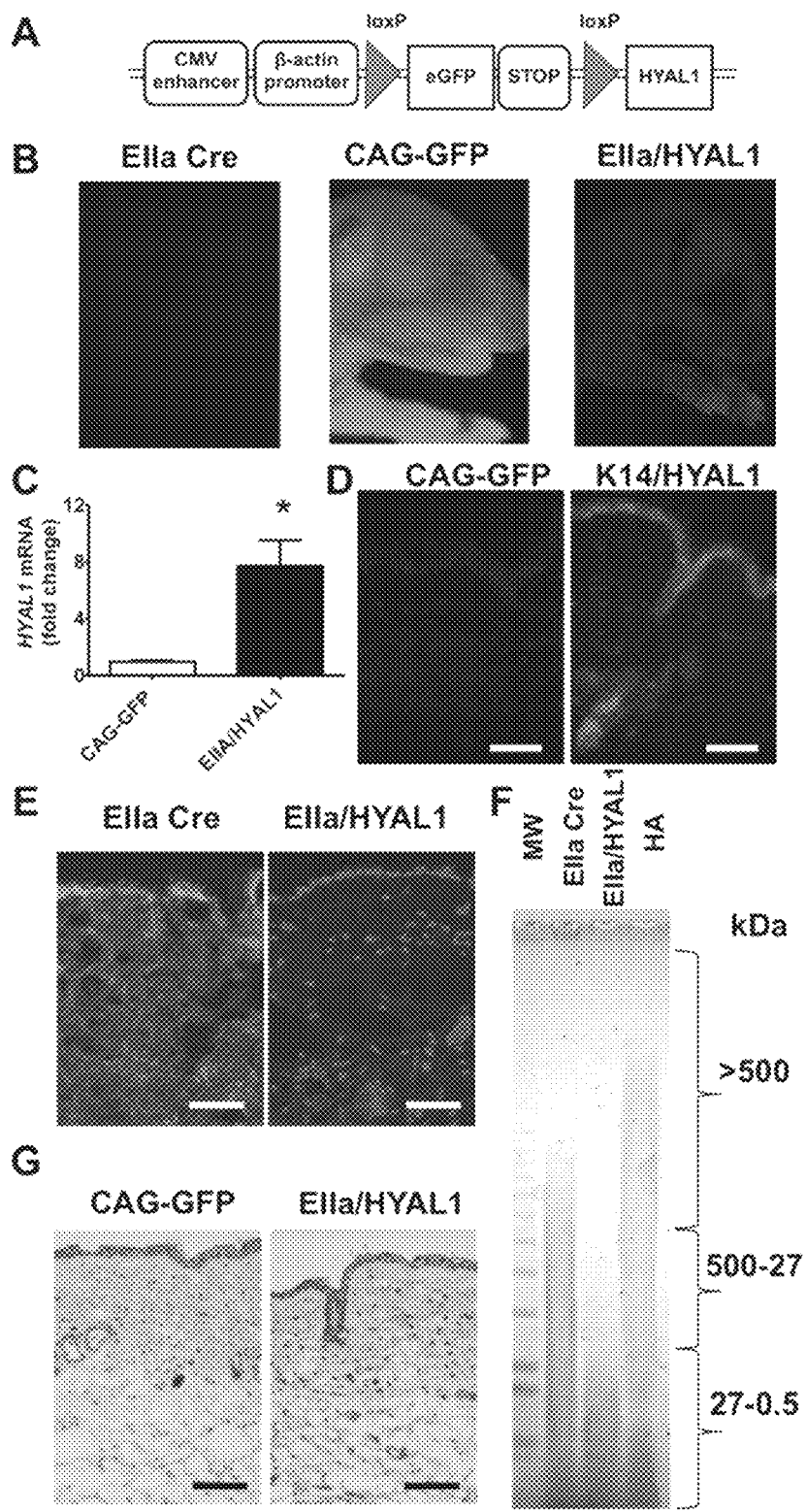
FIGURE 6A-G

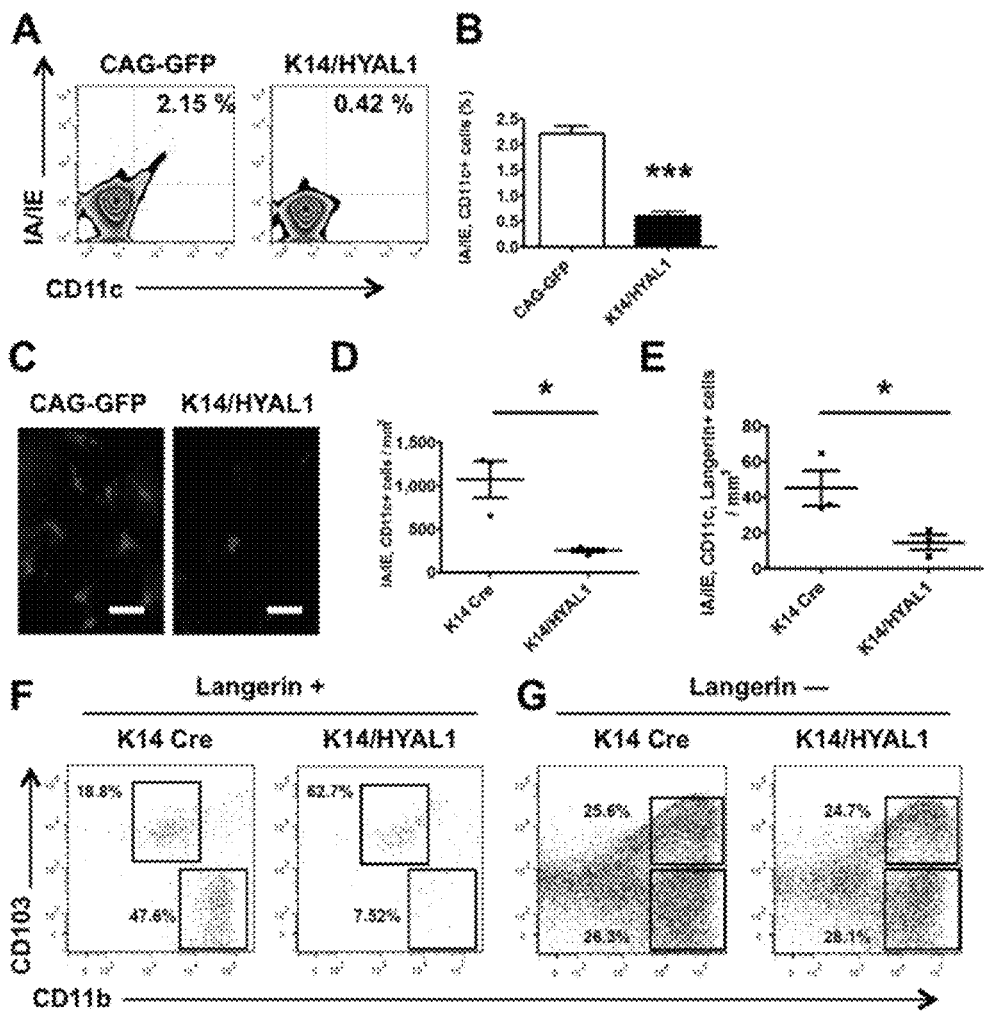
FIGURE 7A-G

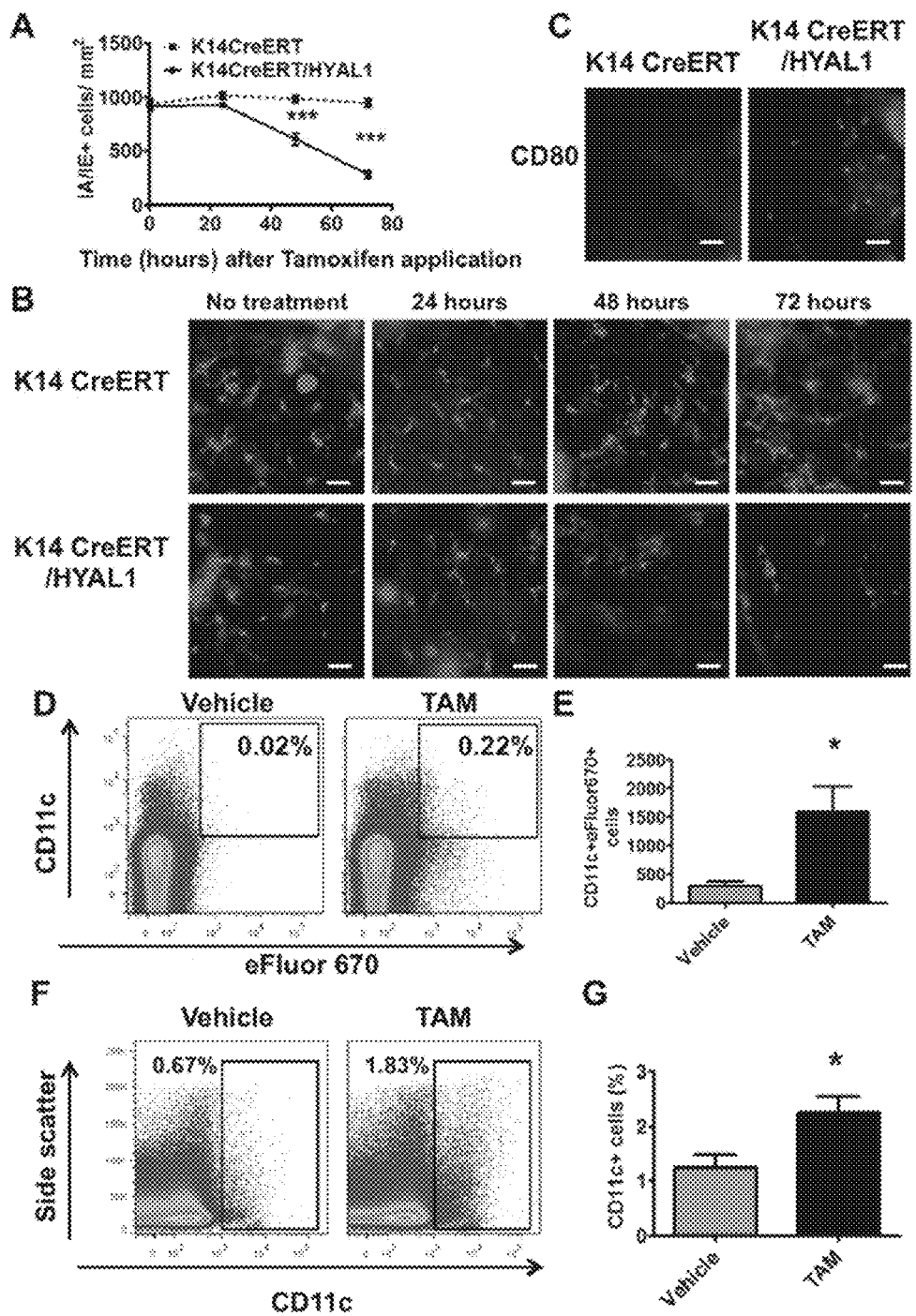
FIGURE 8A-G

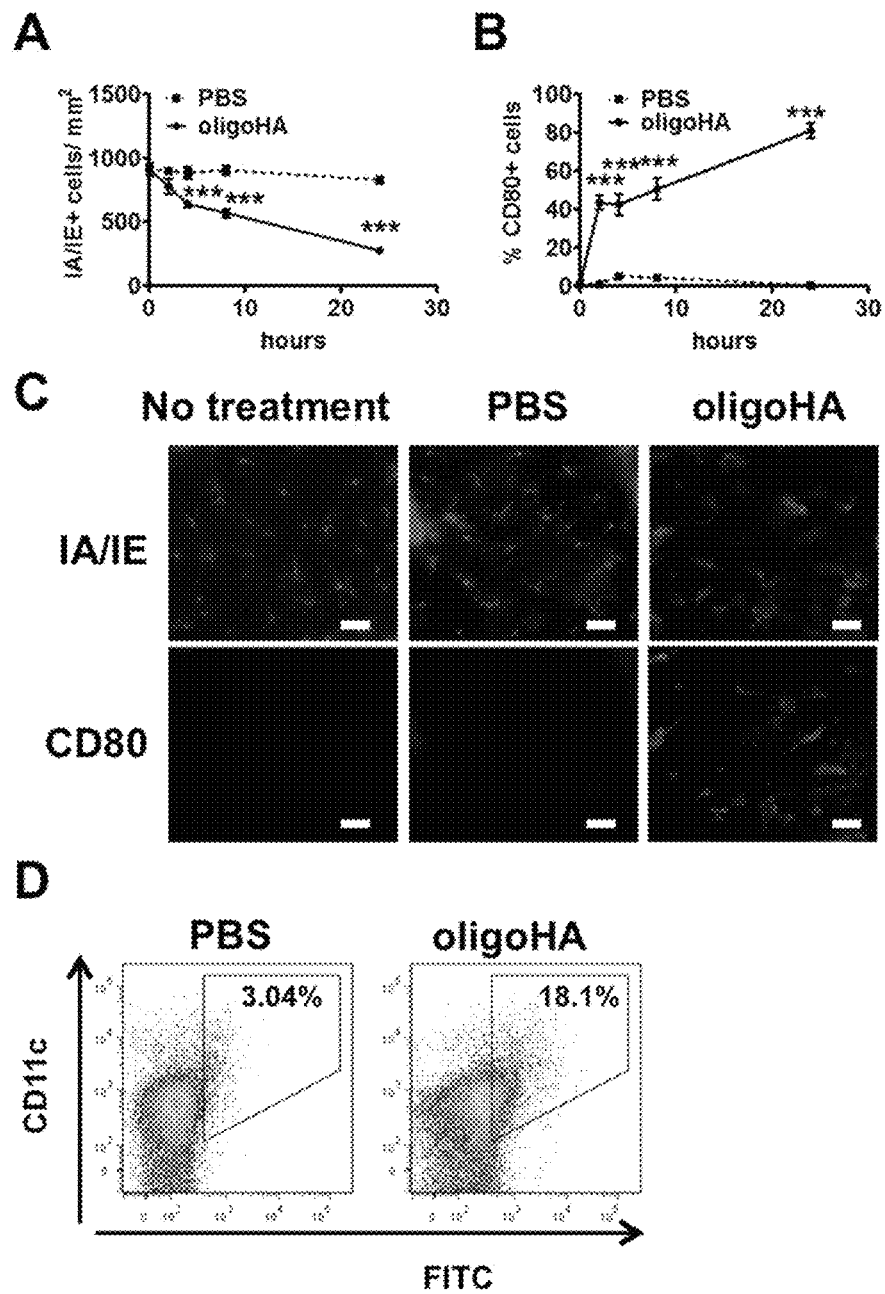
FIGURE 9A-D

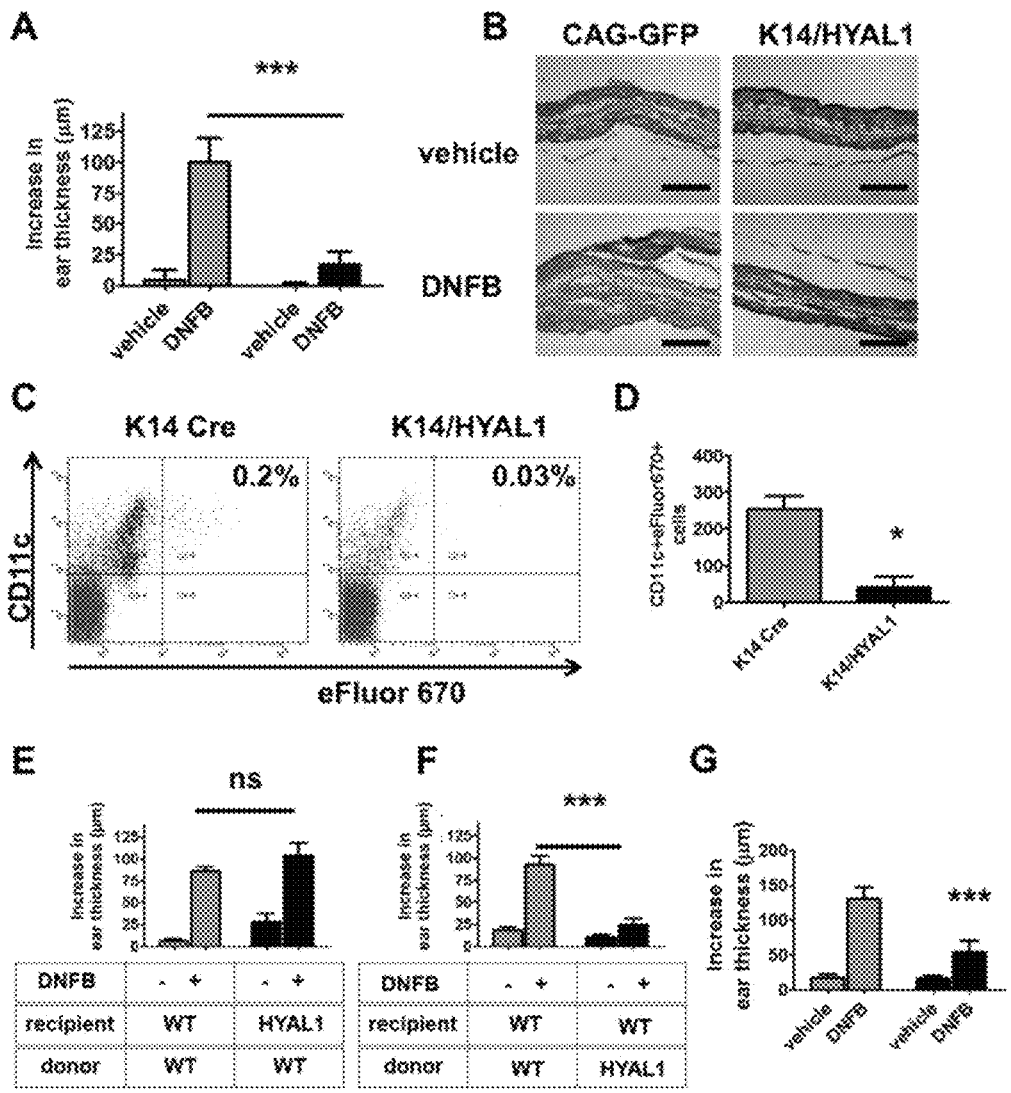
FIGURE 10A-G

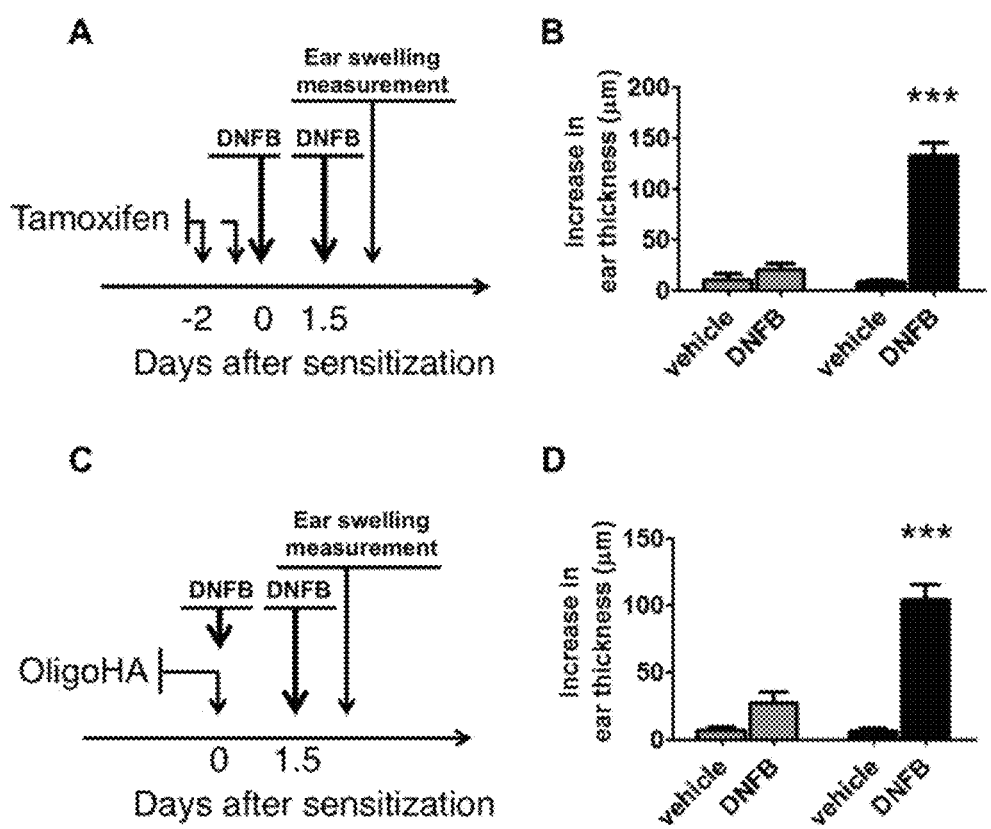
FIGURE 11A-D

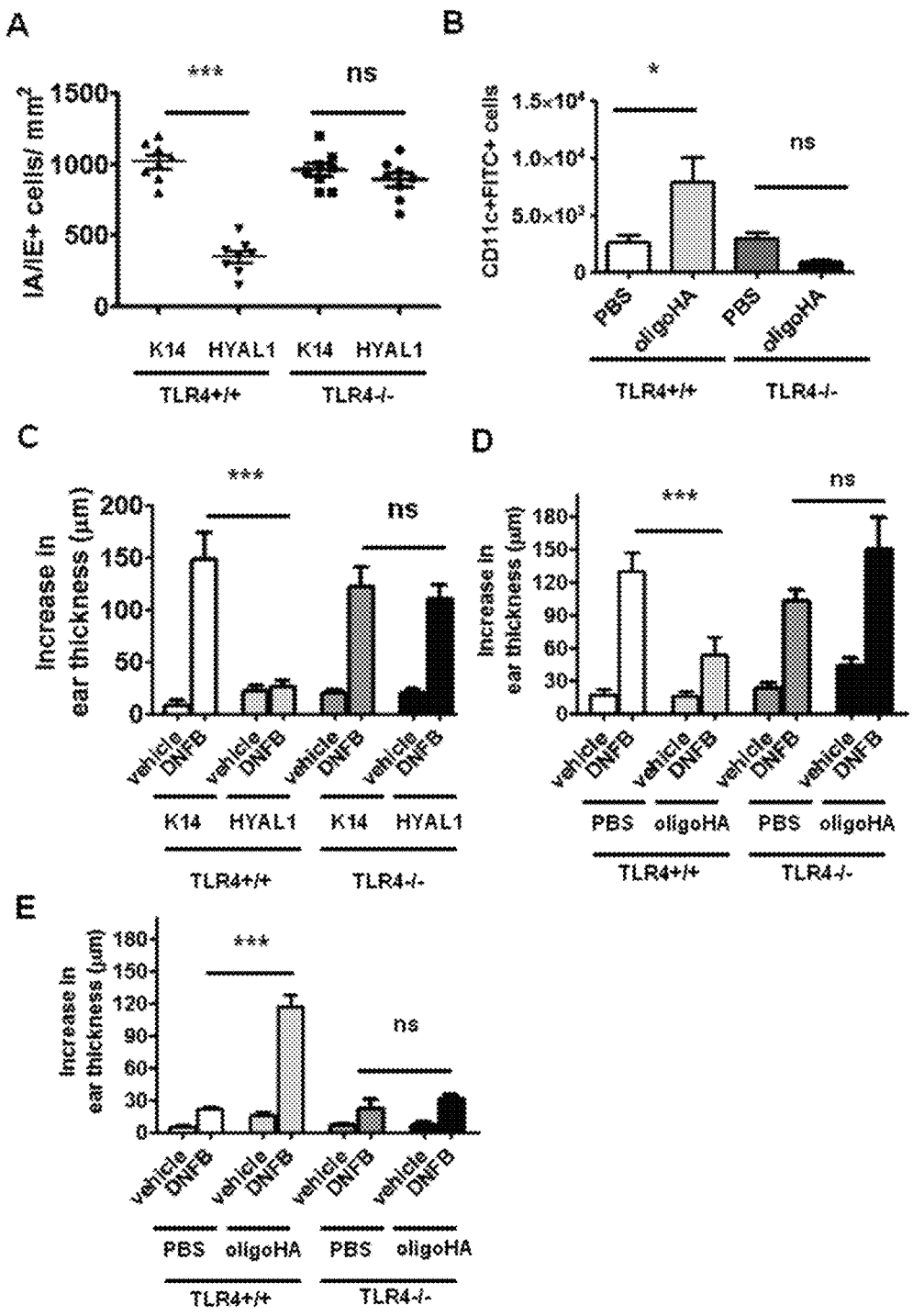
FIGURE 12A-E

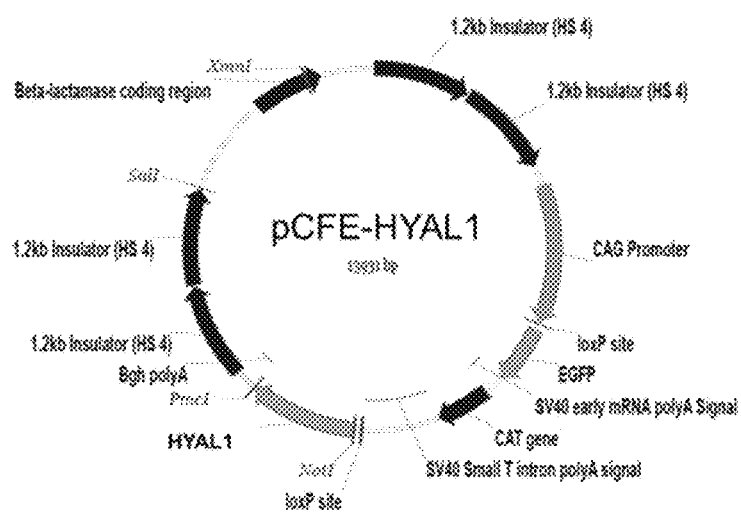
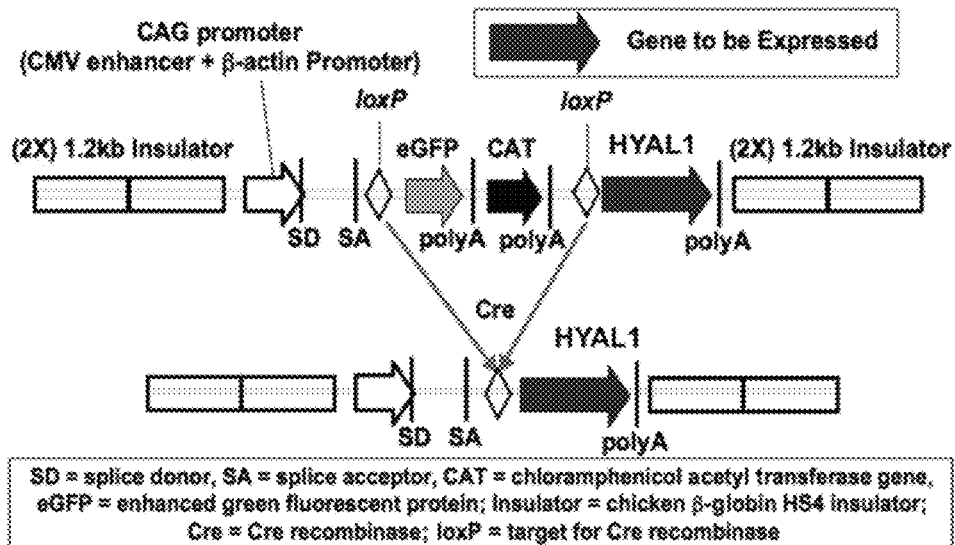
FIGURE 13A-B

FIGURE 16A-B

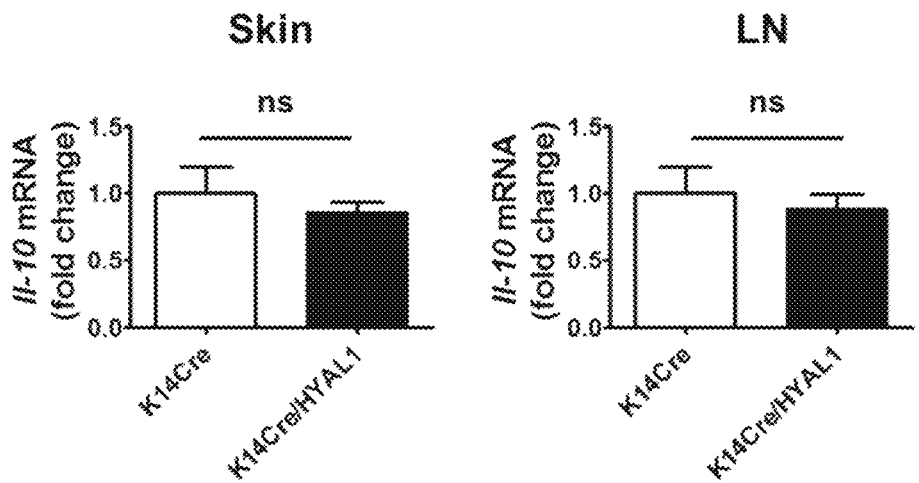
FIGURE 17
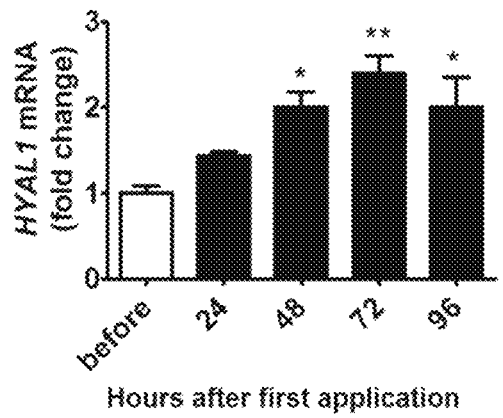
FIGURE 18
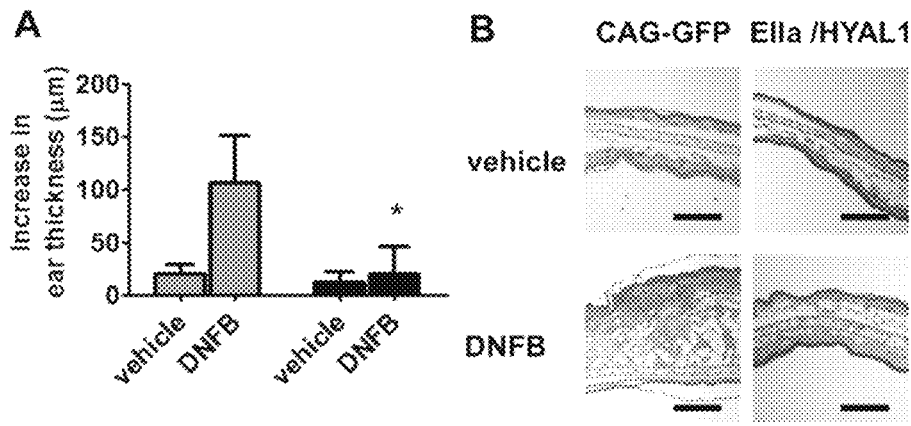
FIGURE 19A-B

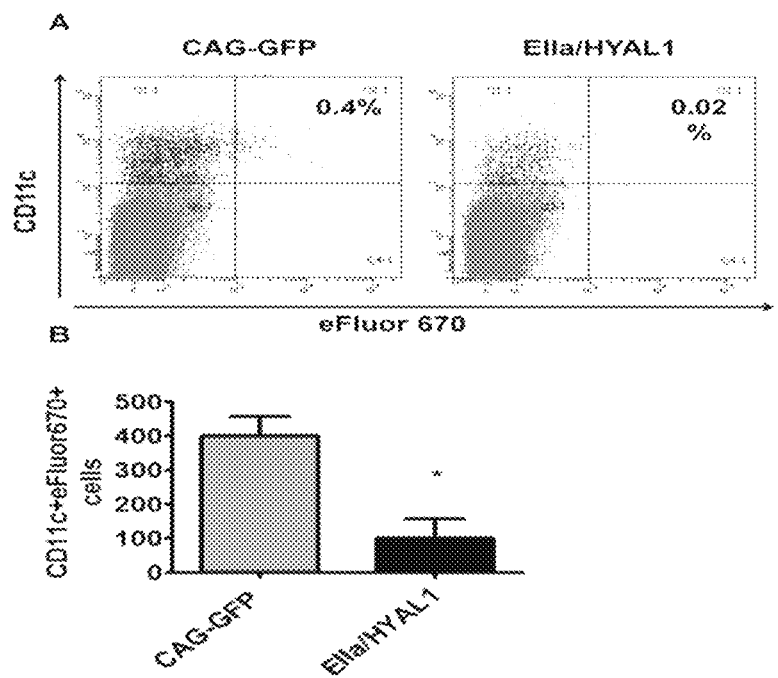
FIGURE 20A-B
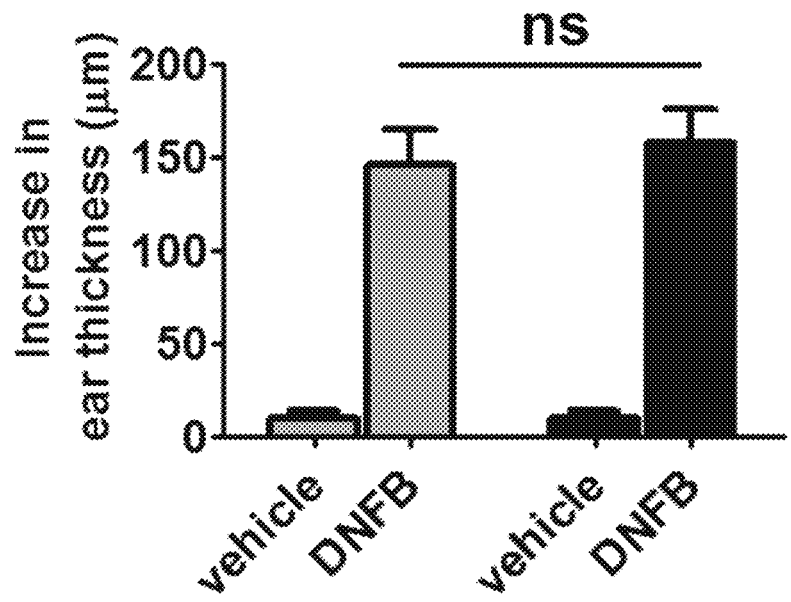
FIGURE 21

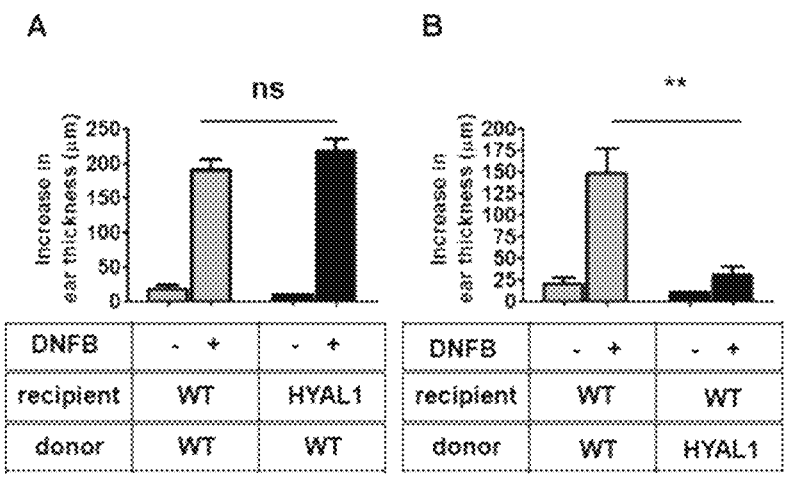
FIGURE 22A-B
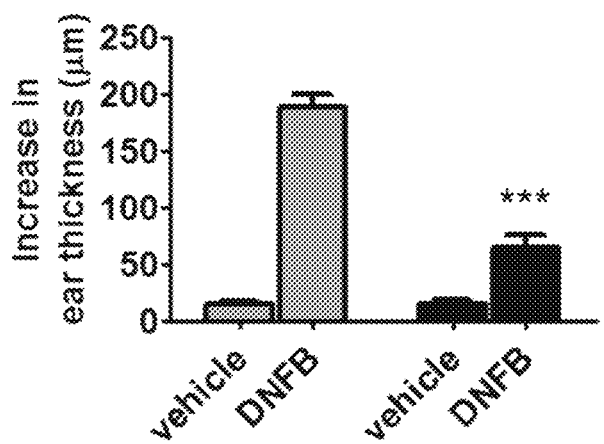
FIGURE 23

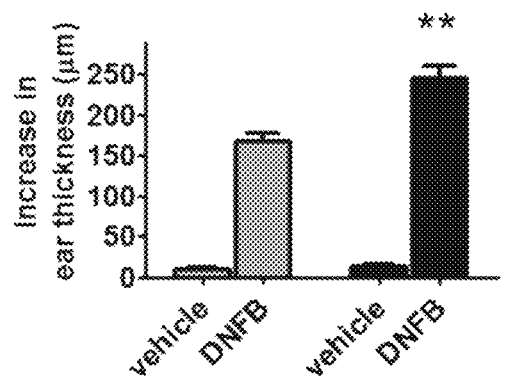
FIGURE 24
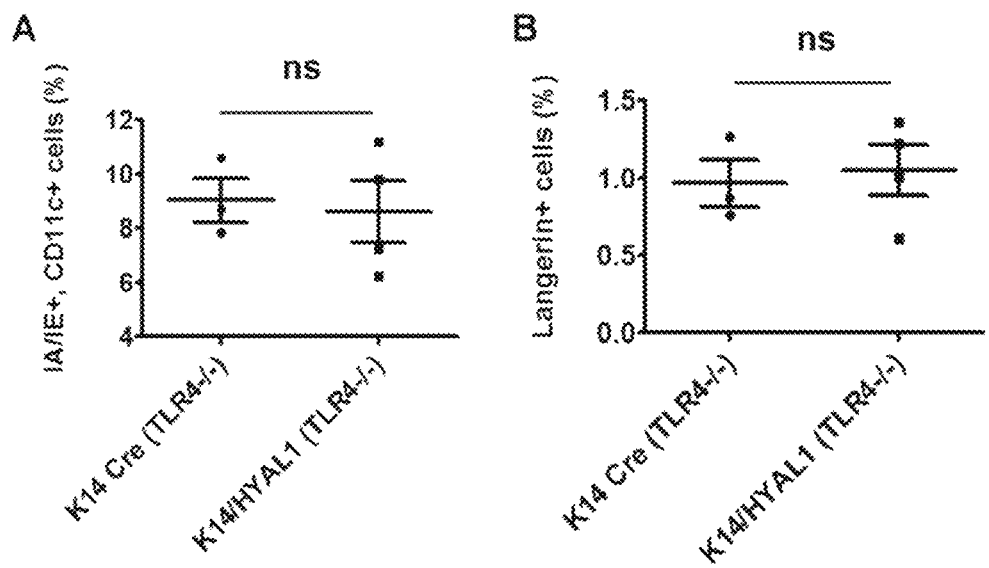
FIGURE 25A-B
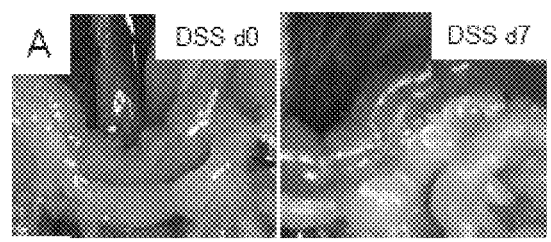
FIG. 26A

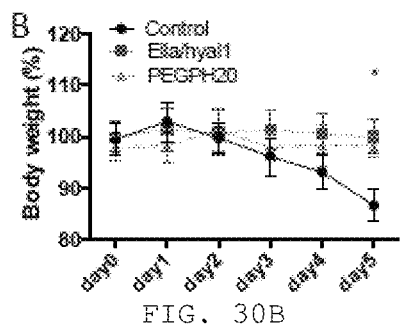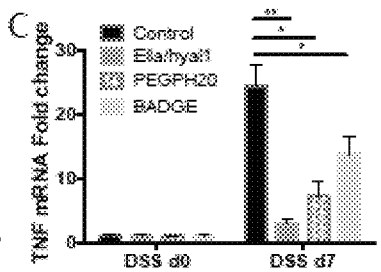
FIG. 30B  FIG. 30C
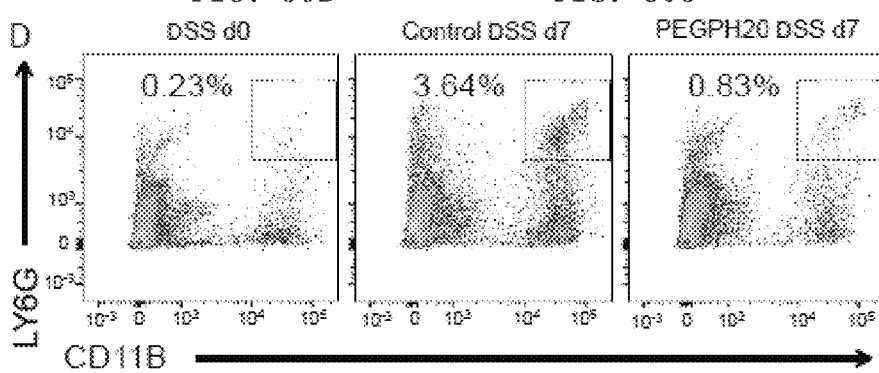
FIG. 30D
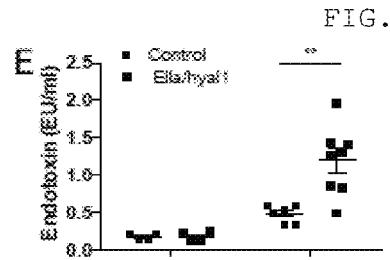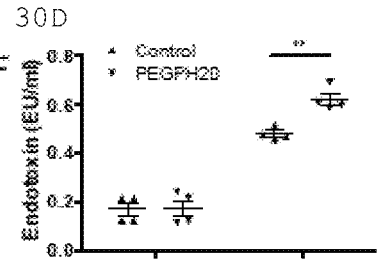
FIG. 30E  FIG. 30F
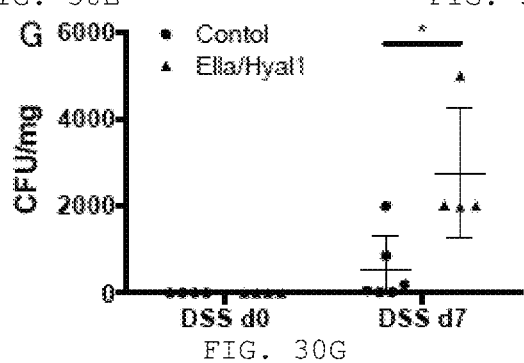
FIG. 30G
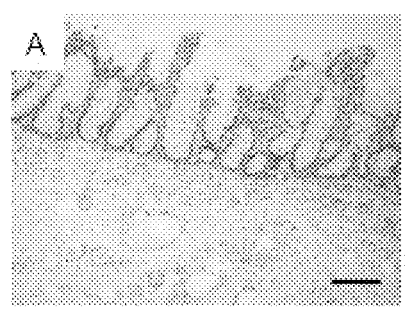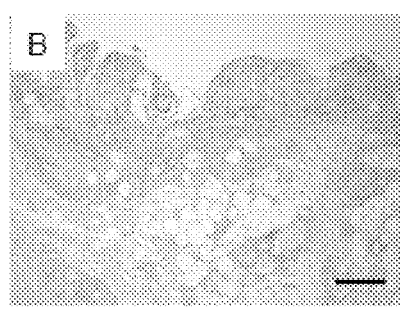
FIG. 31A  FIG. 31B

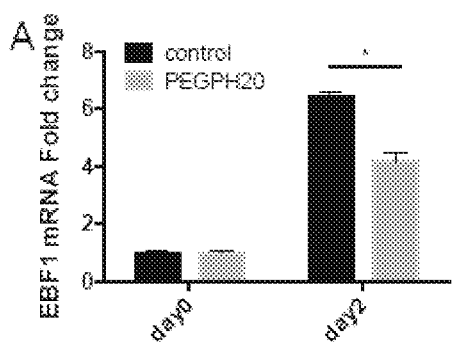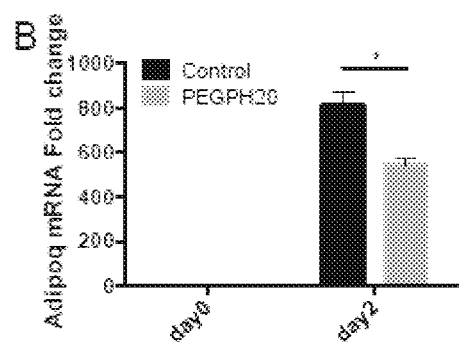
FIG. 32A  FIG. 32B
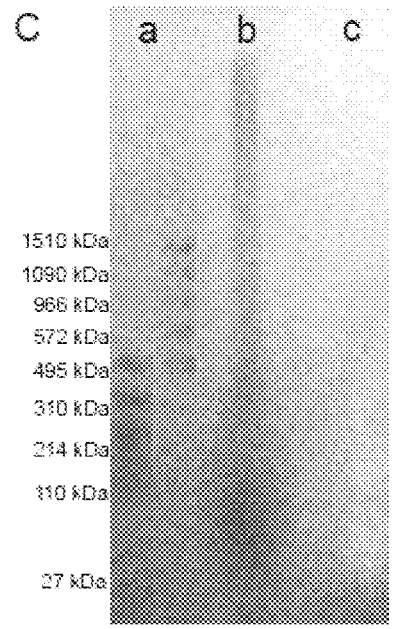
FIG. 32C
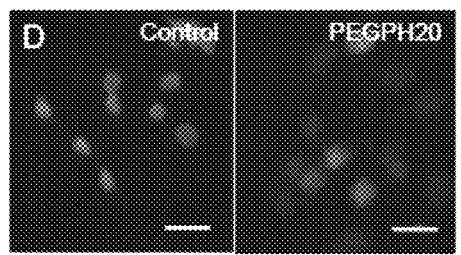
FIG. 32D
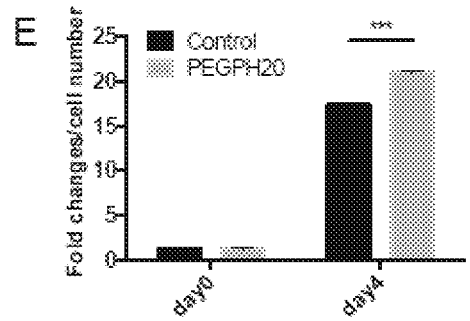
FIG. 32E

FIG. 37H-I

METHODS AND COMPOSITIONS TO PREVENT AND TREAT INFLAMMATION AND ALLERGIC REACTIONS

CROSS REFERENCE TO RELATED APPLICATIONS

This application claims priority under 35 U.S.C. § 119 from Provisional Application Ser. No. 62/774,426, filed Dec. 3, 2018, the disclosure of which is incorporated herein by reference.

STATEMENT REGARDING FEDERALLY SPONSORED RESEARCH

This invention was made with Government support under Grant No. HL107150, awarded by the National Institutes of Health. The Government has certain rights in the invention.

TECHNICAL FIELD

The disclosure relates to compositions and methods for treatment of skin and bowel inflammation and diseases and for promoting allergic sensitization and vaccination.

BACKGROUND

Infections, inflammation and allergic reactions have detrimental effects and the health and well-being of a subject.

*Staphylococcus aureus* (*S. aureus*) and group A *Streptococcus* (GAS) are major bacterial pathogens responsible for invasive infections of human skin. The host immune response to these pathogens remains incompletely defined. The majority of research has focused on mechanisms to limit invasion of these bacteria by the actions of resident and recruited immunocytes as well as the innate antimicrobial functions of the epidermis. However, upon disruption of the epidermal barrier, *S. aureus* or GAS encounter a very different physical environment in the dermal ECM. As a consequence, the virulence of these pathogens includes exploitation of ECM components. For example, GAS evades resident leukocyte killing by expressing long chains of hyaluronan (HA) on its surface to mimic the HA-rich ECM in the surrounding environment of the dermis. *S. aureus* also has adapted to HA and utilizes its hyaluronidases to facilitate virulence. Currently, the interplay between bacterial and host HA catabolic systems has left unanswered the central question of how mammalian HA turnover during injury influences microbial resistance.

Inflammatory bowel disease (IBD) is characterized by chronic inflammation of the gastrointestinal tract and has been associated with poor quality of life and frequent complications requiring hospitalization and surgical procedures. 3.1 million (1.3%) U.S. adults received a diagnosis of IBD in 2015. Direct treatment costs were recently estimated to exceed 6.8 billion dollars in the US while in Europe, estimates from 2013 suggest that 2.5±3 million people are affected and contribute to an overall direct health care cost of 4.6±5.6 billion Euros per year.

Current therapies for IBD typically target neutralization of inflammatory cytokines, blockade of receptors, or inhibition of inflammatory cell functions. Despite current approaches, it is still difficult to control disease severity and maintain quality of life. One important phenotype of IBD that may offer an opportunity for gaining increased understanding of the disease is that up to 40% of individuals with inflammatory diseases of the colon have extraintestinal manifestations. Foremost in these extraintestinal symptoms are skin or oral disorders such as erythema nodosum, pyoderma gangreneosum and aphthous stomatitis. The presence of diseases associated with IBD at sites far from the gut support several hypotheses that IBD is a systemic disorder of circulating bone marrow derived immunocytes, a consequence of dysbiosis of the microbiome or a generalized disorder of epithelial function. Indeed, the close interplay of microbes with multiple tissue and cell types supports the hologenome theory of evolution that suggests the function of both human and microbial cell types is necessary for tissue homeostasis. Appropriate function of the epithelial barrier is necessary to regulate the interactions between microbes and the host and maintain health.

HA is a linear polysaccharide found in the ECM of all vertebrates. The functions of HA are diverse as it is necessary for mammalian development and migration, and also serves important functions in cancer and other diseases. Consistent with the important function of HA, the synthesis and degradation of this polysaccharide is strictly regulated and in constant dynamic equilibrium. A family of mammalian hyaluronan synthases and hyaluronidases are employed in a cell and tissue specific manner to regulate tissue HA content. Importantly, upon injury, HA is rapidly degraded and this catabolic reaction results in important changes in the local immune response. HA fragments interact with Toll-like receptor 4 to activate cell responses during injury and have been proposed to act as a way to complement pathogen detection mechanisms. Bacterial hyaluronidases such as HysA expressed by *S. aureus* degrade HA differently than the mammalian hyaluronidases and thus generate alternative products with distinct functions. However, despite the important role of HA during injury, the mechanism responsible for local regulation of HA turnover and its contribution to host defense against infection has not been elucidated.

SUMMARY

The disclosure demonstrates that increased oligoHA in the skin can suppress contact hypersensitivity reactions in vivo. An oligoHA cream applied on the skin before sensitization attenuated an allergy reaction after elicitation. OligoHA subcutaneous injection before sensitization also suppressed this reaction. Thus, oligoHA treatment can be used for treatment to control skin allergy reaction. The disclosure further demonstrates that oligoHAs lower or deplete a contact site of dendritic cells. Accordingly, using oligoHA treatment to suppress contact hypersensitivity reaction is provided. In one embodiment, the compositions and methods use a tetrasaccharide of HA to suppress allergy or allergic reactions.

In one embodiment, the disclosure provides a topical cream containing a formulation of HA tetrasaccharides. This composition can be applied and used for treating or inhibiting any disease that requires the function of skin dendritic cells. One method includes application of the composition in contact dermatitis such as "poison ivy dermatitis", and many occupational skin allergic diseases. Other skin diseases such as graft vs host disease, psoriasis and atopic dermatitis can also benefit from alteration of skin dendritic cell function through the use of injected or topical oligoHA.

The disclosure also demonstrates that oligoHA causes a migration of dendritic cells out of the site of contact and into the lymph nodes. Thus, contacting a subject with oligoHA simultaneously, immediately before or immediately after, vaccination with an antigen or allergen promotes dendritic cell activation and migration of the activation dendritic cells to the lymph node thereby improving sensitization.

Inflammatory bowl disease (IBD) is associated with bacterial trans-location out of the colon and is accompanied by local adipogenesis. The disclosure demonstrates that HA influences bacterial trans-location in colitis by effecting adipogenesis. The disclosure demonstrates that digestion of HMW-HA by addition of hyaluronidase inhibited adipocyte differentiation as seen by decreased mRNA for zfp521 ($p=0.02$), zfp423($p=0.01$), Adiponectin ($p=0.004$), and decreased lipid droplets and expression of AMP. In vivo, tissue specific expression of human-hyaluronidase 1 (hHYAL1) in mice resulted in HA digestion in the colon without changing expression of HAS1, 2, 3 and HYAL1, 2, 3. HA digestion prior to induction of DSS colitis resulted in less proliferation of adipogenic fibroblasts expressing PDGFRα, lower expression of mRNA for EBF1 (0.007), zfp423($p=0.05$) and PPARγ ($p=0.003$) but not C/EBPα ($p=0.14$) or Adiponeqtin ($p=0.72$), and less mature fat tissue seen by immunohistochemistry. DSS colitis resulted in increased bacterial trans location in hHyal1 mice with more bacteria cultured from mesentery fat ($p=0.01$) and more bacterial DNA detected by qPCR ($p=0.001$). These results suggest that the local adipogenesis seen in IBD plays an important role in protection against bacterial trans-location out of the colon and that loss of HMW-HA may inhibit this response. These results show that local adipogenesis seen in IBD plays an important role in protection against bacterial trans-location out of the colon as seen in skin and HA contribute to this response.

The disclosure also demonstrates that reduction in hyaluronidase activity in the degradation of HMW-HA results in increased adipogenesis, increased production of AMPs and reduced infection by bacterial pathogens, e.g., *S. aureus*. Accordingly, the disclosure provides a method of inhibiting bacterial infection by inhibiting degradation of HMW-HA and/or application of HMW-HA and/or inducing HMW-HA synthesis.

In a particular embodiment, the disclosure provides a composition for administration to an epithelial layer of a subject to reduce inflammation comprising HA fragments (OligoHA) and/or an HA-degrading enzyme. In a further embodiment, the OligoHA comprise one or more of di-, tri-, tetra- and hexasaccharides. In yet a further embodiment, the HA-degrading enzyme is hyaluronidase (derived from testis), hyaluronidase (derived from *Streptomyces*), hyaluronidase SD, chondroitinase ACI, chondroitinase ACIII, chondroitinase ABC and endoglucuronidase (derived from leech).

In another embodiment, the disclosure also provides for a method of treating or inhibiting an allergic or inflammatory reaction of the skin or gastrointestinal tract comprising contacting the skin or gastrointestinal tract with a composition or preparation disclosed herein. In a further embodiment, the composition comprises tetra-oligosaccharide fragments of HA and/or wherein the composition comprises a hyaluronidase. In yet a further embodiment, the application or contacting is in the form of a cream, lotion, spray or gel or an enteric formulation for delivery to the small intestine at a pH of about 4.5-6. In yet a further embodiment, the allergic or inflammatory reaction is selected from the group consisting of colitis, IBD, allergic reactions, contact dermatitis, psoriasis, atopic dermatitis, histiocytosis X (Langerhans histiocytosis), graft vs. host disease and disorders and other disease and disorders comprising dendritic cell activation or migration.

In a particular embodiment, the disclosure further provides a method of inducing allergic sensitization to an agent comprising contact a subject with the agent and a composition or preparation disclosed herein. In a further embodiment, the contacting is simultaneous. In alternate embodiment, the contacting of the agent and composition is within 1-30 minutes of each other.

In a certain embodiment, the disclosure provides a composition comprising therapeutically effective amounts of substantially purified oligosaccharide fragments of hyaluronan (OligoHA) and/or therapeutically effective amounts of a substantially purified enzyme that degrades hyaluronan into oligosaccharide fragments, for use in one or more of the following: (a) to modulate allergic reactions of the skin and gut by reducing inflammatory cells in the region of a potential or actual allergic/inflammatory reaction; (b) to modulate inflammation of the skin and/or gut; (c) as an adjuvant to promote sensitization to an antigen/allergen; (d) to inhibit or reduce adipogenesis in the skin and/or gut; (e) to reduce or inhibit adipocyte differentiation; and/or (f) to inhibit cathelicidin production. In a further embodiment, the composition comprises di-, tri-, tetra- and/or hexasaccharide fragments of hyaluronan. In yet a further embodiment, the composition comprises 60% or more by weight or by composition of tri and/or tetra-hexasaccharide fragments of hyaluronan. In yet a further embodiment, the composition comprises 80% or more by weight or by composition of tri and/or tetra-hexasaccharide fragments of hyaluronan. In another embodiment, the enzyme is selected from the group consisting of: a hyaluronidase derived from humans, a hyaluronidase derived from *Streptomyces*, a hyaluronidase SD, a chondroitinase ACI, a chondroitinase ACIII, a chondroitinase ABC and an endoglucuronidase derived from leeches. In yet another embodiment, the hyaluronidase derived from humans is selected from the group consisting of: HYAL1, HYAL2, HYAL3, HYAL4, HYAL5 and HYAL6. In a further embodiment, the composition is formulated for topical or oral administration to a subject in need thereof. In another embodiment, the composition comprises OligoHA and the enzyme that degrades hyaluronan into oligosaccharide fragments.

In a certain embodiment, the disclosure also provides a method to reduce or inhibit inflammation in a subject in need of treatment thereof, comprising: administering a therapeutically effective amount of a composition of preparation disclosed herein to the subject. In a further embodiment, the inflammation is associated with an inflammatory disease or disorder, or associated with a bacterial infection. In yet a further embodiment, the inflammatory disease or disorder is selected from the group consisting of ulcerative colitis, inflammatory bowel disease, Crohn's disease, dermatitis, psoriasis, sinusitis, active hepatitis, asthma, rheumatoid arthritis, osteoarthritis, vasculitis, lupus, and fibromyalgia.

In a certain embodiment, the disclosure further provides a method to reduce or inhibit adipogenesis and/or adipocyte differentiation in a subject in need of treatment thereof, comprising: administering a therapeutically effective amount of a composition or preparation disclosed herein to the subject. In a further embodiment, the composition is topically administered to reduce or inhibit adipogenesis and/or adipocyte differentiation in dermal and/or hypodermal tissue. In an alternate embodiment, the composition is orally administered to reduce or inhibit adipogenesis and/or adipocyte differentiation in the gastrointestinal track. In a further embodiment, the adipogenesis and/or adipocyte differentiation in the gastrointestinal track is associated with an inflammatory gastrointestinal disorder or disease.

In a particular embodiment, the disclosure further provides a method to promote sensitization to an antigen/allergen in a subject, comprising: administering a therapeutically effective amount of a composition a preparation disclosed herein to the subject; and delivering an antigen/allergen to the subject. In a further embodiment, the composition is administered prior to, simultaneously with, or immediately after delivering the antigen/allergen to the subject. In yet a further embodiment, administration of a composition or preparation disclosed herein prior to the delivering the antigen/allergen induces anergy in the subject. In another embodiment, a composition or preparation disclosed herein is administered within 30 minutes of the delivery of the antigen/allergen to the subject. In a further embodiment, administration of a composition or preparation disclosed herein induces dendritic cell maturation and/or migration.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A-D shows OligoHA suppresses CHS through TLR4. (a) CHS response in the C57B6 WT mice injected subcutaneously with OligoHA or PBS in the dorsal skin 3 days before sensitization with DNFB. Grey bar and black bar indicate PBS and oligoHA injected mice respectively. The results represent the increase in the ear thickness for groups of five mice. (b) CHS response in the TLR4 deficient mice injected subcutaneously with OligoHA (black bar) or PBS (grey) in the dorsal skin before sensitization with DNFB. Mean and SEM of five mice are shown on the graph. Data are representative of three separate experiments with similar results. (c) DCs/mm$^2$ were determined by counting MHC class II immunostained cells in seven different areas in the epidermal sheets of oligoHA and PBS injected dorsal skins. (d) Epidermal sheets were stained with MHC II monoclonal antibody. Bar represents 50 um ***: $p<0.001$.

FIG. 2 shows oligoHA cream suppresses CHS. CHS response in the C57B6 WT mice applied on the dorsal skin with OligoHA cream 3 days before sensitization with DNFB. Grey bar and black bar indicate vehicle and oligoHA cream treated mice respectively. The results represent the increase in the ear thickness for groups of five mice. ***: $p<0.001$.

FIG. 3A-H shows strategy for HYAL 1 gene overexpression and restoration of CHS response in HYAL 1 overexpressing mice. (a) Gene schematic for conditional overexpression of human HYAL 1 gene. Filled triangles represent loxP sites. (b) The size distribution of HA in the transgenic mice skin is analyzed by agarose gel electrophoresis. The gel was stained with Stains-All. Lane 1: EIIa-cre mice, lane2: HYAL 1 overexpressing mice (EIIa-cre/CAG-HYAL1 Tg mice), lane 3: Human umbilical cord HA (c) HA immunostaining using HABP. Frozen sections of EIIa-cre/CAG-HYAL1 Tg mice and control EIIa-cre mice skins were stained with HABP and Fluorescein isothiocyanate-streptoavidin. Bar represents 100 μm. (d) Normal skin of control mice (CAG-GFP$^{floxed}$-HYAL1). and HYAL 1 overexpressing mice (EIIa-cre/CAG-HYAL1 Tg mice). Hematoxylin/Eosin staining. Bar represents 100 um. (e) DCs/mm$^2$ were determined by counting MHC class II immunostained cells in six different areas in the epidermal sheets of HYAL1 overexpressing mice (KRT14-Cre/CAG-HYAL1) and control mice (CAG-GFP$^{floxed}$-HYAL1). (f) Immunohistochemistry of MHCII in epidermal sheets. Scale bar=50 μm. (g) Representative dot plots of MHCII and CD11c double positive DCs in viable cells from epidermal sheet of transgenic mice. Control: CAG-GFP$^{floxed}$-HYAL1. Numbers within plots denote percent cells within the respective gates. (h) Percent of MHCII+CD11c+ DCs in epidermal sheets of mice. Mean±SEM (***: $p<0.001$, n=3 per group)

FIG. 4A-F shows overexpression of HYAL 1 in the skin suppresses CHS. (a)Restoration of CHS response in HYAL1 overexpressing mice (KRT14-Cre/CAG-HYAL1 Tg mice, black bar) compared with control mice (CAG-GFP$^{floxed}$-HYAL1 Tg mice, grey bar). The data represent the increase in ear thickness for groups of six mice±SEM. Data are representative of five independent experiments. (b) Representative histopathology of the ear of KRT14-cre/CAG-HYAL1 Tg mice and control mice elicitated with vehicle or DNFB. Hematoxylin and eosin staining. Bars represent 200 μm. (c) Defective trafficking of skin DCs in HYAL1 overexpressing transgenic mice. Representative of dot plots of eFluor670 fluorescence plotted against CD11c in viable cells from DLNs of transgenic mice 24 h after painting with eFluor670 on the shaved abdominal skin. Control: KRT14-cre. (d) Number of CD11c+eFluor670+ DCs in DLNs of transgenic mice (n=3 per group) (e) Lymph node cells from sensitized CAG-GFP$^{floxed}$-HYAL1 were adoptively transferred by i.v. injection and sensitized KRT14-cre/CAG-HYAL 1 and CAG-GFP$^{floxed}$-HYAL1 Tg mice. Ear elicitation with DNFB and measurement of ear thickness were performed for groups of four mice. (f) Lymph node cells from sensitized KRT14-cre/CAG-HYAL 1 and CAG-GFP$^{floxed}$-HYAL 1 Tg mice were adoptively transferred by i.v. injection and sensitized CAG-GFP$^{floxed}$-HYAL1 Tg mice. (n=4) Mean±SEM. *: $p<0.05$, ***: $p<0.001$, n.s.: not significant.

FIG. 5A-C shows a lack of decreased DC number and CHS suppression in TLR4 deficient HYAL1 overexpressing mice. (a) DCs/mm$^2$ were determined by counting MHC class II immunostained cells in eight different areas in the epidermal sheets of TLR4 deficient KRT14-Cre/CAG-HYAL1 Tg mice and TLR4 deficient control mice (KRT14-cre mice). (b) Immunohistochemistry of epidermal sheets with MHC II monoclonal antibody. Bar represents 50 um. (c) Evaluation of CHS in TLR4 deficient HYAL 1 overexpressing mice. Black bar and grey bar represent TLR4 deficient KRT14-cre/CAG-HYAL1 and TLR4 deficient control mice (CAG-GFP$^{floxed}$-HYAL1 tg mice). The data represent the increase in ear thickness for groups of five mice±SEM. n.s.: not significant.

FIG. 6A-G shows generation of HYAL 1 overexpressing mice. (A) Schematic for conditional overexpression of HYAL1. Filled triangles represent loxP sites. (B) Fluorescence images of transgenic mice pups (approximately 2 days old) expressing green fluorescent protein (CAG-GFPfloxed-HYAL1 Tg mice: CAG-GFP and EIIa/HYAL1 mice) and EIIa-Cre mice. (C) Quantitative PCR demonstrating HYAL1 overexpression in normal skin from EIIa/HYAL1 mice and control mice (CAG-GFP). (*: $p<0.05$, n=6). (D) Frozen sections of skin from HYAL1 overexpressing mice (K14/HYAL1) and control mice (CAG-GFP) were stained with an antibody recognizing HYAL1 (red). Scale bar=100 μm, n=5 per group. (E) HA immunostaining. Frozen sections of skin from EIIa/HYAL1 mice and control EIIa-Cre mice were stained with HABP and Fluorescein isothiocyanate-streptoavidin (green). 4', 6-diamidino-2-phenylindole (DAPI) for nucleus (blue). Scale bar=100 μm, n=5 per group. (F) The size distribution of HA extracted from skin as analyzed by agarose gel electrophoresis. A similar total amount of HA was loaded in each lane as determined by carbazole assay. Gel was stained with Stains-All. Lane 1: molecular weight markers, lane 2: HA extracted from the skin of control EIIa-Cre mice, lane 3: HA extracted from skin of HYAL1 expressing mice (EIIa/HYAL1) shows decrease in average detectable size to <27 kDa, lane 4: human umbilical cord HA as standard. (G) Skin of control mice (CAG-GFP) and HYAL1 overexpressing mice (EIIa/HYAL1) stained with Hematoxylin/Eosin. Scale bar=100 µm. Data are representative of three independent experiments with similar results.

FIG. 7A-G shows decreased DC number in the epidermis and dermis of HYAL1 overexpressing mice. (A) Representative dot plots of MHC class II and CD11c double positive viable DCs from epidermal sheets of transgenic mice. Control: CAG-GFP. Numbers within plots denote the percent of cells within the respective gates. (B) Percentage of MHC class II+CD11c+DCs in epidermal sheets of mice by flow cytometry. (***: $p<0.001$, n=3) (C) Immunohistochemistry of MHC class II in epidermal sheets. Scale bar=50 µm. (n=6). (D) Dermal single cell suspensions of K14/HYAL1 mice and control mice (K14-Cre) were subjected to flow cytometry analysis and MHC class II and CD11c positive cell numbers were assessed. (E) Number of Langerin positive cells among MHC class II and CD11c positive cells. (*: $p<0.05$, n=3). Mean±SEM (F) Flow cytometry analysis of dermal single-cell suspensions showing expression of CD11b and CD103 from K14/HYAL1 mice and control mice (K14-Cre mice). Cells were gated on Langerin+, MHC class II+ and CD11c+ cells. (G) Cells gated on Langerin negative, MHC class II+ and CD11c+ cells showing expression of CD11b and CD103. Numbers represent the percentage of the cells in the indicated gate. Data are representative of three independent experiments.

FIG. 8A-G shows decreased DC number in the epidermis of K14-CreERT/HYAL1 mice after tamoxifen application. (A) DCs/mm2 were determined by counting MHC class II immunostained cells in eight different microscopic fields of the epidermal sheets 0, 24, 48, and 72 hours after topical tamoxifen application. Mean and SEM are shown on the graph (n=4). (B) 0, 24, 48, 72 hours after tamoxifen treatment, epidermal sheets were harvested and stained with MHC class II antibody. Scale bar=50 µm. (C) 48 hours after tamoxifen treatment, epidermal sheets were stained with CD80 antibody. Scale bar=50 µm. (D) Increased trafficking of skin DCs in tamoxifen-dependent HYAL1 overexpressing transgenic mice. Representative plots of eFluor670 fluorescence plotted against CD11c from draining lymph nodes (DLNs) of transgenic mice 24 h after painting eFluor670 dissolved in acetone on shaved and tamoxifen or vehicle treated abdominal skin. (E) Number of CD11c+eFluor670+ DCs in DLNs of tamoxifen-dependent HYAL1 overexpressing mice (K14CreERT/HYAL1, black bar) compared with vehicle-treated control mice (K14CreERT/HYAL1, grey bar) (n=4). (F) Representative dot plots of CD11c against side scatter from DLNs of transgenic mice 72 h after tamoxifen or vehicle treatment on abdominal skin. (G) Percent of CD11c+ DCs in DLNs of tamoxifen-dependent HYAL1 overexpressing mice (K14CreERT/HYAL1, black bar) compared with vehicle-treated control mice (K14CreERT/HYAL1, grey bar) (n=4). Mean and SEM are shown on the graph. Data are representative of two separate experiments with similar results. *:$p<0.05$, ***:$p<0.001$.

FIG. 9A-D shows oligoHA induces DC emigration and maturation. (A) DCs/mm2 were determined by counting MHC class II immunostained cells in eight different microscopic fields of the epidermal sheets 0, 2, 4, 8 and 24 hours after oligoHA (400 µg) or PBS injection of C57B6 WT mice. (B) Frequency of CD80+ cells in MHC class II+cells in the epidermal sheets after injection. (C) 2 hours after injection, epidermal sheets were harvested and stained with MHC class II or CD80 monoclonal antibody. Mean and SEM are shown on the graph (n=4). Scale bar=50 µm. (D) Increased DCs in draining lymph nodes after oligoHA injection (400 µg). Representative dot plots of FITC fluorescence plotted against CD11c from DLNs of C57B6 WT mice 24 h after painting FITC dissolved in acetone on shaved abdominal skin. Data are representative of two or three separate experiments with similar results. ***:$p<0.001$.

FIG. 10A-G shows constitutive overexpression of HYAL 1 in the skin suppresses CHS. (A) Restoration of the CHS response in HYAL1 overexpressing mice (K14/HYAL1, black bar) compared with control mice (CAG-GFP, grey bar). The data represent the increase in ear thickness for groups of six mice. (B) Representative histopathology of the ears of K14/HYAL1 mice and control mice elicited with vehicle or DNFB. Hematoxylin and eosin staining. Scale bar=200 µm. (C) Defective trafficking of skin DCs in HYAL1 overexpressing transgenic mice. Representative dot plots of eFluor670 fluorescence plotted against CD11c in viable cells from DLNs of transgenic mice 24 h after painting eFluor670 dissolved in 1:1 acetone/dibutylphthalate on shaved abdominal skin. (D) Number of CD11c+ eFluor670+ DCs in DLNs of transgenic mice (n=3) (E) Lymph node cells from sensitized CAG-GFP mice were adoptively transferred by i.v. injection into K14/HYAL1 and CAG-GFP mice. Ear elicitation with DNFB and measurement of ear thickness were performed for groups of four mice. (F) Lymph node cells from sensitized K14/HYAL1 and CAG-GFP mice were adoptively transferred by i.v. injection into CAG-GFP mice. Ear elicitation with DNFB and measurement of ear thickness were performed for groups of four mice. (G) CHS response in C57B6 WT mice injected subcutaneously with oligoHA (black bar) or PBS (grey bar) in the dorsal skin 72 hours before sensitization with DNFB. (n=5) Mean±SEM. *: $p<0.05$, ***: $p<0.001$, n.s.: not significant. Data are representative of three independent experiments.

FIG. 11A-D shows tamoxifen-dependent overexpression of HYAL1 or injection of HA tetrasaccharides accelerates sensitization of CHS. (A, B) CHS response after early elicitation (1.5 days after sensitization) in tamoxifen-dependent HYAL1 overexpressing mice (K14CreERT/HYAL1, black bar) compared with acetone/DMSO-treated control mice (K14CreERT/HYAL1, grey bar). The data represent the increase in ear thickness for groups of four mice. (C, D) CHS response after early elicitation (1.5 days after sensitization) in mice injected with oligoHA (400 µg, black bar) or PBS (grey bar) subcutaneously at the same time and site of sensitization. The results represent the increase in the ear thickness of groups of five mice. Mean±SEM. ***: $p<0.001$. Data are representative of two independent experiments.

FIG. 12A-E shows modification of DC function by HA catabolism is TLR-4 dependent. (A) DCs/mm2 were determined by counting MHC class II immunostained cells in eight different microscopic fields of the epidermal sheets of K14/HYAL1, K14-Cre, TLR4 deficient K14/HYAL1, and TLR4 deficient K14-Cre mice. (n=4) (B) Increased DCs in DLN after injection with oligoHA subcutaneously at the same time and site of FITC application. Number of CD11c+ FITC+DCs in DLNs of oligoHA injected C57B6 WT mice and TLR4 deficient mice compared with PBS injected control mice 24 h after painting FITC on shaved abdominal skin was analyzed by flow cytometry. (n=4). (C) Evaluation of CHS in TLR4 deficient HYAL1 overexpressing mice. The black bar and the dark grey bar represent TLR4 deficient K14/HYAL1 and control mice (K14-Cre), respectively. The data represent the increase in ear thickness for groups of five mice. (D) CHS response in C57B6 WT mice and TLR4 deficient mice injected subcutaneously with oligoHA or PBS in the dorsal skin 72 hours before sensitization with DNFB. (n=5) (E) Increase in ear thickness after early elicitation with DNFB (1.5 days after sensitization). C57B6 WT mice and TLR4 deficient mice were injected subcutaneously with oligoHA or PBS at the same time and site of sensitization. (n=5) Mean and SEM are shown on the graph. *:$p<0.05$, ***:$p<0.001$, n.s.: not significant. Data are representative of two independent experiments.

FIG. 13A-B show (a) a plasmid map and (b) a schematic representation for construction of pCFE expression system. SD=splice donor, SA=splice acceptor, CAT=chloramphenicol acetyl transferase gene, eGFP=enhanced green fluorescent protein; insulator=chicken (β-globin HS4 insulator; Cre=Cre recombinase; loxP=target for Cre recombinase.

FIG. 17 shows Il-10 mRNA expression in K14/HYAL1 mice. Quantification of Il-10 mRNA expression in mouse skin and LN. n=5 per group, Mean±SEM. n.s.: not significant. Data are representative of three independent experiments.

FIG. 18 shows HYAL1 mRNA expression in K14CreERT/HYAL1 mice before and after tamoxifen application. Quantification of HYAL1 mRNA expression in mouse skin. n=3, Mean±SEM. *: $p<0.05$, **: $p<0.01$. Data are representative of two independent experiments.

FIG. 19A-B shows overexpression of HYAL1 suppresses CHS. (A) The results represent the increase in ear thickness for groups of five mice 24 hours after elicitation. The black bar and the grey bar represent EIIa/HYAL1 and CAG-GFP mice, respectively. Mean and SEM are shown. *: $p<0.05$ (B) Histopathology of the ears of EIIa/HYAL1 and control mice (CAG-GFP) elicited with vehicle or DNFB stained with Hematoxylin and Eosin. Scale bars=200 μm. Data are representative of three independent experiments.

FIG. 20A-B shows overexpression of HYAL1 suppresses DC migration in eFluor670 treated mice. (A) Representative dot plots of eFluor670 fluorescence plotted against CD11c in viable cells from DLNs 24 h after painting eFluor670 on the shaved abdominal skin of HYAL1 overexpressing mice (EIIa/HYAL1) and control mice (CAG-GFP). (B) Number of CD11c+eFluor670+ DCs in DLNs of transgenic mice. (n=3 per group). *: $p<0.05$ Data are representative of three independent experiments.

FIG. 21 shows Hyal1 is not essential for CHS. The result represents the increase in ear thickness for groups of five mice 24 hours after elicitation. The black bar and the grey bar represent Hyal1 deficient and control mice, respectively. Mean and SEM are shown. n.s.: not significant. Data are representative of two independent experiments.

FIG. 22A-B shows absence of CHS sensitization in HYAL1 overexpressing mice. (A) Lymph node cells from sensitized CAG-GFP mice were adoptively transferred by i.v. injection into EIIa/HYAL1 and CAG-GFP mice. Ear elicitation with DNFB was followed by measurement of ear thickness for groups of four mice. (B) Lymph node cells from sensitized EIIa/HYAL1 and CAG-GFP mice were adoptively transferred by i.v. injection into CAG-GFP mice. Ear elicitation with DNFB was followed by measurement of ear thickness for groups of four mice. Mean and SEM are shown. **: $p<0.01$, n.s.: not significant. Data are representative of three independent experiments.

FIG. 23 shows early tamoxifen-dependent overexpression of HYAL1 before sensitization suppresses CHS. The result represents the increase in ear thickness for groups of five mice 24 hours after elicitation. The black bar and the grey bar represent tamoxifen or acetone/DMSO treated K14CreERT/HYAL1 mice, respectively. Mean and SEM are shown. ***: $p<0.001$.

FIG. 24 shows tamoxifen-dependent overexpression of HYAL1 augments CHS. The result represents the increase in ear thickness for groups of four mice 24 hours after elicitation. The black bar and the grey bar represent K14CreERT/HYAL1 and K14CreERT mice, respectively. Mean and SEM are shown. **: $p<0.01$. Data are representative of two independent experiments.

FIG. 25A-B shows TLR4 deficiency reverses the decrease of dermal DC in HYAL1 overexpressing mice. (A) Percentage of MHC class II and CD11c positive cells in the dermis. Dermal single-cell suspensions of TLR4 deficient K14/HYAL1 mice and TLR4 deficient control mice (K14-Cre mice) were subjected to flow cytometric analysis. (n=3-4 per group) (B) Frequency of Langerin positive cells among MHC class II and CD11c positive cells. (n=3-4 per group) n.s.: not significant. Data are representative of two independent experiments.

FIG. 26A-G shows submucosal adipocytes expand in response to DSS colitis. (A,B,D,E) shows representative clinical and histology of distal colon sections from control mice or mice at the first day and 7 days after being provided with 3% DSS colitis in drinking water and 42 days after chronic DSS treatment. Tissue was stained with Hematoxylin and eosin or anti-PREF1/DLK antibodies. β-gal staining of the Zfp4231acZ/+ colon 7 days after provided with DSS. Brackets delineate submucosal region occupied by adipocytes. Scale Bar=50 Microns. (C) Total RNA was extracted and purified mRNA. were measured by RTqPCR for the relative abundance of adipocyte genes Pref1, Zfp423, Ebf1. mRNA expression was normalized to β-actin (n=5 mice/group). (F,G) Representative histology from colon sections from Crohn's disease (CD) or Ulcerative colitis (UC) patients with inflamed part or normal part (n=5). Tissues were stained by anti-PREF1/DLK antibody. F:Normal colon from CD. G: Inflamed colon from the same patient. Scale Bar=10 Microns. All error bars indicate mean± SEM; *$P<0.05$, $P<0.01$, *$P<0.001$ (t test).

FIG. 30A-G shows colon inflammation response is inhibited by Hyaluronidase. (A) Representative histology of distal colon sections in colitis of WT, Ella/hyal1 and PEGPH20 injected mice were stained with H&E. (B) During the 3% DSS water feeding, body weight were measured everyday and normalized to that of original body weight (n=4 mice/group). (C) TNF mRNA expression in colon samples (n=4 control or BADGE and PEGPH20 or 6 Ella/Hyal1 mice/group). (D) Flow cytometry analysis of colon lamina propria single cell suspensions showing expression of LY6G and CD11B from DSS d0 control, DSS d7 control and PEGPH20 treated DSS d7 mice. Numbers represent the percentage of the cells in the indicated gate. (E) Endotoxin concentration in the serum from WT and Ella/hyal1. (n=6 control, n=8 Ella/hyal1 mice/group). (F) Endotoxin concentration in the serum from WT and PEGPH20 (n=4 mice/group). (G) Systemic bacteremia detected after colitis in mesenteric fat from WT and Ella/hyal1 mice (n=4 Ella/hyal1 N=6 WT mice/group). Scale Bar=50 Microns. All error bars indicate mean±SEM; P<0.01, *P<0.001 (t test).

FIG. 31A-B shows representative histology from colon sections from Crohn's disease (CD) patients with inflamed part or normal part (n=5). Tissues were stained by HA Binding protein. A: Normal colon from CD. B: Inflamed colon from the same patient. Scale Bar=20 Microns.

FIG. 32A-E shows mouse preadipocytes (3T3L1) were differentiated by the addition of adipocyte differentiation media with or without the addition of 20 ug/ml of recombinant hyaluronidase (PEGPH20). (A, B) Relative expression of mRNA for EBF1 and Adipoq, the difference of adipogenes expression between each group at day 2. (C) The size distribution of HA by Gel electrophoresis. HA were extracted from the same amount of supernatant collected at day4. a: MW marker, b: Control, c: PEGPH20. (D) Cells were incubated with BrdU for 4 hour. Proliferative preadipocyte were stained with anti-BrdU antibody. Scale Bar=50 Microns. (E) Cell numbers were analyzed by SRB assay and normalized to that of day 0 number. All error bars indicate mean±SEM; *P<0.05**, P<0.01 (t test).

FIG. 37A-I shows Cemip-/- mice resist infection by S. aureus. (A) Skin lesions on control and Cemip$^{-/-}$ mice 3 days after inoculation with 1×10$^6$ CFU of S. aureus. (B) Measurements of lesion size on mice after inoculation with S. aureus as in A. (C, D) Representative images taken by IVIS and quantification of luminescence in region of Interest (ROI) of skin from control and Cemip$^{-/-}$ mice 3 days after inoculation with 1×10$^6$ CFU of biolumensecent S. aureus. (E) CFU count of S. aureus recovered from the spleen 3 days after skin infection as in A. (F) mRNA expression from skin measured by qPCR of Camp (n=6 control and for +S. aureus). (G) Immunohistochemical staining for cathelicidin, DAPI in representative sections of skin from control and Cemip$^{-/-}$ mice 3 days after S. aureus infection. Scale Bar=50 Microns. Blue=DAPI. (H) Tissue extracts were subjected to immunoblotting analyses for Camp and beta-actin. (I) Quantification of the ratio of Camp to beta-actin. All error bars indicate mean±SEM; * P<0.05, P<0.01, *P<0.001 (t test).

DETAILED DESCRIPTION

Figure 14:
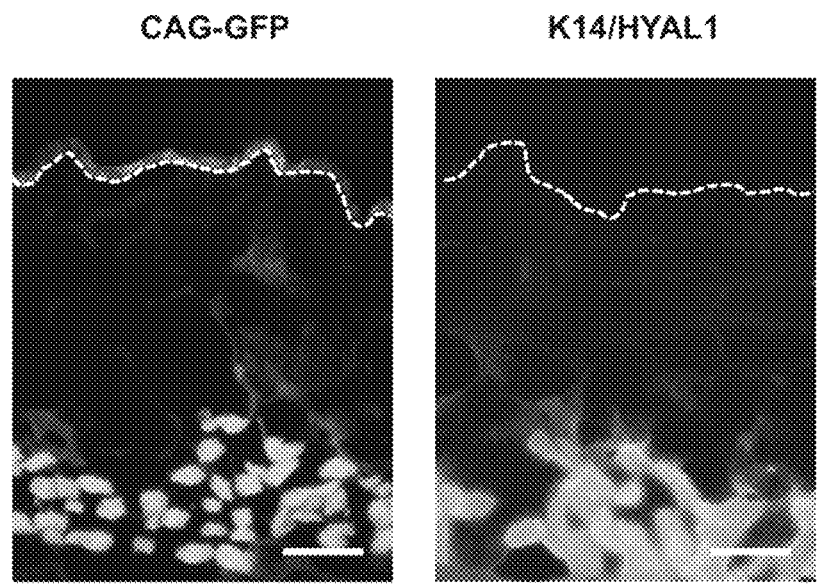
FIG. 14 shows loss of GFP expression in the epidermis of K14/HYAL1 mice. Fluorescence images of frozen sections of skin from HYAL1 overexpressing mice (K14/HYAL1) and control mice (CAG-GFP) expressing green fluorescent protein. Dashed line indicates basement membrane. Scale bar=100 μm.

As used herein and in the appended claims, the singular forms "a," "an," and "the" include plural referents unless the context clearly dictates otherwise. Thus, for example, reference to "a cell" includes a plurality of such cells and so forth.

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure. Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Hyaluronan (HA) is a major glycosaminoglycan (GAG) component of the extracellular matrix of many tissues. Hyaluronan is a linear unsulfated glycosaminoglycan composed of repeating units of the disaccharide [-D-glucuronicβ1, 3-N-acetyl-D-glucosamineβ1, 4-]. Structurally, high molecular weight (HMW) HA (approximately 1 million daltons or more) is composed of repeating disaccharide units of D-glucuronic acid and N-acetylglucosamine which exists as a random coil structure that can expand in aqueous solutions (Toole, 2004; Scott et al., 2002). Aqueous HA is highly viscous and elastic, properties which contribute to its space filling and filtering functions (Scott et al., 2002). It is abundant in many tissues including the skin where an estimated 50% of total body HA exists in the epidermis and dermis. It is thought that the function of HA is controlled by its degradation, which produced biologically active oligosaccharides. Small fragment HA (oligoHA) is generated during inflammation or injury. Proinflammatory cytokines (TNFα, IL-1β) and LPS induce HA production in EC in vitro (Mohamadzadeh et al., 1998) and increased HA levels are observed in bronchioalveolar lavage fluid (BALF) from patients with inflammatory lung disorders such as pulmonary fibrosis, acute lung injury, and chronic obstructive pulmonary disease (Bensadoun et al., 1996; Dentener et al., 2005; Nettelbladt et al., 1989; Teder et al., 1997). Intratracheal administration of nebulized high MW HA has been used to prevent injury in experimental emphysema (Cantor et al., 2004). Further, HA and CD44 regulate IL2-induced vascular injury syndrome in mouse lung (Mustafa et al., 2002; Rafi-Janajreh et al., 1999).

HA is degraded by hyaluronidases, under certain pathological inflammatory conditions, to produce lower molecular weight fragments found in tissue injury and serum of patients with certain malignancies (Orian-Rousseau et al., 2002; Orian-Rousseau et al., 2007). Hyaluronidases hydrolyze the hexosaminidic β1-4 linkages between N-acetyl-D-glucosamine and D-glucuronic acid residues in HA, digesting the large polymer into fragments. In humans, there are six members of the hyaluronidase family: hyaluronidase 1-4, PH-20, and HYALP1. HYAL1 is the major mammalian hyaluronidase in somatic tissues, acting to degrade large molecular weight HA to small tetrasaccharides. The enzyme is lysosomal and exhibits highest activities at acidic pH but still weakly active up to pH 5.9. HYAL1 is also present in human serum and urine, and can act at neutral pH. The importance of HYAL1 clinically is seen in mucopolysaccharidosis type IX where mutations in the HYAL1 gene are associated with accumulation of HA, short stature and multiple periarticular soft tissue masses. The deletion of Hyal1 in the mouse did not alter the CHS response, suggesting this enzyme is not essential for DC function, at least under conditions lacking injury. Even during injury, several other mechanisms could contribute to HA breakdown.

Further, low MW fragments of HA (LMW, 1,350-4,500 Da) are potent inducers of angiogenesis in vitro and in vivo (Lokeshwar et al., 1996; Hirano et al., 1994). Six hyaluronidase genes encode Hyal-1, 2, 3, 4, PHYAL1 (a pseudogene) and PH-20 with high MW HA and its fragments binding hyaladherin proteins including CD44, a major HA receptor (Liu et al., 2002; Ishizawa et al., 2004).

Hyaluronan binds to the hyaladherin family of transmembrane glycoproteins (including CD44) which are expressed in a variety of cells including EC (Singleton et al., 2004; Singleton et al., 2002). Multiple CD44 isoforms result from extensive, alternative exon splicing events (Lokeshwar et al., 1996; Hirano et al., 1994) with the alternative splicing often occurring between exons 5 and 15 leading to a tandem insertion of one or more variant exons (v1-v10, or exons 6 through exons 14 in human cells) within the membrane proximal region of the extracellular domain (Gee et al., 2004; Bourguignon et al., 1998). The variable primary amino acid sequence of different CD44 isoforms is further modified by extensive N- and O-glycosylations and glycosaminoglycan (GAG) additions (Turley et al., 2002; Bourguignon et al., 1998). The extracellular domain of CD44, containing clusters of conserved basic residues, plays an important role in HA binding, whereas the cytoplasmic domain is both structurally and functionally linked to cytoskeletal elements and signaling molecules (Turley et al., 2002; Bourguignon et al., 1998). The signaling properties of CD44 are required for a variety of cellular activities including EC adhesion, proliferation, migration and angiogenesis (Turley et al., 2002; Singleton et al., 2004; Singleton et al., 2002; Bourguignon et al., 1998; Toole et al., 2002). Further, $CD44^{-/-}$ mice develop lung fibrosis, inflammatory cell recruitment and accumulation of hyaluronan fragments at sites of lung injury (Teder et al., 2002).

Hyaluronan can be obtained from rooster comb, human umbilical cord, and bovine organs such as trachea. It is also available commercially from Annika Therapeutics, Inc. (see World Wide Web at fda.gov/cdrh/pdf3/p030019c.pdf), Biomatrix, ICN, and Pharmacia. HA can also been produced using bacterial fermentation, such as with streptococcal bacteria.

The early inflammatory response to tissue injury has been proposed to involve recognition of components of damaged cells by pattern recognition receptors (PRRs) such as Toll-like receptors (TLRs). These dead cell components have been called "damage-associated molecular patterns" (DAMPs) and include intracellular molecules such as the chromatin associated protein high-mobility group box 1 (HMGB1), heat shock proteins (HSPs), purine metabolites, such as ATP, uric acid, DNA, RNA as well as molecules released by extracellular matrix degradation such as heparan sulfate, biglycan, versican and hyaluronan (HA). Currently, several lines of experimental evidence support the important role of PRRs in vitro and in vivo. However, interpretation of the unique function of specific DAMPs has been difficult due to the multiple microbial products that exist in a wound and the potential for small amounts of microbial products to be present in reagents used to study these responses.

HA has been of interest as a DAMP because it is particularly abundant in skin. As mentioned above, large molecular weight HA undergoes breakdown into small fragments after injury. These HA fragments can then interact with endothelial cells, macrophages and dendritic cells (DC), a process thought to be mediated by TLR4 and/or TLR2. The size of HA after breakdown influences its function. Small, tetra-and hexasaccharide fragments of HA are shown to influence DC in culture via TLR4 while larger, 135 KDa fragments initiate alloimmunity.

A local increase of adipocytes occurs below the skin epithelial surface in response to microbes, and the process of adipogenesis regulates microbial invasion through the skin. Adipocytes have also been known to associate with IBD, where the accumulation of mesenteric fat, also known as "creeping fat", and the appearance of the "fat halo sign" within the submucosa of the small intestine, are well-known signs associated with inflammation in Crohn's disease and idiopathic inflammatory bowel diseases (IBD).

Cell migration-inducing and hyaluronan-binding protein (CEMIP), formerly known as KIAA1199, is a protein that in humans is encoded by the CEMIP gene. CEMIP has been shown to bind hyaluronic acid and catalyze its depolymerization independently of CD44 and hyaluronidases.

The disclosure demonstrates the role of HA in allergic reactions and infection. In particular the disclosure demonstrates that HMW-HA induces adipogenesis and AMP production, while HMW-HA degradation or the application of oligo-Has reduces dendritic cell migration and activity which is a cornerstone of allergic reactivity.

The disclosure shows that adipogenesis occurs in the response of inflammation in colon in a manner similar to that observed in the skin. Furthermore, digestion of HA inhibits this response and influences inflammation and barrier function of both skin and intestine. These observations suggest that HA is a previously unappreciated immune modulator that could be exploited for the treatment of IBD or cutaneous inflammatory diseases.

The disclosure demonstrates that digestion of HA by addition of hyaluronidase suppressed adipogenesis both in vitro and in vivo following experimental induction of colitis or deep skin infection. Furthermore, both skin and colon showed a dramatic decrease in inflammation and tissue damage upon addition of hyaluronidase despite an increase in bacterial invasion. These observations suggest that HA controls the response of preadipocytes to injury is a potential therapeutic target for control of inflammatory disorders of the skin and gut.

The biological significance of increased fat accumulation surrounding sites of epithelial injury was previously unknown. Although visceral adipose tissue has long been speculated to be a component of the innate immune system of the gut, and several descriptions of the production "adipokines" from fat such as leptin, adiponectin and cytokines have been reported, the contribution of adipokines to IBD has been controversial.

Moreover, a similar adipogenic phenomenon in the skin can be applied to also understand the significance of adipogenisis in the intestine. In skin, dermal white adipose tissue (DWAT) expands during wound repair and infection. The capacity of these activated preadipocytes to produce antimicrobial peptides is critical to skin defense in mice. The data presented herein show that DSS induced increased expression of genes associated with adipogenesis and that similar to human IBD, an increased accumulation of fat can be seen in mice.

Both skin and intestine have abundant HA in the epithelial and subepithelial layers and this HA rapidly turns over with as much as a third of HA replaced daily. HA accumulation was observed in submucosal layers from samples obtained from human IBD (FIG. 31), and similarly occurred in cultured preadipocytes when triggered to undergo differentiation to adipocytes. Addition of a stable soluble form of hyaluronidase (PEGPH20) that is clinically approved for use during administration of chemotherapy to humans successfully digested HA and suppressed adipogenesis in cultured preadipocytes (FIG. 27). Importantly, injection of PEGPH20also effectively digested HA in the colon of mice (FIG. 28). To validate subsequent interpretations of the consequences of this event an independent technique for digestion of HA by transgenic systemic expression of hyaluronidase 1 was used. The success of both approaches address the potential effects of alternate HA digestion products generated by different enzymes. Furthermore, Pref-1 expression in the colon could be also be inhibited by use of a PPARg inhibitor, thus providing an alternative method to influence adipogenesis that was independent of HA.

The disclosure thus provides in one part the use of oligoHAs and/or enzymes (e.g., hyaluronidase) that degrade large molecular weight HAs to HA fragments to modulate (a) allergic reactions of the skin and gut by reducing inflammatory cells in the region of a potential or actual allergic/inflammatory reaction (b) to modulate inflammation of the skin and/or gut, (c) as an adjuvant to promote sensitization to an antigen/allergen, (d) to inhibit or reduce adipogenesis in the skin and/or gut, (e) to reduce or inhibit adipocyte differentiation, and (f) to inhibit cathelicidin production. In some embodiments the timing and duration of exposure are related to the two processes. For example, to treat an allergic or inflammatory condition of the skin and/or gut oligoHAs and/or an enzyme that breaks down HA are administered either topically, subcutaneously, gastrointestinally, parenterally and the like prior to a potential reaction or during a reaction. The oligoHAs and/or enzyme (e.g., a hyaluronidase) decrease the number of inflammatory cells and/or adipogenesis present in the tissue being treated thereby reducing the number of activated cells that induce or promote an inflammatory or allergic condition. In another embodiment, the timing of the delivery of oligoHAs and/or enzyme can be used to promote sensitization. As demonstrated in the examples below, delivery of oligoHAs causes migration of inflammatory cells away from the site of oligoHA and/or enzyme action. The cells migrate to the lymph nodes and major site of antigen/allergen processing memorization and the like. For example, if the oligoHAs are delivery immediately prior to (e.g., 10, 5, 3, 2 or less minutes), simultaneously with, or immediately after (e.g., within 10 minutes) of delivery of an antigen or allergen, the inflammatory cells are activation and more rapidly delivery the antigen/allergen to the lymph nodes. This increase migration of, for example, activated DC cells to the lymph improves sensitization.

The disclosure provides compositions comprising oligo hyaluronan (oligoHA) and/or an enzyme (e.g., hyaluronidase) that degrades HA to oligoHAs. The methods and compositions of the disclosure can use oligoHAs obtained or derived from any number of sources. In one embodiment, the composition comprises substantially purified di-, tri- and tetrasaccharides of hyaluronan (or mixutures thereof). In a specific embodiment, the disclosure provides a preparation that is 50% or more by weight or by composition of trisaccharides and/or tetrasaccharides of HA. In another embodiment, the disclosure provides a preparation that is 60% or more by weight or by composition of trisaccharides and/or tetrasaccharides of HA. In another embodiment, the disclosure provides a preparation that is 70% or more by weight or by composition of trisaccharides and/or tetrasaccharides of HA. In another embodiment, the disclosure provides a preparation that is 80% or more by weight or by composition of trisaccharides and/or tetrasaccharides of HA. In another embodiment, the disclosure provides a preparation that is 90% or more by weight or by composition of trisaccharides and/or tetrasaccharides of HA. In another embodiment, the disclosure provides a preparation that is 95% or more by weight or by composition of trisaccharides and/or tetrasaccharides of HA. In another embodiment, the disclosure provides a preparation that is 98% or more by weight or by composition of trisaccharides and/or tetrasaccharides of HA. In another embodiment, the disclosure provides a preparation that is 99% or more by weight or by composition of trisaccharides and/or tetrasaccharides of HA.

As mentioned above HA is commercially available. OligoHA can be obtained by digesting or fragmenting HA to a desired size. The preferred size can be isolated/purified using standard protocols including size fractionation, chromatograph, filtration and the like.

Further, the oligoHA of the present disclosure may be in the form of a salt, and may be in an ionized state. Examples of a salt include, for example, salts with an inorganic base such as alkali metal salts (sodium salt, lithium salt, potassium salt etc.), alkaline earth metal salts and ammonium salts and salts with an organic base such as diethanolamine salts, cyclohexylamine salts, amino acid salts, galactosamine salts and glucosamine salts. Among these, alkali metal salts and sodium salts are particularly useful.

A source of the oligoHA of the disclosure is not particularly limited. For example, the oligoHA of the disclosure may be produced by a process comprising separation and purification of HA from chicken crest, umbilical cord, porcine skin, bovine skin, skins or aortas of fish and other animals, microorganisms producing HA and so forth and degradation of HA (e.g., enzymatic degradation, chemical degradation, heat treatment, ultrasonication etc.). The oligoHA may also be produced by a synthetic process (e.g., chemical synthesis and enzymatic synthesis).

Examples of the enzymatic degradation method include methods of allowing an enzyme that degrades HA such as hyaluronidase (derived from testis), hyaluronidase (derived from *Streptomyces*), hyaluronidase SD, chondroitinase ACI, chondroitinase ACIII, chondroitinase ABC and endoglucuronidase (derived from leech) to act on HA. In order to obtain an HA oligosaccharide of the disclosure a hyaluronidase 1 can be used as the enzyme that degrades HA.

Examples of the chemical degradation method include the alkaline decomposition method, dimethyl sulfoxide method (DMSO method) and so forth. The alkaline decomposition method can be specifically performed by, for example, adding a base such as about 1 N sodium hydroxide to a solution of HA, warming the mixture for several hours to degrade HA into those of lower molecular weights and then neutralizing the mixture with addition of an acid such as hydrochloric acid. The hydrolysis can also be carried out by using an acid such as hydrochloric acid and sulfuric acid.

Examples of the ultrasonication method include the method described in Biochem., 33, pp. 6503-6507, 1994 and so forth.

Examples of the synthesis method include the methods described in Glycoconjugate J., pp. 453-439, 1993; International Patent Publication WO93/20827 and so forth.

The oligoHA of the disclosure produced as described above can be purified to a desired purity. It can be purified to such a degree that the oligoHA of the substantially consist of oligoHA of a uniform size.

The HA oligosaccharides purified have a size selected from 2 to 20 saccharides, 2 to 16 saccharides, 2 to 14 saccharides, and typically 4 saccharides.

The form of the fraction of the disclosure for storage, distribution etc. is not particularly limited, and it may be in the form of solution, frozen product, lyophilized product or the like.

Thus, the disclosure provides, in one embodiment, methods and compositions to treat, alleviate and/or inhibit allergic reactions, contact dermatitis, psoriasis, atopic dermatitis, graft vs. host disease and disorders, adipocyte differentiation, adipogenesis, colitis, IBD and other disease and disorders comprising dendritic cell activation.

The method includes contacting or administering a composition comprising an oligoHA and/or an enzyme that produces oligoHA from HA to subject at the site of, or potential site of, an inflammatory or allergic reaction or adipogenesis or adipocyte differentiation. The method includes administering and effective amount of a composition comprising an oligoHA and/or enzyme that degrades HA. In some instances, the composition will result in an inhibition of the production of antimicrobial peptides (AMPS) such as CAMP or other cathelicidins. The composition can be a topical preparation (e.g., a lotion, spray, ointment and the like) that can be applied to the skin at the site of inflammation or potential inflammation. In another aspect, the administering can be through microneedle or subcutaneous injection at the site of, or potential site of, an inflammatory or allergic reaction. The composition can be designed for oral delivery including delayed and/or extend release composition that target the small intestine (e.g., enteric coatings). In any of the foregoing the oligoHA and/or enzyme are typically prepared in a pharmaceutically acceptable carrier for delivery. The contact or administration can be continued for a period of time sufficient for the particular condition. An effective amount of an oligoHA and/or enzyme composition includes that amount sufficient to reduce (a) the number of inflammatory or dendritic cells, (b) the number of adipocytes, (c) the amount of adipogenesis, (d) the amount cathelicidin, or (e) any combination of the foregoing, at the site of contact.

The disclosure is based, in part, on the unexpected discovery that oligoHAs and/or HA-degrading enzymes have an adjuvant or antigen sensitizing function and can modulate adipogenesis.

The disclosure also provides compositions and methods for enhancing an immune response against an antigen in an individual. The composition comprises isolated or purified oligoHA and an antigen. It is important to understand that the two components need not be administered simultaneously but can be administered independently and temporally. Typically, the administration is simultaneous, however, under some methods the two may be administered independently within 1 to several minutes or hour to one another. If the oligoHA is administered first, the antigen or allergen should be administered prior to the oligoHA inducing a depletion of DC cells in the location of contact.

The disclosure demonstrates the action of hyaluronidase, or an increase of small fragments of HA, to inhibit adipogenesis and/or adipocyte differentiation and/or inflammation. The disclosure also demonstrates the action of hyaluronidase, or an increase of small fragments of HA, activate cutaneous DCs and modulates the capacity to induce contact allergy. These observations directly show an important physiologic role for HA breakdown.

The model system shows that HA fragments and HA-degrading enzymes modify the cutaneous and gastrointestinal immune and/or inflammatory response in the absence of the many other variables present following an injury or infection.

The data and results presented in Example 4 below demonstrate the role of the ECM and resident, non-lymphoid cells in the dermis to play an important role in host defense against bacterial infection. Large molecular weight HA is highly abundant and is the major component of the ECM. HA digestion into small fragments after injury has been shown to have important implications to inflammatory responses in vivo and can modify infection by GAS through digestion of the HA-rich bacterial capsule of this organism. The data show that Cemip is responsible for the increase in endogenous hyaluronidase activity seen during deep tissue infection. These observations provide important new insight into the mechanism that function in the dermis to resist infection (e.g. invasive S. aureus infection).

The data show that Cemip digests HA during skin infection. These include observations of increased transcript abundance, increased protein abundance, and decreased large molecular weight HA corresponding to the timing, localization and hyaluronidase activity of Cemip. There was no evidence of an increase in the expression of other hyaluronidases such as Hyal1, Hyal2, Hyal3 and TMEM2. HYAL4 has chondroitinase, not hyaluronidase activity, and expression of PH-20 is restricted to testes. A loss of hyaluronidase activity was apparent in Cemip$^{-/-}$ mice as they did not show the decrease in size of HA after infection that was observed in controls, and had less loss of total large molecular weight HA as measured by staining with HA binding protein or ELISA. It has also been suggested that reactive oxygen species are also involved in HA degradation after tissue injury. Furthermore, S. aureus itself can contribute hyaluronidase activity to the site of infection through expression of HysA, an enzyme secreted by the pathogen and associated with virulence. However, the results presented below show that Cemip is responsible for a major fraction of the local increase in HA breakdown that occurs during S. aureus infection.

Cemip, was originally discovered in dermal fibroblasts. Cemip has also been shown to be induced by histamine, and as histamine in skin is primarily released by mast cells, these cells could contribute to the response observed. Mast cell deficient mice had somewhat less Cemip but were still able to show increased expression after infection (FIG. 41).

The data demonstrate that the most direct explanation for increased resistance to S. aureus in Cemip$^{-/-}$ mice is the increase in Camp produced by the rapid, local differentiation of preadipocyte fibroblasts to mature fat. A persistence of high molecular weight HA enables this adipogenic response and results in much greater expression of Camp in the dermis at the site of infection. The results show that loss of Cemip enables the skin to respond to S. aureus infection by increasing expression of Camp, expanding DWAT and enhancing gene expression associated with adipogenesis.

The data presented in Example 4 show that local induction of hyaluronidase activity has a negative consequence to the host, as it enables greater bacterial proliferation and infection than when Cemip is deleted.

The disclosure also provides a method of treating skin infection (e.g., infection by *S. aureus*). In this method, a subject having, suspected of having or having a site susceptible to infection (e.g., a wound, surgical site) is treated with high molecular weight HA (HMW-HA) or an agent that inhibits enzymes that degrade HA. Such methods and compositions will promote adipogenesis and production of AMPs.

In one embodiment, the disclosure provides a method of treating a skin infection by contacting the skin at the site of infection or injury with a composition comprising HMW-HA. In another or further embodiment, the disclosure comprises contacting the site of infection or injury with a composition that inhibits enzymes that degrade HMW-HA (e.g., such enzymes include hyaluranidases and Cemip). In another or further embodiment, the method includes a composition that promotes adipogenesis and adipocyte maturation (e.g., adiponectin).

The composition for treating infection (e.g., comprising HMW-HA and/or enzymes inhibitors and/or adipogenesis factors) can be a topical preparation (e.g., a lotion, spray, ointment and the like) that can be applied to the skin at the site of an infection, wound, injury or the like. In another embodiment, the administering can be through microneedle or subcutaneous injection at the site of, or potential site of, infection, wound, injury etc.

As used herein the term "isolated" is meant to describe a compound of interest (e.g., either a polynucleotide or a polypeptide) that is in an environment different from that in which the compound might naturally occur. "Purified" as used herein refers to a compound removed from an environment in which it was produced and is at least 60% free, typically at least 75% free, and most commonly 90%-100% free from other components with which it is naturally associated or with which it was otherwise associated with during production.

The phrase "mammalian cell" refers to a cell of any mammal as defined above, with human cells being of interest. The phrase refers to cells in vivo, for example, in an organism or in an organ of an organism. The phrase also refers to cells in vitro, for example, cells maintained in cell culture.

The term "candidate agent" is meant to encompass any agent, including various oligoHA sizes and derivative thereof as well as polypeptides (enzymes) that degrade HA, that can be used in a screening assay for activity in modulating or mimicking a biological activity of interest (e.g., adipogenesis activity, adipocyte differentiation, DC recruitment), and can include any substance, molecule, element, compound, entity, or a combination thereof. The agent can be a natural product, a synthetic compound, or a chemical compound, or a combination of two or more compounds.

"Subject" as used herein is generally a human subject and includes, but is not limited to, a subject showing skin inflammation. The subject may be male or female and may be of any race or ethnicity, including, but not limited to, Caucasian, African-American, African, Asian, Hispanic, Indian, etc. The subject may be of any age, including newborn, neonate, infant, child, adolescent, adult, and geriatric. Subjects may also include animal subjects, particularly mammalian subjects such as canines, felines, bovines, caprines, equines, ovines, porcines, rodents (e.g. rats and mice), lagomorphs, primates (including non-human primates), etc., treated or screened for veterinary medicine or pharmaceutical drug development purposes.

"Treat," "treating" or "treatment" as used herein refer to any type of treatment that imparts a benefit to a patient afflicted with a disease, including improvement in the condition of the patient (e.g., in one or more symptoms), delay in the progression of the disease, reduction in the severity of the disorder or the symptoms of the disorder, the disorder is partially or entirely eliminated, as compared to that which would occur in the absence of treatment, etc. Treatment does not require the achievement of a complete cure of the disorder and can refer to stabilization of disease.

"Effective amount" or "amount effective" as used herein refer to the amount of a therapeutic active agent that when administered or delivered to a subject by an appropriate dose and regimen produces the desired result.

"Pharmaceutically acceptable" as used herein means that the active agent is suitable for administration or delivery to a subject to achieve the treatments described herein, without unduly deleterious side effects in light of the severity of the disease and necessity of the treatment.

Active agents of the disclosure may optionally be administered in conjunction with other compounds useful in the treatment of inflammation or infection (e.g., antibiotics, steroids etc.). The other compounds may optionally be administered concurrently. As used herein, the word "concurrently" means sufficiently close in time to produce a combined effect (that is, concurrently may be simultaneously, or it may be two or more events occurring within a short time period before or after each other, e.g., sequentially). Simultaneous concurrent administration may be carried out by mixing the compounds prior to administration or delivery, or by administering or delivering the compounds at the same point in time but at different anatomic sites and/or by using different routes of administration.

The following examples are provided to further illustrate but not limit the broader disclosure herein.

EXAMPLES

Example 1

To analyze the role of oligoHA in CHS, oligoHA was injected subcutaneously 3 days before DNFB sensitization on the dorsal skin of C57B6 WT mice and measured the increases of ear thickness after elicitation. Increase in ear thickness significantly decreased in oligoHA injected mice, compared with PBS injected mice (FIG. 1*a*). This experiment was repeated with TLR4 deficient mice to examine the involvement of this receptor because it had been previously reported that oligoHA can induce the maturation of DCs via TLR4. The phenotype disappeared in TLR4$^{-/-}$ mice, thus demonstrating the critical role of this receptor in CHS through oligoHA (FIG. 1*b*). To find out the mechanism of action of oligoHA, the number of MHCII positive antigen presenting cells in the epidermis after oligoHA injection was examined. Surprisingly, the number of MHCII positive cells in the epidermis significantly decreased at the site of oligoHA injection (FIG. 1*c, d*).

A 1% oligoHA cream was prepare and applied 3 days before sensitization. This treatment also significantly suppressed CHS response of WT mice 24 hours after eliciatation(Figure 2).

To confirm this effect of small hyaluronan, transgenic mice (Tg) engineered for expression of Hyaluronidase-1 (HYAL1), an enzyme that degrades HA was generated, were generated. Transgenic mice were constructed with a systemically-active promoter containing loxP flanked eGFP reporter gene and stop codon upstream of target gene, HYAL1 (CAG-GFP$^{floxed}$-HYAL1 Tg) (FIG. 3a). Breeding of these GFP-positive transgenic mice with EIIa-cre mice enabled initial production of EIIa-cre/CAG-HYAL1 Tg mice that eliminate the GFP and stop sequence and drive to over-express HYAL1 systemically. Overexpression of the target gene was confirmed by qPCR. To evaluate the enzymatic activity, the size of HA in the skin of these mice was analyzed, which was observed to be constitutively smaller than control mice with a molecular weight less than 30 kDa (FIG. 3b). Histological evaluation of the skin stained with HABP in EIIa-cre/CAG-HYAL1 Tg showed significantly less HA (FIG. 3c). But there were no apparent histological changes in the dermis or epidermis under normal conditions (FIG. 3d). To test the impact of HYAL1 overexpression in the epidermis, mice were generated which overexpress HYAL1 only in epidermal tissues using KRT14-cre mice. The keratin-14 promoter was used to express cre recombinase in the epidermis of KRT14-cre mice. KRT14/CAG-HYAL1 Tg mice lack the expression of GFP in the epidermis, and overexpressed HYAL1 in the epidermis of the mice. Because Termeer et al. had reported that small HA fragments of tetra- and hexasaccharide size induced immunophenotypic maturation of human monocyte-derived DC and mature human DC had a nonadherent phenotype, the number of MHCII positive APCs in the epidermis of transgenic mice was examined. Immunohistochemistry confirmed the significantly reduced number of MHCII positive cells in HYAL1 overexpressing mice (FIG. 3e, f). Furthermore, using flow cytometry, a significant decrease in the number of MHCII and CD11c double positive APCs were observed in epidermis of HYAL1 overexpressing mice (FIG. 3g, h).

Contact hypersensitivity reaction in KRT14/CAG-HYAL1 mice were significantly suppressed compared with that of the control mice (FIG. 4a, b). These findings provide evidence that the overexpression of HYAL1 and HA fragmentation in the epidermis is responsible for the absence of CHS induction in HYAL1 overexpressing mice.

A possible explanation for the suppressed CHS in HYAL1 overexpressing mice to DNFB sensitization is that decreased DC of these mice could lead to impaired ability to migrate and transfer antigen to DLN after antigen application. To test this hypothesis, the shaved abdominal skin of mice were painted with the hapten eFluor670 and 24 hours later examined inguinal DLNs for the presence of CD11c+eFluor670+ cells, which likely represent recent skin DC emigrants. The number of CD11c+eFluor670+ DCs in DLNs of HYAL1 overexpressing mice (KRT14-cre/CAG-HYAL1 Tg mice) was significantly reduced compared with the results of control mice (FIG. 4c, d).

To test the impact of HYAL1 overexpression on the function of the allergen-presenting DC, the initial DNFB painting was replaced with an i.v. injection of lymph node cells from DNFB-painted mice. Injection of lymph node cells from DNFB painted control mice sensitized HYAL1 overexpressing mice (KRT14-cre/CAG-HYAL1 Tg mice) to DNFB (FIG. 4e). In contrast, injection of lymph node cells from DNFB-painted HYAL1 overexpressing mice was not able to sensitize the control mice to DNFB (FIG. 4f). These findings indicate that sensitizastion phase is involved in this phenotype of HYAL1 overexpressing mice.

Termeer et al. had reported that fragmentation product of HA induced maturation of DC via TLR4. To examine the involvement of TLR4 in this phenotype, TLR4$^{-/-}$ were generated; CAG-GFP$^{floxed}$-HYAL1 Tg and TLR4$^{-/-}$; KRT14-cre mice and crossbred them to make TLR4$^{-/-}$; KRT14/CAG-HYAL1 mice and control mice. The number of MHCII positive cells in epidermal sheets of these mice were examined and found no significant differences between TLR4 deficient KRT14-Cre/CAG-HYAL1 Tg mice and TLR4 deficient control mice (KRT14-cre mice) (FIG. 5a, b). FIG. 5c shows that normal ear swelling responses were observed in TLR4 deficient HYAL1 overexpressing mice. These data suggest that HYAL1 expression and endogenous hyaluronan catabolism modulates CHS by affecting DC in the epidermis through TLR4.

These results indicate that HA degraded product have an important role in CHS and provide a therapeutic approach modifying DC function.

Example 2

Chemicals and reagents. Endotoxin free Oligo-hyaluronan (HYA-OLIGO4EF-5) was purchased from Hyalose. HA preparations were free of DNA and protein contamination as preparations showed no absorbance at 260 nm and 280 nm. Human umbilical cord HA and DNFB (2,4-dinitrofluorobnezene) were purchased from Sigma-Aldrich. Biotin-labeled hyaluronic acid binding protein was purchased from Associate of Cape Cod. Antibodies to MHC class II (M5/144.15.2), CD11c (N418), and CD80 (16-10A1) were obtained from eBiosciences. Antibodies to CD103 (2E7) and CD11b (M1/70) were obtained from Biolegend. An antibody to CD207/Langerin (929F3.01) was obtained from Dendritics. The human HYAL1 antibody (ab85375) was obtained from AbCam. Topical HA fragments were compounded in VANICREAM (Pharmaceutical Specialties). Tamoxifen was purchased from MP Biomedicals.

Animals. The plasmid for the targeted overexpression of HYAL 1 was constructed based on the strategies employing the vector, pCFE. Details of the pCFE plasmid are described below (see, also FIG. 13A). The essential elements of the pCFE expression construct are the CAG promoter driving the expression of a floxed eGFP gene that is followed by a second gene of interest. This construct is flanked by 2 sets of 1.2 kb chicken beta globin insulator regions that act to decrease the influence of local chromatin structure and regulatory elements on the expression construct. The LoxP sites allow Cre mediated excision of eGFP and its stop codon enabling the CAG promoter to then drive expression of the downstream target gene in a tissue specific manner. For assembly of the HYAL1 construct, the full-length human HYAL1 cDNA was amplified from dermal microvascular endothelial cells with forward and reverse primers. The primers contain Not I and Pme I restriction sites, respectively. The amplified product was subcloned by digestion with Not I and Pme I and inserted into pCFE. The correct sequence and orientation of inserts were verified by enzyme digestion and sequencing. Pvu I and Sal I-linearized targeting vector DNA was microinjected into the pronucleus of a fertilized ovum (C57B16) at the UCSD Transgenic mouse core. These microinjected embryos were reimplanted into the oviduct of pseudopregnant female recipients and they gave birth 20 days after implantation. Founders were identified both by PCR and by monitoring eGFP fluorescence. EIIa-Cre (003724), KRT14-Cre (004782), KRT14-Cre/ERT (005107) transgenic mice and TLR4 deficient mice (007227) were obtained from the Jackson Laboratory. KRT14-Cre mice were backcrossed for more than 6 generations with C57Bl/6J mice in the laboratory for use in subsequent studies. These transgenic mice were crossbred to generate EIIa-Cre or KRT14-Cre/CAG-HYAL1 Tg mice (EIIa/HYAL1 or K14/HYAL1) in which HYAL 1 is overexpressed and litter mate controls (CAG-GFP, EIIa-Cre or K14-Cre alone). Offspring were genotyped by PCR using genomic DNA isolated from the tails. All experiments used sex- and age- matched littermates. All animals were housed in barrier conditions in the vivarium of the School of Medicine of the University of California San Diego that were approved by the Association for Assessment and Accreditation of Laboratory Animal Care. Mice were weaned at 3 weeks, maintained on a 12-hour light-dark cycle and were fed water and standard rodent chow.

Preparation of Plasmid. The plasmid for the targeted overexpression of HYAL1 was constructed based on the strategies employing the vector, pCFE. The pCFE plasmid was derived from plasmid pJC13-1, pCET5, and pcDNA3.1 (Invitrogen). Plasmid pJC13-1 contains copies of a 1.2 kb 5' end of the chicken β-globin locus that has been shown to function as an insulator by both blocking external enhancer function and through a barrier mechanism. In pJC13-1 there are 2 copies of the 1.2 kb insulators upstream and downstream of a γ-neo reporter gene. The enhancer and γ-neo reporter gene were removed from pJC13-1 by consecutive digestions and re-ligations following digestion with EcoRI and then BamHI to generate pJC13-3-AC-modified. The CMV promoter was removed from pcDNA3.1(+) by SpeI digestion followed by re-ligation. Primers sense 5'-GTGGTCTAGAGCTCGGTACCAAGC (SEQ ID NO:1) and antisense 5'-CCCTCTAGAGCCA-GATCTGGTTCTTTCCGCCTCAG (SEQ ID NO:2) were used for PCR of pcDNA3.1 (−) to amplify the BGH-polyadenylation site with flanking XbaI restriction sites and generate an additional BglII restriction site. This PCR fragment was digested with XbaI and inserted into XbaI digested pcDNA3.1 (+)-S9(-CMV promoter). Plasmid pCET5 was digested with SpeI to liberate a fragment containing the CAG promoter (CMV early enhancer/β-actin promoter) driving the expression of loxP flanked EGFP/CAT and was then inserted into the SpeI site of pcDNA3.1 (+)-S9 (-CMV promoter+BGH polyA site). The resulting plasmid was digested with BglII to excise a fragment containing CAG-loxP-EGFP/CAT-loxP-S9-BGHpolyA that was ligated into the BamHI site between the flanking insulator of pJC13-3-AC-modified to generate pCFE-S9. S9 was removed by digestion with PmeI and NotI to generate pCFE allowing insertion of HYAL1. The essential elements of the pCFE expression construct are the CAG promoter (CMV enhancer-beta-actin promoter) driving the expression of a floxed eGFP gene that is followed by a second gene of interest. This construct is flanked by 2 sets of 1.2 kb chicken beta globin insulator regions that act to decrease the influence of local chromatin structure and regulatory elements on the expression construct. The LoxP sites allow Cre mediated excision of eGFP and its stop codon enabling the CAG promoter to then drive expression of the downstream target gene in a tissue specific manner.

Anatomical and histological analysis. Tissues embedded in paraffin were sectioned and stained with hematoxylin/eosin. Anatomical and histological survey of organs and tissues such as brain, heart and circulatory system, lungs, gastrointestinal tract, genito-urinary tract, hematopoietic system, and the endocrine system of transgenic mice (5 males and 5 females for each group) were examined at the UCSD Murine Histology Core for initial screening.

HA staining of mice skin. To determine if HA accumulates in the skin of transgenic mice, these mice were euthanized, and an 8-mm punch biopsy was used to remove a section of full-thickness skin. Skin was embedded in OCT compound and frozen at −20° C. Sections (7 μm thick) were cut, and staining was carried out according to the protocol using biotinylated-hyaluronic acid-binding protein and Fluorescein isothiocyanate-streptoavidin obtained from Jackson ImmunoResearch. Fluorescence staining was imaged using an Olympus BX41 fluorescent microscope (Scientific Instrument Company).

GAG release from skin. Murine skin was homogenized and treated overnight with protease (0.16 mg/ml; Sigma) to degrade protein, followed by purification by anion exchange chromatography using DEAE sephacel (Amersham Biosciences). Columns were washed with a low salt buffer (0.15 M NaCl in 20 mM Sodium acetate; pH 6.0) and eluted with 2 M NaCl. Glycans were desalted by PD10 (GE healthcare). Uronic acid concentration was determined by carbazole assay.

Determination of HA size by agarose gel electrophoresis. The size distribution of HA was analyzed by agarose gel electrophoresis. The HA sample was mixed with TAE buffer containing 2 M sucrose and electrophoresed at 2 V/cm for 10 h at room temperature. The gel was stained overnight under light-protective cover at room temperature in a solution containing 0.005% Stains-All in 50% ethanol, and destained in water. Hyalose ladders (Hyalose) were used for standards.

Immunization and induction of CHS. Sex- and age-matched adult transgenic mice (8-12 weeks) were anesthetized by isoflurane inhalation, and hair was removed on the dorsal skin by shaving followed by manual depilation. For induction of CHS, the mice were painted with 0.5% DNFB or vehicle (acetone/olive oil=3/1) on the shaved dorsal skin for sensitization, followed by epicutaneous application of 0.15% DNFB on the dorsum of the ears of the mice on day 5 for elicitation. Ear measurements were done before and 24 and 48 h after ear challenge using an engineer's micrometer (Mitutoyo).

Adoptive CHS. Adoptive CHS was induced as previously described. Mice of the various donor strains were sensitized by painting the shaved abdominal skin and both ears with 2% DNFB. Auricular, axillary, maxillary, and superficial inguinal lymph nodes were harvested 5 days later. Single cell suspensions were prepared and $2 \times 10^7$ lymph node cells were injected i.v. into naive recipient mice. Thickness of both ears of the recipients was measured 24 hours after adoptive cell transfer before painting with 0.15% DNFB and the swelling was measured 24 hours after painting.

Immunohistochemistry and immunofluorescence. Epidermal sheets were prepared by shaving mouse abdominal skin followed by affixing them to slides (epidermis side down) with double sided adhesive (3M). For the topical induction of Cre recombinase, 200 μl of 4 mg/ml tamoxifen in acetone:DMSO (9:1) was applied once daily on the shaved dorsal skin for 3 days. Slides were incubated in 0.5 M Ammonium thiocyanate for 2 hr at 37° C. followed by physical removal of the dermis. Tissues were fixed in acetone at 4° C. for 10 min and blocked with 3% BSA in PBS. Tissues were then stained with an MHC class II or CD80 antibody followed by an anti-rat IgG antibody conjugated with rhodamine (Santa Cruz biotechnology) or anti-hamster IgG antibody conjugated with FITC (eBioscience).

In vivo assay for migration of skin DCs. The abdominal skin of individual mice was shaved followed by application of 100 μl of 100 μg/ml eFluor670 (65-0840-90, eBioscience) or FITC dissolved in 1:1 acetone/dibutylphthalate (Sigma-Aldrich) or acetone alone. At 24 hours, inguinal LNs were isolated by digestion at 37° C. with 0.1% DNase I (MP Biomedicals) and 1 mg/ml collagenase D (Roche). Single cell suspensions were incubated with Fc-block (FcgRII/III mAb 2.4G2) for 15 mins and stained with antibodies to CD11c, MHC class II. Stained cells were washed and the percentage of CD11c+eFluor670+ cell in the DLNs was evaluated by FACS at the VA San Diego Research FACS core facility.

Analysis of epidermal cells. Preparation of epidermal sheets and single cell suspensions were performed as described previously. Briefly, epidermal sheets were incubated on 0.3% Trypsin/GNK solution with 0.1% DNase at 37° C. for 20 minutes and filtered. After centrifuge at 1500 rpm for 10 mins at 4° C., the cell pellet was resuspended and rested for 12 hours in DMEM complete media. Single cell suspensions were stained with Abs for MHC class II and CD11c, followed by FACS analysis.

Analysis of dermal cells. Single cell preparations from the dermis were prepared as previously described. Briefly, the epidermis was digested with 0.3% trypsin for 120 min and removed from the dermis. The dermis was further digested with collagenase XI and hyaluronidase (both from Sigma Aldrich) for 120 min followed by FACS analysis.

Determination of mRNA expression by quantitative RT-PCR. Real time PCR was used to determine the mRNA abundance as described previously. TaqMan™ Gene Expression Assays (Applied Biosystems) were used to analyze the expression of HYAL1 and Il-10. Gapdh mRNA was used as an internal control. HYAL1 mRNA expression was calculated as relative expression compared to Gapdh mRNA, and all data are presented as normalized data compared to each control (mean of control tissues).

ELISA and Lunimex. Cytokines and chemokines in mouse skin were measured using Luminex kits (Millipore) according to the manufacture's instruction. MIP-2 ELISA Duo set (R&D Systems) was used to measure mouse Cxcl2/Mip-2 in mouse skin. Normal dorsal skins were isolated with 6-mm punch biopsy from the euthanized mice. The skin sections were placed in tube with 500 µl 1× radioimmune precipitation assay buffer (50 mM HEPES, 150 mM NaCl, 0.05% SDS, 0.25% deoxycholate, 0.5% Nonidet P-40, pH 7.4) with protease inhibitor mixture (Complete™ EDTA-free, Roche) and were beaten with 2.4-mm zirconia beads by a mini-beadbeater apparatus (Biospec Products, Inc.) for 50 s on full speed. Extracts were then sonicated for 5 min in ice-cold water and spun down at 12,000×g for 10 min. Supernatant was harvested and kept at −20° C. until analysis.

Statistics. Statistical analysis was performed by using a 2-tailed Student's t test or one-way analysis of variance with Prism software (version 5; GraphPad Software). Results are expressed as mean±SEM. P value less than 0.05 were considered significant.

Study approval. All animal procedures performed in this study were reviewed and approved by the University of California San Diego Institutional Animal Care and Use Committee. The experiments were conducted in accordance with the NIH guidelines for care and use of animals and the recommendations of International Association for the Study of Pain.

Generation of HYAL1 overexpressing mice. To study the role of HA breakdown in vivo, transgenic mice (Tg) were engineered for conditional expression of human hyaluronidase1 (HYAL1), termed CAG-GFPfloxed-HYAL1 Tg (CAG-GFP) (FIG. 6A). Breeding with EIIa-Cre mice was done for systemic expression during early development (EIIa/HYAL1), breeding with KRT14-Cre mice (K14/HYAL1) was done for constitutive conditional overexpression in the basal epidermis, and inducible epidermal expression was done by tamoxifin application to CAG-GFPfloxed-HYAL1 Tg crossed with KRT14-CreERT mice (K14CreERT/HYAL1). As expected, decreased eGFP fluorescence was observed in EIIa/HYAL1 mice systemically expressing Cre (FIG. 6B), indicating that the reporter gene and stop codon had been excised. The specificity of K14 promoter was confirmed by the loss of GFP in the epidermis (FIG. 14). Expression of the target gene was also confirmed by quantifying the abundance of human HYAL1 mRNA by qPCR (FIG. 6C). Protein expression of HYAL1 in K14/HYAL1 mice was confirmed by immunostaining (FIG. 6D).

The function of HYAL1 to degrade HA was confirmed by observing a loss of staining for large molecular weight (MW) HA in the skin using an HA binding protein that binds large HA (FIG. 6E). Furthermore, analysis of the size of HA extracted from the skin of HYAL1 overexpressing mice confirmed this observation by showing loss of detectable large molecular weight HA above 27 kDa and a subsequent increase in abundance of smaller HA between 27 and 0.5 kDa (FIG. 6F). These correspond in size to HA oligosaccharides from small tetrasaccharides to linear HA fragments containing approximately 68 disaccharide units.

Figure 15:
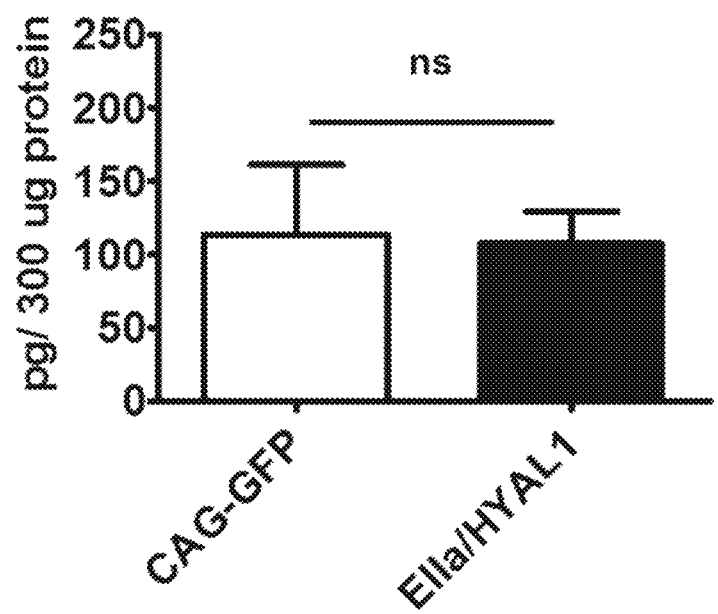
FIG. 15 shows Mip-2 in normal skin of EIIa/HYAL1 mice was measured by ELISA. n=6 per group, Mean±SEM. n.s.: not significant. Data are representative of two independent experiments.
Figure 16:
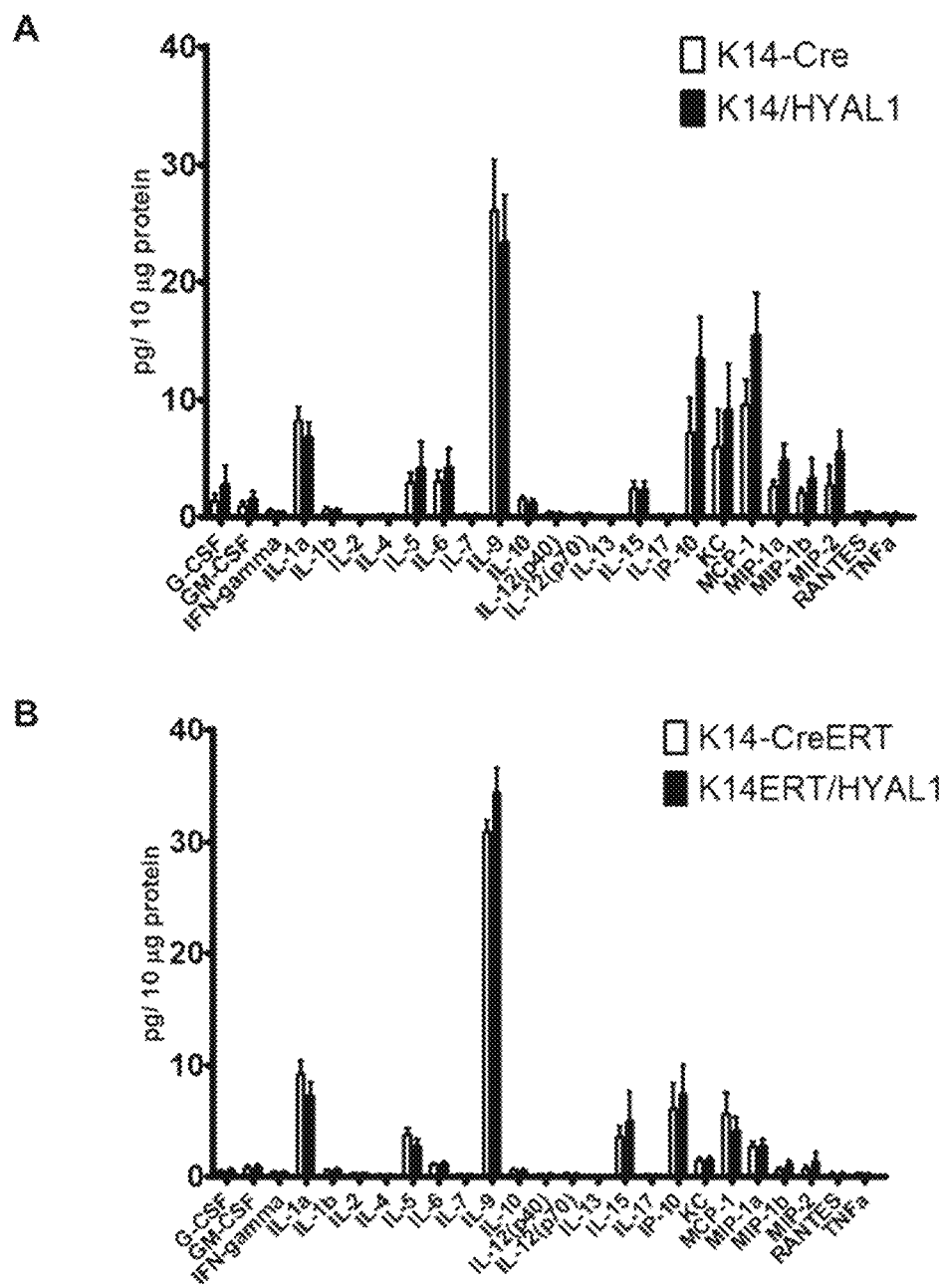
FIG. 16A-B shows cytokines and chemokines in normal skin of (A) K14/HYAL1 and (B) K14ERT/HYAL1 mice were measured by Luminex kits. n=6 per group, Mean±SEM. Data are representative of two independent experiments.

There was no evidence of spontaneous inflammation and no other apparent histological changes in the skin of mice constitutively overexpressing HYAL1 (FIG. 6G). Previous reports have identified CXC chemokine release such as macrophage inflammatory protein-2 (Mip-2) as a rapid and sensitive indicator of a response to HA in vitro. Constitutive embryonic hyaluronidase expression induced no difference in Mip2 protein in the skin (FIG. 15). Additionally, a panel of 24 other cytokines and chemokines were measured in skin of K14/HYAL1 and K14CreERT/HYAL1 by Luminex and observed that there was no difference when compared with the controls (FIG. 16, A and B). There were also no significant differences in mRNA expression of Il-10 in the skin or lymph nodes after HYAL1 expression (FIG. 17). Furthermore, no systemic morphologic abnormalities were detected by 12 weeks of age in EIIa/HYAL1 compared to control groups after anatomical and histological survey of the brain, heart, circulatory system, lungs, gastrointestinal tract, genito-urinary tract, hematopoietic system, or endocrine tissues (data not shown). No laboratory abnormalities were detected by hematologic survey including complete blood count, blood chemistry, coagulation and the bleeding time except for the slight but significant increase in LDL of EIIa/HYAL1 mice serum (P=0.011) (Table 1). Thus, in contrast to prior measurements of the response to HA fragments in vitro, the degradation of HA in vivo did not initiate an apparent inflammatory response.

TABLE 1

Results of hematology, coagulation, blood Chemistry and lipid panel of EIIa/HYAL1 mice and EIIa-Cre mice. Data are representative of two independent experiments.

|  | EIIa Cre | | EIIa/HYAL1 | |
| --- | --- | --- | --- | --- |
|  | Mean | S.D. | Mean | S.D. |
| HEMATOLOGY | n = 12 | | n = 9 | |
| WBC (K/µL) | 9.23 | 1.74 | 9.28 | 1.88 |
| Neutrophils (%) | 15.45 | 5.38 | 13.79 | 2.86 |
| Neutrophils (K/µL) | 1.46 | 0.71 | 1.30 | 0.42 |
| Lymphocytes (%) | 81.39 | 5.41 | 82.76 | 2.98 |
| Lymphocytes (K/µL) | 7.49 | 1.32 | 7.66 | 1.49 |
| Monocytes (%) | 2.18 | 0.69 | 2.81 | 0.72 |
| Monocytes (K/µL) | 0.23 | 0.05 | 0.26 | 0.07 |
| Eosinophils (%) | 0.47 | 0.48 | 0.52 | 0.47 |
| Eosinophils (K/µL) | 0.04 | 0.05 | 0.05 | 0.05 |
| Basophils (%) | 0.11 | 0.17 | 0.11 | 0.17 |
| Basophils (K/µL) | 0.01 | 0.02 | 0.01 | 0.02 |

TABLE 1-continued

Results of hematology, coagulation, blood Chemistry and lipid panel of EIIa/HYAL1 mice and EIIa-Cre mice. Data are representative of two independent experiments.

| | | | | |
|---|---|---|---|---|
| RBC (M/µL) | 8.86 | 0.28 | 8.83 | 0.47 |
| HGB (g/dL) | 14.8 | 1.5 | 15.2 | 1.7 |
| HCT (%) | 38.6 | 1.3 | 38.7 | 2.1 |
| MCV (fL) | 43.5 | 0.5 | 43.4 | 0.6 |
| MCH (pg) | 16.7 | 1.5 | 17.0 | 1.7 |
| MCHC (g/dL) | 38.3 | 3.1 | 38.1 | 3.7 |
| RDW (%) | 19.3 | 0.5 | 19.3 | 0.4 |
| PLT (K/µL) | 745 | 74 | 769 | 65 |
| MPV (fL) | 4.85 | 0.13 | 4.90 | 0.11 |
| COAGULATION | n = 9 | | n = 8 | |
| PT (s) | 10.5 | 0.3 | 10.6 | 0.4 |
| APTT (s) | 24.9 | 2.0 | 23.6 | 2.7 |
| Antithrombin (% BIS pool) | 71 | 14 | 76 | 15 |
| Protein C (% BIS pool) | 165 | 43 | 154 | 59 |
| Protein S (% BIS pool) | 118 | 20 | 117 | 18 |
| Plasminogen (% BIS pool) | 120 | 16 | 124 | 20 |
| Alpha-2 antiplasmin (% BIS pool) | 105 | 8 | 111 | 8 |
| | n = 12 | | n = 9 | |
| Bleeding Time (s) | 126 | 184 | 97 | 49 |
| CHEMISTRY | n = 12 | | n = 9 | |
| Glucose (mg/dL) | 167.3 | 31.7 | 172.4 | 38.1 |
| Urea nitrogen (mg/dL) | 20.0 | 2.4 | 20.8 | 1.9 |
| Creatinine (mg/dL) | 0.1 | <0.1 | 0.1 | <0.1 |
| Bicarbonate (mEq/L) | 13.4 | 2.1 | 12.6 | 2.1 |
| Chlorine (mEq/L) | 106.3 | 2.6 | 107.0 | 2.1 |
| Sodium (mEq/L) | 153.0 | 4.5 | 151.6 | 1.0 |
| Potassium (mEq/L) | 5.6 | 0.4 | 5.7 | 0.5 |
| Calcium (mg/dL) | 9.5 | 0.2 | 9.4 | 0.2 |
| Direct bilirubin (mg/dL) | | | | |
| Total bilirubin (mg/dL) | 0.1 | 0.0 | 0.1 | 0.0 |
| Albumin (g/dL) | 3.6 | 0.3 | 3.7 | 0.3 |
| Total protein (g/dL) | 5.1 | 0.2 | 5.1 | 0.2 |
| Phosphorus (mg/dL) | | | | |
| AST (SGOT) (IU/L) | 58.0 | 13.7 | 53.0 | 12.0 |
| ALT (SGPT) (IU/L) | 38.8 | 16.3 | 29.1 | 3.4 |
| Alkaline phos. total (IU/L) | 89.8 | 20.4 | 99.0 | 21.2 |
| LIPID PANEL | n = 12 | | n = 9 | |
| Lipase (U/L) | | | | |
| Cholesterol (mg/dL) | 94.9 | 9.5 | 100.7 | 11.0 |
| HDL-chol. (mg/dL) | 74.2 | 8.5 | 79.1 | 9.1 |
| LDL-chol. (mg/dL, calculated) | 6.9 | 1.8 | 9.2 | 2.0 |
| Triglycerides (mg/dL) | 90.1 | 21.5 | 80.1 | 14.5 |

HYAL1 expression or HA tetrasaccharides induce loss of dendritic cells from the skin. The number of MHC class II positive dendritic cells were examined in the epidermis of constitutive HYAL1 overexpressing mice. Analysis by flow cytometry demonstrated a significant decrease in the number of MHC class II and CD11c double positive cells in the epidermis of K14/HYAL1 mice (FIGS. 7A and B). The reduced numbers of MHC class II positive cells in the epidermis of K14/HYAL1 mice were confirmed by immunohistochemistry (FIG. 7C). These results indicated that the number of Langerhans cells (LCs) in the epidermis of K14/HYAL1 mice was decreased.

Similar to the response seen in the epidermis, the total number of MHC class II+, CD11c+double positive dermal DCs were significantly decreased in the dermis of HYAL1 overexpressing K14/HYAL1 mice (FIG. 7D). Furthermore, the total numbers of Langerin+, MHC class II+, CD11c+ dermal DCs were also significantly lower in HYAL1 over-expressing mice compared to control mice (FIGS. 7E). In particular, HYAL1 overexpression resulted in decreased numbers of Langerin+MHC class II+/CD11c+/CD103−/CD11b+ DCs in the dermis (FIG. 7F). However, there was no difference in the frequency of Langerin negative, CD103 and CD11b+, MHC class II+, CD11c+ cells in the dermis (FIG. 7G).

To examine the dynamic nature of epidermal and dermal DC response to expression of HYAL1, the skin in the tamoxifen-inducible K14-dependent Cre system was then evaluated. HYAL1 mRNA in the skin increased significantly 48 hours after tamoxifen application (FIG. 18). The number of the MHC class II+ cells in the epidermis of K14CreERT/HYAL1 mice was identical to controls before tamoxifen application, but coincident with the timing of expression of HYAL1, DCs started to decrease 48 hours after tamoxifen (FIGS. 8A and B). There was no evidence of DC apoptosis after HYAL1 expression as detected by the expression of active caspase-3. However, the loss of DC was accompanied by the expression of CD80, a marker of DC maturation (FIG. 8C). To determine if the loss of DCs from the skin was due to accelerated migration, the effect of HYAL1 on the migration of DC to regional lymph nodes was evaluated. HYAL1 expression was induced by topical application of tamoxifen for 2 days and painted the same site with the hapten eFluor670 and examined inguinal draining lymph nodes (DLNs) 24 hours later. The presence of CD11c+eFluor670+ cells was examined in inguinal draining lymph nodes (DLNs). HYAL1 overexpressing mice significantly increased the number of CD11c+eFluor670+ DCs in DLNs compared to control mice treated with the tamoxifen vehicle (acetone/DMSO) and eFluor670 (FIGS. 10D and E). Furthermore, the frequency of total CD11c+ cells in the inguinal lymph nodes was significantly increased after tamoxifen-dependent HYAL1 overexpression (FIGS. 10F and G). Thus, the loss of DCs from the skin and coincident increase of DC in the regional lymph nodes, support the conclusion that HYAL1 expression enhanced the migration of DC from the skin. This conclusion was also supported by the direct demonstration of increased cells in the lymph node that were labeled with eFluor670, and an increase of the DC maturation marker CD80 that is associated with increased migration.

To distinguish between effects on DCs coming from the generation of HA fragments or the loss of large MW HA, and further confirm the capacity of HA to affect DC function, purified low molecular weight HA tetrasaccharides (oligoHA) were injected into the skin of wild-type mice. Injection of oligoHA recapitulated all of the responses seen after HYAL1 overexpression. The number of MHC class II positive cells in the epidermis significantly decreased at the site of oligoHA injection in a time dependent manner (FIG. 9A). This decrease in MHC class II positive DCs coincided with an increase in CD80+ cells (FIGS. 9B and C). The frequency of CD11c cells that were labeled on the skin surface with FITC increased in DLNs of oligoHA-injected mice compared to PBS-injected control mice (FIG. 9D). Taken together, these data further support the conclusion that the production of HA fragments by HYAL1 initiates DC maturation and migration out of the skin.

HYAL1 expression and HA tetrasaccharides influence allergic sensitization. To determine the physiological significance of the effects of HA digestion its role in the development of contact hypersensitivity (CHS), a function attributed in part to langerin+ dermal DCs, was studied. Consistent with the depletion of DC in their skin, mice that constitutively express HYAL1 in the epidermis (K14/HYAL1) had a large decrease in the CHS response to the topical application of the powerful antigenic hapten DNFB (FIGS. 10A and B). Mice expressing HYAL1 systemically (EIIa/HYAL1) showed a similar decreased CHS response (FIGS. 19A and B). These mice also demonstrated a significantly reduced capacity to deliver eFluor670 hapten to the DNL when compared to control mice (FIGS. 10C and D and FIG. 20). However, no difference in the abundance of CD4+CD25+ regulatory T cells was detected in the thymus and lymph nodes and no evidence for a change in skin barrier function of HYAL1 overexpressing mice (EIIa/HYAL1) was seen as evaluated by trans-epidermal water loss (TEWL) measurements (data not shown). These data show that the depletion of DC by constitutive HYAL1 expression is functionally important, resulting in greatly decreased CHS response. Of note, the normal endogenous expression of mouse Hyal1 did not influence CHS response under these conditions as no difference was observed when Hyal1−/− mice were compared to controls (FIG. 21)

Next, to determine if the lack of CHS influenced by HYAL1 expression was due to decreased sensitization phase or abnormal elicitation phase, this response was examined after adoptive LN transfer. Transfer of DLN cells from control mice sensitized with DNFB to HYAL1 overexpressing mice restored the CHS response despite the expression of HYAL1 during elicitation (FIG. 10E and FIG. 22A). In contrast, transfer of DLN cells from DNFB-sensitized HYAL1 overexpressing mice as donor to control WT mice did not result in an inflammatory response to DNFB (FIG. 10F and FIG. 22B). These data support the conclusion that the decreased DC number inhibited CHS through diminished capacity to sensitize against the allergen.

Since the administration of HA tetrasaccharides were shown in FIG. 9 to also deplete DC from the skin, experiments were performed to determine if this would also deplete the CHS response. A significant decrease in CHS was observed when oligoHA were injected at the site 3 days before sensitization (FIG. 10G). The topical application of oligoHA in an oil-in-water emulsion cream base also led to CHS suppression if administered 3 days before sensitization. Furthermore, local, conditional induction of HYAL1 expression had a similar effect if done before DNFB exposure. When tamoxifen was applied to K14CreERT/HYAL1 mice seven days before application of DNFB the CHS response was significantly suppressed (FIG. 23). These findings showed that when expression of HYAL1, or application HA oligos, took place before antigen exposure, then the preceding loss of DCs resulted in an inability to initiate allergic sensitization.

In contrast to the design of the experiments shown in FIG. 10, an approach was designed to induce HYAL1 just before and during sensitization, but before depletion of DC from the skin. Under these conditions it was hypothesized that the activation of DC migration might accelerate the rate of allergic sensitization. K14CreERT/HYAL1 mice were treated with tamoxifen immediately before sensitization of the same site with DNFB. Tamoxifin-treated K14CreERT/HYAL1 mice had a greatly increased CHS response if elicitation was measured only 1.5 days after sensitization (FIGS. 11A and B), a time when control mice have not yet developed the capacity to respond to the antigen. If elicitation was tested 5 days after sensitization, control mice demonstrated the expected CHS response although HYAL1 expressing mice continued to show a slightly enhanced elicitation reaction (FIG. 24). Injection of oligoHA during sensitization also recapitulated the acceleration effect (FIGS. 11C and D). These observations are consistent with findings that HYAL1 overexpression stimulates DC migration from the skin and shows that this effect can speed the time it takes to effectively induce allergic sensitization.

Function of HYAL1 or HA tetrasaccharides is dependent on TLR4. To determine the mechanism by which HYAL1 expression induced skin DC maturation and modulated CHS sensitization, the role of TLR4 was evaluated. Expression of HYAL1 in a TLR4−/− background prevented mice from responding to HYAL1 since in the absence of TLR4, no decrease in the abundance of epidermal or dermal DC populations was detectable despite breakdown of HA (FIG. 12A and FIG. 25). OligoHA injections also did not alter the migration of cutaneous DCs into DLNs after FITC application in TLR4−/− mice (FIG. 12B). Furthermore, mice were rescued from the suppression of CHS if HYAL1 was constitutively expressed in a TLR4−/− background (FIG. 12C). OligoHA injections also had no effect on either suppression or acceleration of sensitization when they were performed in TLR4−/− mice (FIGS. 12D and E). In contrast, breeding of HYAL1 overexpressing mice to a CD44$^{-/-}$ background did not rescue them from suppression of CHS.

Example 3

Chemicals and reagents. PEGPH20was provided by Halozyme (San Diego, Calif.). Dextran Sulfate Sodium Salt (DSS) was purchased from Mp Biomedicals Inc. Rabbit anti-CAMP antibodies were made from in lab; Rabbit anti-PREF1/DLK antibodies are from Abcam (Cambridge, Mass.); BODIPY® FL dye was purchased from Thermo Fisher(Houston, Tex.). HA binding protein was purchased from Millipore. Human-Hyal1, mouse-Hyal1, Hyal2, KIAA1199, TMEM2, HAS1, HAS2, HAS3, EBF1, ZFP521, ZFP423, Pref1, PPARg, Adipoq, CEBPA, CAMP, IL6, TNF Taqman gene expression assay were purchased from Life Technologies Corporation (Grand Island, N.Y.).

Animals and animal care. Transgenic mice for conditional overexpression of human hyaluronidase-1 (in C57BL/6 background) were generated in the laboratory by combining a constitutive promoter and a loxP-flanked GFP reporter upstream of hyaluronidase-1 (CAG-loxP-GFPstop-loxP-Hya1). Cross-breeding with E2a-Cre mice (EIIa/HYAL1 Mice) for early embryonic expression of Cre enabled the promoter to drive the expression of the downstream hyaluronidase gene. Wild-type mice (C57BL/6 mice) were obtained from The Jackson Laboratory. All animal experiments were approved by the University of California, San Diego, Institutional Animal Care and Use committee. For all animal studies, animals were randomly selected without formal pre-randomization and quantitative measurements were done without the opportunity for bias.

Bacterial strains. S. aureus strain USA30037 is a predominant community-associated Methicillin resistant Staphylococcus aureus (MRSA) strain and was kindly provided by Victor Nizet(Skaggs School of Pharmacy and pharmaceutical Sciences, University of California, San Diego, Calif.).

Mouse model of S. aureus skin infection. Staphylococcus aureus strain USA300/MRSA was used for infection. Briefly, the backs of sex-matched and age-matched adult wildtype or EIla/Hyal1 mice were shaved and hair removed by chemical depilation (Nair) then injected subcutaneously with 100 μl of a mid-logarithmic growth phase of S. aureus ($2\times10^6$ CFU of bacteria) in PBS. Mice were sacrificed after day 3 and 8 mm skin punch biopsy comprising the center of the injection site was harvested. Infected skin surrounding the infection center (6~8 mm) avoid of center abscess was carefully dissected out for RNA extraction or CFU determination. Skin biopsies were homogenized in 1 ml Trizol (for RNA) or PBS (for CFU counting) with 2 mm zirconia beads in a mini-bead beater 16 (Biospect, Bartlesville, Okla.). To count CFU, homogenized skin samples were serially diluted, plated onto Tryptic Soy Agar, and enumerated after 18 hours to quantify the CFU per gram of tissue. For some experiments, PEGPH20(10 mg/kg) was injected intravenously starting from 1 day prior to infection, and vehicle (10 mmol/L histidine, 130 mmol/L NaCl at pH 6.5) was used as control.

Mouse model of DSS colitis. WT or Ella/hyal1 mice provided 3% DSS in their drinking water for 7 days and body weight measured every day. For HA digestion by PEGPH20, Mice were intravenously injected PEGPH20 (10 mg/kg) every 3 days 24 hour prior to start DSS water feeding. For Adipogenesis inhibition by PPARg inhibitor, Mice were intraperitonealy injected 120 mg/kg every single day 48 hour prior to start DSS water feeding. Mice were sacrificed after 5 and 7 days. Distal colon, mesenteric fat and blood were collected for RNA, Bacterial culture assay and toxin analysis.

Preadipocyte culture. The preadipocyte cell line 3T3-L1 was purchased from ATCC (CL-173) lot 59239597. 3T3-L1 cells were grown in preadipocyte proliferation medium stock (Cell applications, San Diego, Calif.), and P4~P7 cells were used for in vitro differentiation. To induce differentiation, two days post-confluent 3T3-L1 cells were switched to adipocyte differentiation medium containing insulin, dexamethasone, and IBMX. (Cell applications, San Diego, Calif.), and medium was changed to fresh medium at day 2 and 4. To generate differentiated adipocytes for comparison studies between 3T3-L1 preadipocytes and adipocytes, 3T3-L1 cells were differentiated for 3 days followed by two days culture in Preadipocyte growth media. (Cell applications, San Diego, Calif.) before RNA or protein extraction.

Reverse transcription-quantitative PCR (RTqPCR) analyses. RTqPCR was used to determine the mRNA abundance. Total cellular RNA was extracted using the PureLink RNA Mini Kit(Life Technologies Corporation, Grand Island, N.Y.) and mRNA were purified by using Dynabeads mRNA Purification Kit(Life technologies). 100 ng of mRNA was reverse transcribed to cDNA using iScript cDNA synthesis kit (BIO-RAD LABORATORIES, INC, Hercules, Calif.). Quantitative, real-time PCR was performed on the CFX96 real time system (Biorad) using predeveloped Taqman gene expression assay (Applied Biosystems). The expression of βActin gene was used as a house keeping gene to normalize data.

Histology and immunohistochemistry (IHC). Tissue biopsies were directly embedded in OCT compound or paraffin. Paraffin embedded tissues are used for Hematoxylin/Eosin (H&E) staining, and frozen sections were fixed in 4% PFA for 20 mins or 100% Aceton prior to immunofluorescence staining. For IHC, fixed and permeabilized tissue sections were blocked with Image-iT FX reagent (invitrogen) before incubating with primary antibodies followed by appropriate 488- or 568-coupled secondary antibodies. Nuclei were counterstained with DAPI. All images were taken with an Olympus BX41 microscope (widefield) or Zeiss LSM510 confocal microscope as indicated.

Flow cytometry analyses. Colon collected from control or DSS-treated mice was cut into small pieces then digested with 2.5 mg/mL Collagenase D and 30 ng/mL DNAse1 for 2 hours at 37° C. then filtered through a 30 μm filter to generate single cell suspension for FACS analyses. Cells were then stained with zombie violet viability dye (BioLegend, 423114), blocked with anti-mouse CD16/32 (eBioscience, 14016185), followed by staining with antibody cocktails for preadipocytes or immune cells. The antibody cocktail for preadipocytes includes AF488-SMA (eBioscience, 53976082), PECy7-CD45 (BioLegend, 147704), PerCy5.5-CD31 (BioLegend, 102522), PE-Thyl (BioLegend, 105308), APC-PDGFRa (eBioscience, 17140181), BV605-SCA1 (BioLegend, 108133) and AF700-CD24 (BioLegend, 108136). The antibody cocktail for immune cells includes PECy7-CD11b (BioLegend, 101216), FITC-Ly6G (eBioscience, 11593182), PE-F4/80 (eBioscience, 12480182), APC-CD11C (BioLegend, 117310), AF700-MHCII (eBioscience, 56532182) and APC-Cy7-CD3 (BioLegend, 100222). FACS analyses for surface expression of preadipocyte or immune cell markers were performed by the BD FACSCanto RUO machine and analyzed by FlowJo V10 software. Dead cells stained positive with zombie violet dye were excluded from the analyses.

Serum Endotoxin analyses. Mouse serum was separated from mouse whole blood using serum separator tubes (Becton, Dickinson and Company). Mouse serum Endotoxin levels were quantified by ToxinSensor Chromogenic LAL Endotoxin Assay Kit (GenScript).

Hyaluronan (HA) analysis. Glucosaminoglycan (GAG) including HA were extracted from 3T3L1 supernatant and Murine skin and colon. Samples were homogenized and treated overnight with protease (0.16 mg/ml; Sigma-Aldrich) to degrade protein, followed by purification by anion exchange chromatography using DEAE sephacel (Amersham Biosciences). Columns were washed with a low-salt buffer (0.15 M NaCl in 20 mM sodium acetate; pH 6.0) and eluted with 1 M NaCl. Glycans were desalted by PD10 (GE Healthcare). HA concentration were measured ELISA Duo Set (R&D Systems). The size distribution of HA was analyzed by agarose gel electrophoresis 41. The HA sample was mixed with TAE buffer containing 2 M sucrose and electrophoresed at 2 V/cm for 10 hours at room temperature. The gel was stained overnight under light-protective cover at room temperature in a solution containing 0.005% Stains-All in 50% ethanol, and destained in water. Hyalose ladders (Hyalose) were used for standards.

Statistics. Experiments were repeated at least three times with similar results. Statistical significance was determined using Student's unpaired two-tailed t test, or one-way ANOVA multiple comparison test as indicated in the legend ($*p<0.05$, $p<0.01$, $*p<0.001$).

Figure 26B:
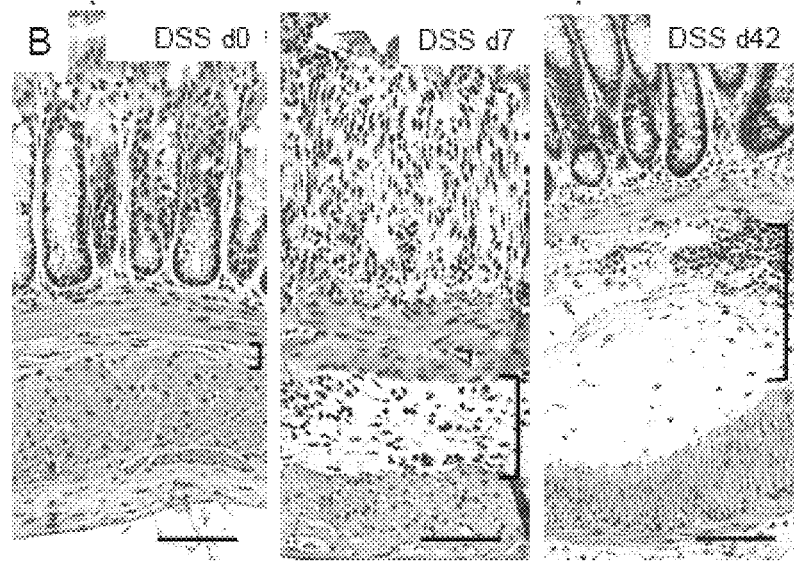
Figure 26C:
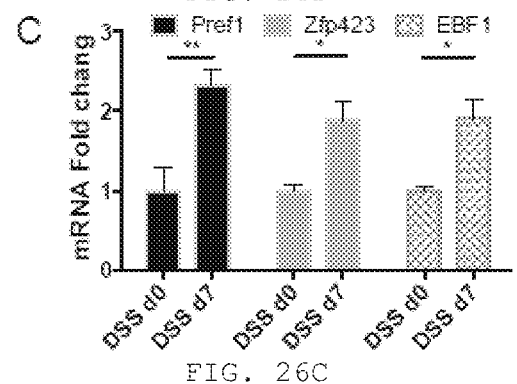
Figure 26D:
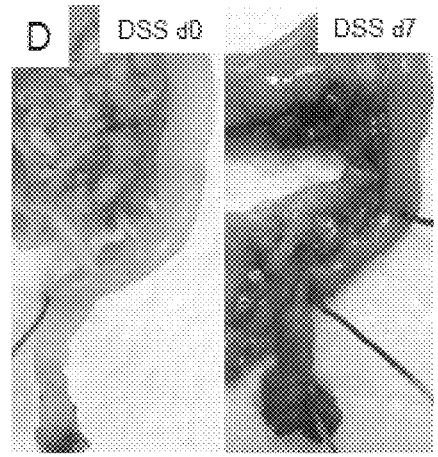
Figure 26E:
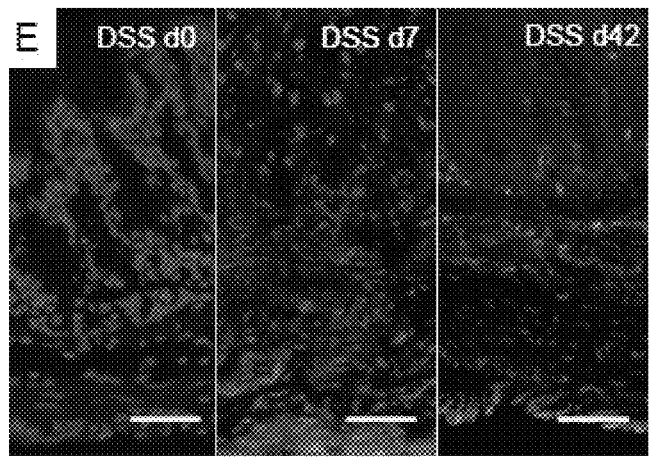
Figure 26F:
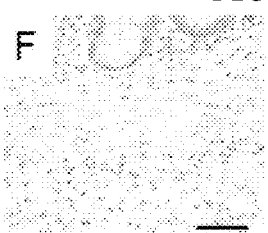
Figure 26G:
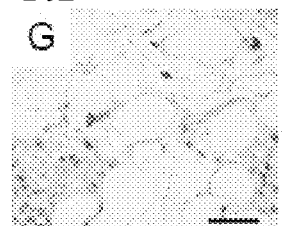

Adipogenesis is associated with colitis. To evaluate if a localized adipogenic response can be induced in an experimental model of colitis, acute colitis was induced in mice through oral administration of 3% dextran sulfate (DSS). Increased accumulation of mesenteric fat was observed 7 days after induction of colitis by DSS (FIG. 26A). Histological evaluation revealed prominent thickening of the submucosal layer, inflammation, epithelial disruption, and accumulation of mature adipocytes at day 42 (FIG. 26B). DSS colitis induced the expression of genes associated with adipogenesis including: preadipocyte factor 1 (Pref-1), Zinc finger protein 423(Zfp423) and Early B cell factor 1(Ebf1) (FIG. 26C). Activation of Zfp423 during the colitis was confirmed by visualizing β-Gal staining of colon and vesicle fat from Zfp423LacZ reporter mice (FIG. 26D). Immunoshistochemistry confirmed expression of Pref-1 occurred within cells in the thickened submucosal layer (FIG. 26E). An increase in the expression of Pref-1 was also observed in human colitis, with prominent staining of Pref-1 observed in cells in the submucosal layer of involved tissues from subjects with Crohn's disease and Ulcerative colitis (FIG.

26F, G). Taken together, these results show that preadipocytes within the submucosal layer of the colon, are activated in response to injury.

Figure 27A:
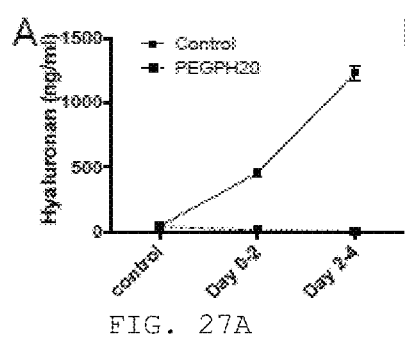
FIG. 27A-G shows adipogenesis is accompanied by increased HA in culture and inhibited by hyaluronidase. Mouse preadipocytes (3T3L1) were differentiated by the addition of adipocyte differentiation media with or without the addition of 20 ug/ml of recombinant hyaluronidase (PEGPH20). (A) HA concentrations in 3T3L1 supernatant over time after addition of differentiation media with and without PEGPH20 (n=6). (B) Expression of Adipoq mRNA as an indicator of differentiation under culture conditions identical to (A). (C) Lipid staining of 3T3L1 cells using Bodipy on the day2 of differentiation with or without PEGPH20 (n=5). Scale Bar=50 Microns. (D to G) Relative expression of mRNA for Zfp521, Pref1, C/EBP α and Camp expression during differentiation. The difference of adipogenes expression between each group at day 2. mRNA expression were measured by RTqPCR and normalized to that of internal control b-actin. All error bars indicate mean±SEM; * P<0.05**, P<0.01 (t test).
Figure 27B:
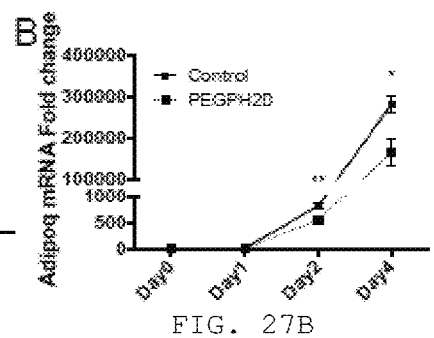
Figure 27C:
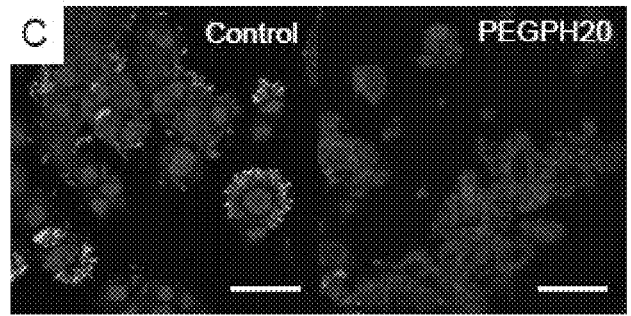
Figure 27D:
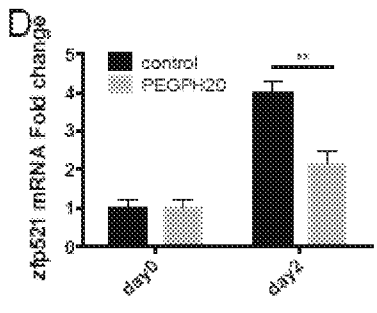
Figure 27E:
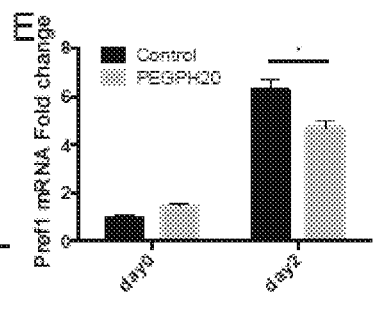
Figure 27F:
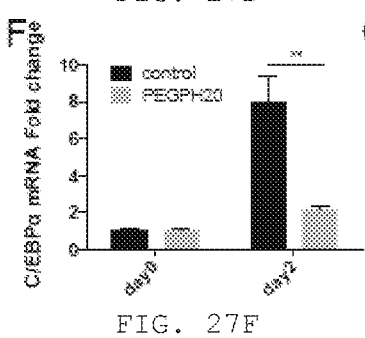
Figure 27G:
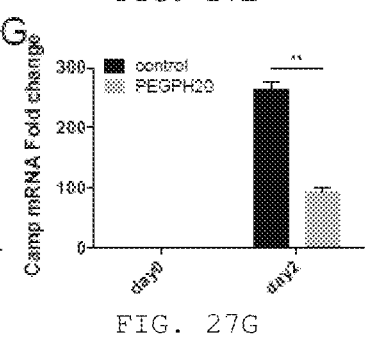

In vitro adipogenesis is inhibited by hyaluronidase. Hyaluronan (HA) has been shown to be important to fat accumulation in mice fed a high-fat diet. Coincident with the increase in adipocytes observed in FIG. 26, abundant HA accumulation was also observed in sections from human colitis (FIG. 31). To study if HA was necessary for adipogenesis observed in colitis, the role of HA was first evaluated during in vitro adipogenesis. A large increase in HA was observed in the culture supernatant the mouse preadipocyte cell line (3T3L1) during differentiation to mature adipocytes (FIG. 27A), and this HA could be removed by addition of PEGylated recombinant human hyaluronidase (PEGPH20) (FIGS. 27 and 32). This digestion of HA suppressed adipogenesis in vitro as seen by decreased expression of the adipocyte differentiation marker adiponectin (Adipoq), (FIG. 27B), lesser accumulation of lipid droplets within cells (FIG. 27C), and lower expression of multiple transcripts that increase during adipocyte differentiation including Zfp521, Pref-1, CCAAT/Enhancer Binding Protein Alpha (C/EBPα) (FIG. 27D-F) Furthermore, the antimicrobial peptide cathelicidin (Camp) was decreased with addition of hyaluronidase (FIG. 27G). These results suggested that hyaluronidase inhibits adipocyte differentiation in vitro.

Figure 28A:
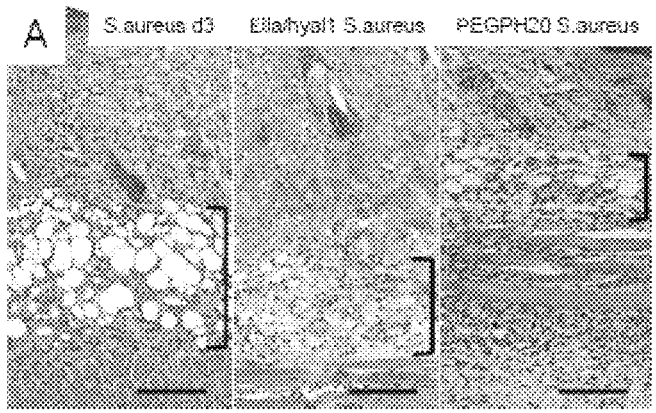
FIG. 28A-F shows in vivo reactive adipogenesis response is inhibited by hyaluronidase (A, B) Representative histology of skin sections from infected area of WT, Ella/hyal1 and PEGPH20 injected mice were stained with H&E or Bodipy. (C) Total RNA was extracted and purified mRNA. CEBPA mRNA expression was measured by quantitative real time PCR and normalized to that of internal control b-actin (n=6 mice/group). (D) Flow cytometry analysis of colon lamina propia single cell suspensions showing expression of PEGFRα and SCA1 from DSS d0 control, DSS d7 control and PEGPH20 treated DSS d7 mice. Cells were gated on CD31-negative, CD45-negative. Numbers represent the percentage of the cells in the indicated gate. (E) Total RNA was extracted and purified mRNA. Pref1 mRNA expression was measured by quantitative real time PCR and normalized to that of internal control b-actin (n=4 control or BADGE and PEGPH20 or 6 Ella/Hyal1 mice/group). (F) Representative clinical and histology of distal colon sections from control, Ella/hyal1 and PEGPH20 injected mice at the 7 days after being provided with 3% DSS colitis in drinking water. Tissue was stained with anti-PREF1/DLK antibodies. Brackets delineate submucosal region occupied by adipocytes. Scale Bar=50 Microns. All error bars indicate mean±SEM; P<0.01, *P<0.001 (t test).
Figure 28B:
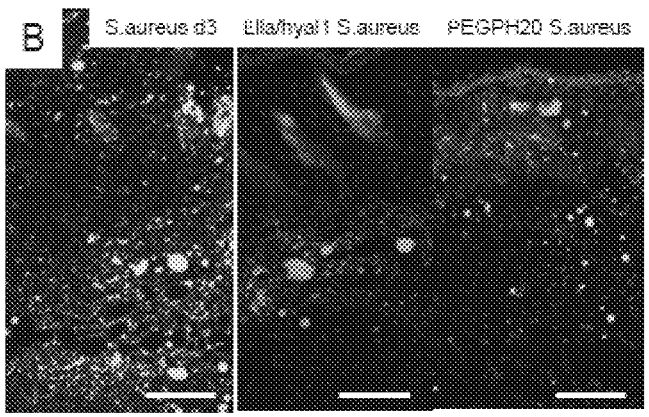
Figure 28C:
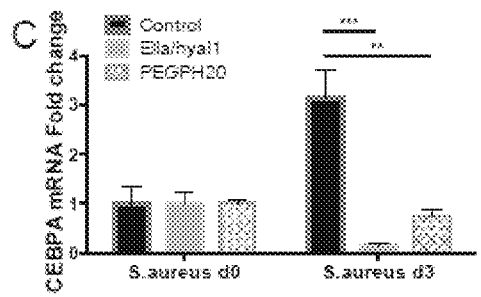
Figure 28D:
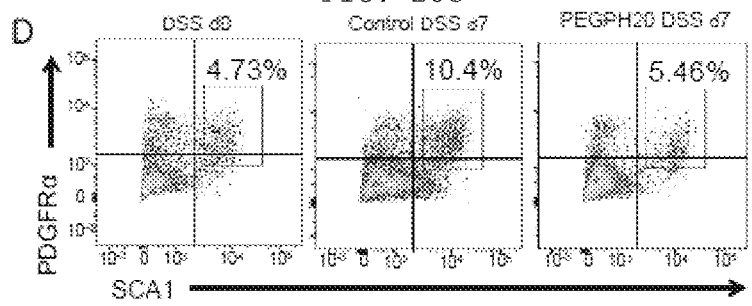
Figure 28E:
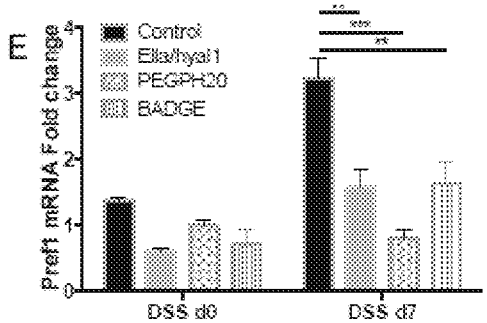
Figure 28F:
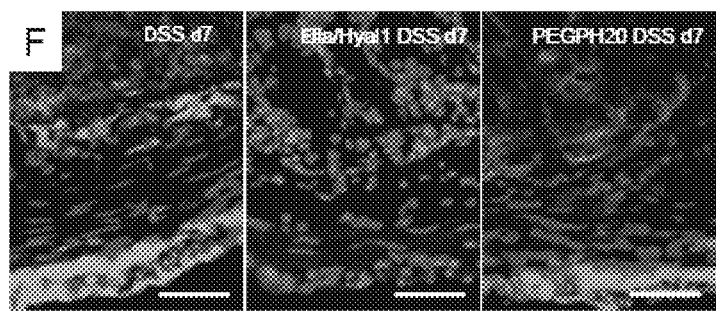
Figure 33A:
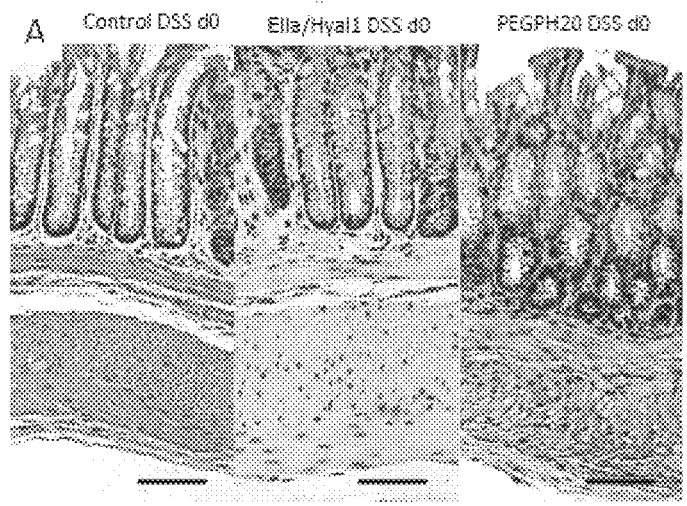
FIG. 33A-B shows (A,B) Representative histology of distal colon sections in colitis of WT, Ella/hyal1 and PEGPH20 injected mice were stained with H&E and HABP. Scale Bar=50 Microns.
Figure 33B:
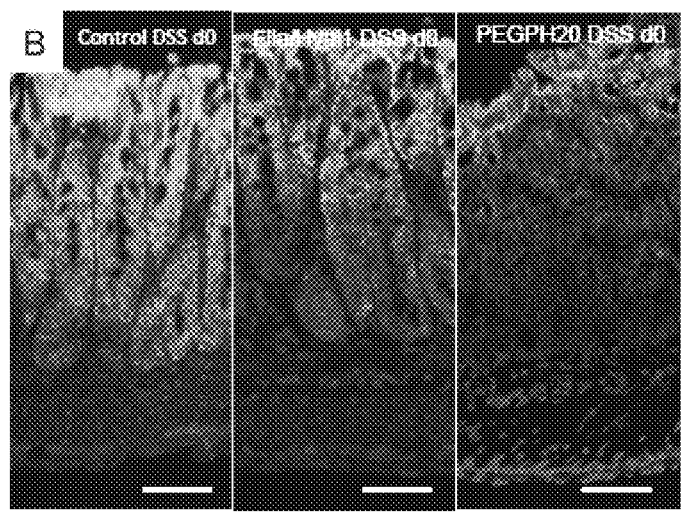

Reactive adipogenesis is inhibited by hyaluronidase. To evaluate if hyaluronidase will also inhibit the response of preadipocytes in vivo in the skin and colon, 2 independent methods for in vivo delivery of hyaluronidase were used; a transgenetic model for over-expression of human hyaluronidase 1 (Ella/Hyal1), and a pharmacologic model by injection of PEGPH20. Both methods of delivery of hyaluronidase successfully reduced HA in mouse tissues (FIG. 33). Increased hyaluronidase inhibited expansion of dermal white adipose tissue (DWAT) during *S. aureus* infection of skin (FIG. 28A), decreased lipid droplet staining (FIG. 28B) and inhibited expression of C/EBPα (FIG. 28C). A similar effect from hyaluronidase was observed in the colon after exposure to 3% DSS. The population of preadipocytes that are CD31-negative, CD45-negative, Platelet-derived growth factor receptor-α (PDGFRα) positive and *Spinocerebellar ataxia* type 1 (SCA1) positive was inhibited by hyaluronidase (FIG. 28D). Furthermore, markers of adipogenesis Pref-1 mRNA (FIG. 28E) and Pref-1 staining (FIG. 28F) was inhibited by hyaluronidase. This capacity of hyaluronidase to inhibit these markers of adipogenesis was similar to the effect of the PPARgamma agonist Bisphenol A diglycidyl ether (BADGE), a commonly used method for direct inhibition of adipogenesis. Taken together, these observations demonstrated that digestion of HA suppressed the increase in adipocytes that occurs in response to inflammation of the intestine and skin.

Epithelial inflammation is inhibited by hyaluronidase. The production of adipokines and antimicrobial peptides by adipocytes has been hypothesized to be important to promoting inflammation and protecting against infection. Furthermore, hyaluronidase delivery to mouse skin has shown the potent capacity to inhibit allergic sensitization and subsequent inflammation. Therefore, given the observation that hyaluronidase can both directly modulate the immune response, and potentially influence inflammation due to an indirect capacity to inhibit adipogenesis, experiments were performed to examine the effectiveness of hyaluronidase as an anti-inflammatory in both skin and colon.

Figure 29A:
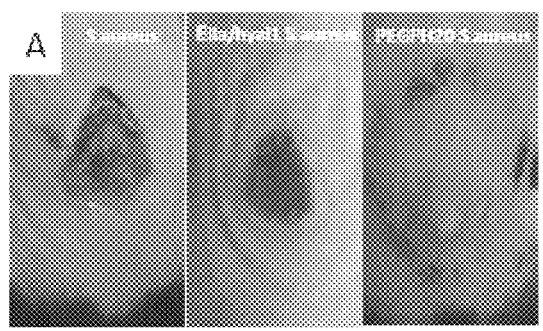
FIG. 29A-D shows skin inflammation response is inhibited by hyaluronidase (A) Infected skin lesion area in WT, hHyal1 overexpressing and PEGPH20injected mice. (B,C) Total RNA was extracted and purified mRNA. IL-6 and Camp mRNA expression in infected skin samples (n=6 mice/group). (D) Systemic bacteremia detected 3 days after S. aureus skin injection in skin isolated from WT and Ella/hyal1 mice (n=4 mice/group). All error bars indicate mean±SEM; P<0.01, *P<0.001 (t test).
Figure 29B:
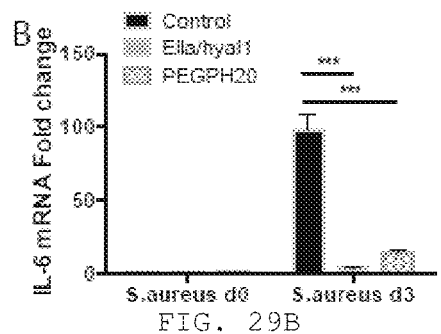
Figure 29C:
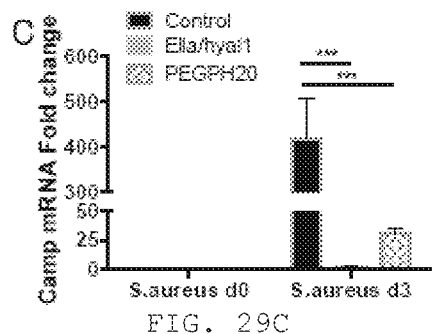
Figure 29D:
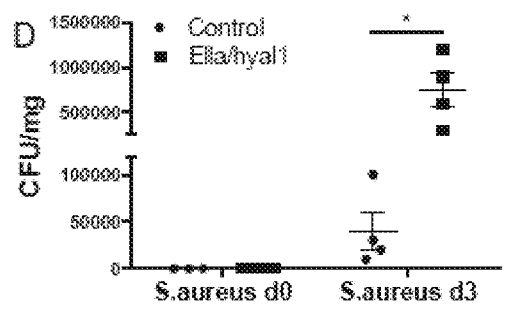

In the skin infection model, hyaluronidase decreased lesion size, expression of IL-6 and expression of Camp in response to *S. aureus* (FIG. 29A-C). Consistent with an anti-inflammatory action and capacity to inhibit antimicrobial peptide-associated adipogenesis, hyaluronidase also promoted an increase in the abundance of *S. aureus* in the lesion (FIG. 29D).

Figure 30A:
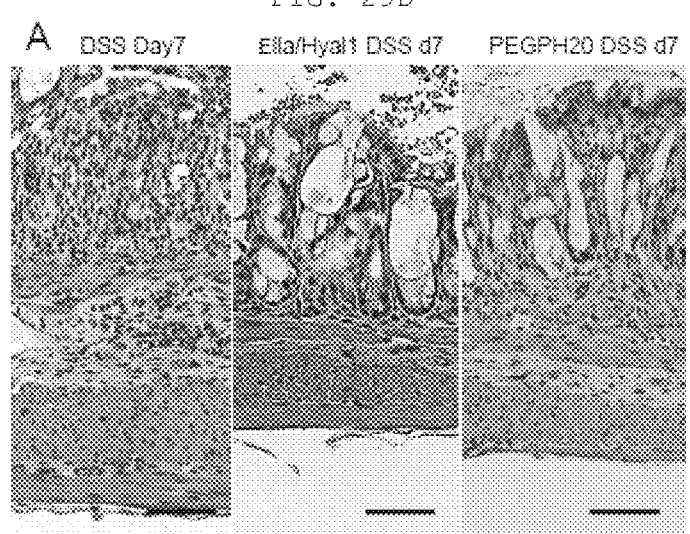
Figure 34A:
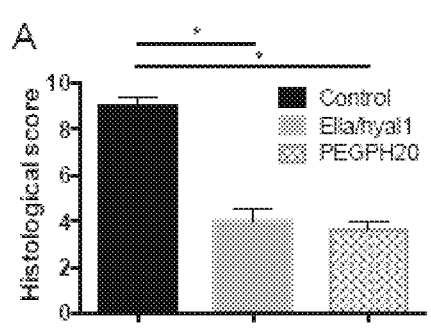
FIG. 34A-D shows (A) Representative histology of distal colon sections in colitis of WT, Ella/hyal1 and PEGPH20 injected mice were stained with H&E. The histological score of day 7 samples were measured by the disease activity index. (B) H&E staining from control and PEGPH20 treatment day 42 samples. (C,D) Flow cytometry analysis of colon lamina propria single cell suspensions showing expression of F4/80 and CD11B and CD11C and MHC II from DSS d0 control, DSS d7 control and PEGPH20 treated DSS d7 mice. Numbers represent the percentage of the cells in the indicated gate. Scale Bar=50 Microns. All error bars indicate mean±SEM; P<0.01, *P<0.001 (t test).
Figure 34B:
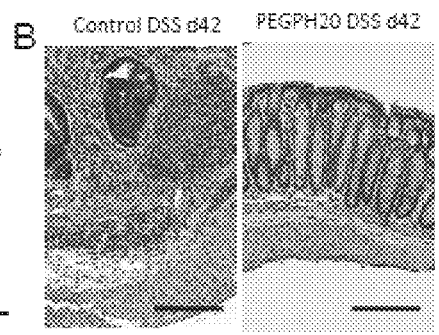
Figure 34C:
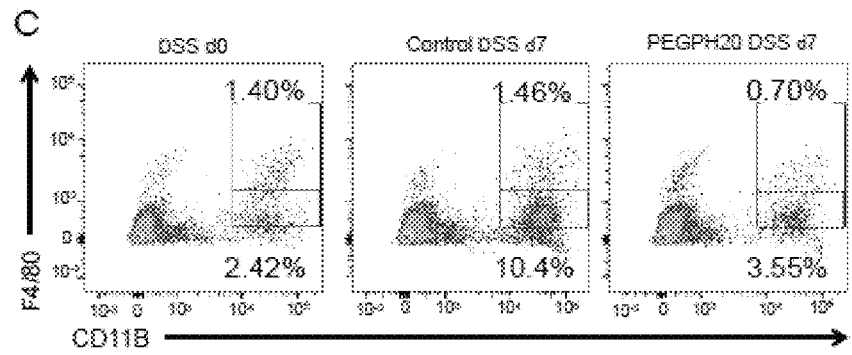
Figure 34D:
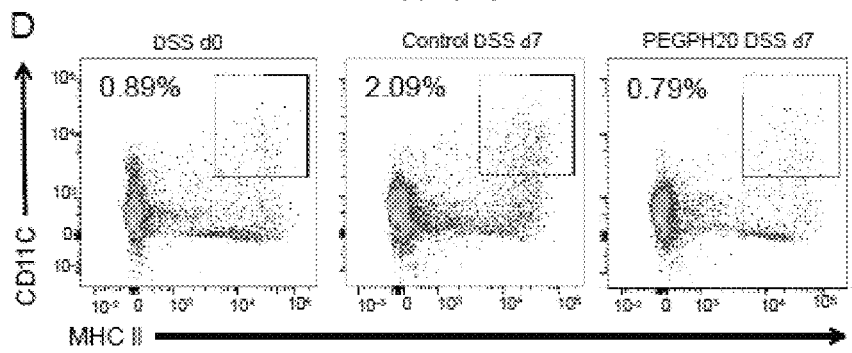

A reduction in inflammation was also observed in the colon after addition of hyaluronidase. Hyal1 mice or mice given PEGPH20 with DSS-induced colitis had less inflammatory infiltrate and submucosal expansion than control mice (FIG. 30A and FIG. 34A-B). Clinical evidence of colitis was reduced by hyaluronidase as seen by a lesser decrease in body weight by day 5 (FIG. 30B). Mice exposed to either model of hyaluronidase delivery also showed lesser expression of tumor necrosis factor alpha (TNFα) than the control colitis group (FIG. 30C) and administration of PEGPH20 resulted in less infiltration of LY6G positive neutrophils in the lamina propia (FIG. 30D), as well as lesser accumulation of Macrophages and Dendritic cells (FIG. 34). Furthermore, similar to the observations of increased *S. aureus* in the skin model, hylauronidase also increased endotoxin and bacteria detected in sera (FIG. 30E-G).

Figure 35A:
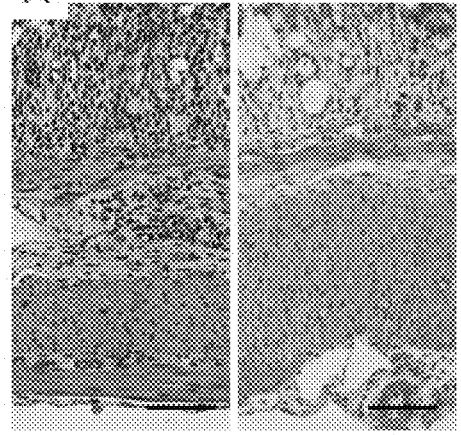
FIG. 35A-C shows (A) Representative histology of distal colon sections in colitis of WT and BADGE treated mice were stained with H&E. (B) TNF and IL6 as inflammation markers mRNA expression in colon samples. (N=4 control and BADGE mice/group).(C) Systemic bacteremia detected after colitis in mesenteric fat and spleen from WT and with BADGE treatment (N=4 mice/group). All error bars indicate mean±SEM; *P<0.05, P<0.01, *P<0.001 (t test).
Figure 35B:
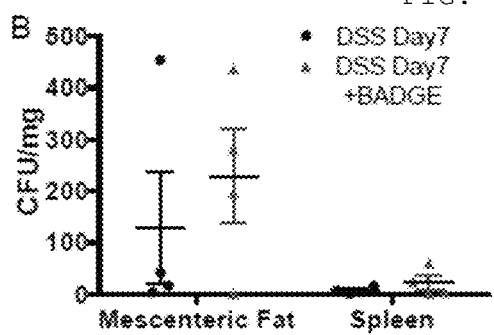
Figure 35C:
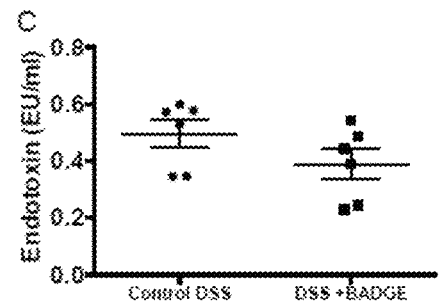

Inhibition of adipogenesis by a hyaluronidase-independent mechanism was also examined by administration of the PPARg inhibitor BADGE. This inhibited expression of TNFα (FIG. 30C) but had a lesser effect than hyaluronidase on preventing DSS induced colon injury as assessed by effects on colon length, histology and microbial translocation (FIG. 35). Taken together these findings show that targeting adipogenesis through administration of hyaluronidase can suppress inflammation in either the skin or intestine.

No effect to the health or behavior of mice was seen following the administration of hyaluronidase to control mice in this study or in prior studies with chronic transgenic administration of Hyal1. However, both approaches to the administration of hyaluronidase resulted in a significant decrease in the gross inflammatory response of the skin to infection (FIG. 29) and colon to DSS (FIG. 30). Consistent with these observations, hyaluronidase decreased expression of IL-6 and TNFa and decreased inflammatory cell infiltration. Although inhibiting adipogenesis by administration of BADGE confirmed the contribution of adipogenesis to inflammation of the colon, the magnitude of this inhibition was less that that seen following administration of hyaluronidase. This suggests that either inhibition of PPARg may have alternative effects that also promote inflammation or that the alternative immunomodulatory actions of HA may combine with its role in the inhibition of adipogenesis to protect against tissue injury.

These observations show that hyaluronidase has potential to be an alternative or adjunctive anti-inflammatory agent. These findings also further advance the role of adipocytes in host defense by demonstrating that in addition to an important role for DWAT in protection against invasive skin infections, preadipocytes in the submucosa of the colon likely also have a similar defense role. Observations of increased serum endotoxin and bacterial translocation following DSS and hyaluronidase administration are consistent with inhibition of antimicrobial peptide expression but may also reflect the overall anti-inflammatory effect. Maintaining a balance between adequate host defense and tissue injury is essential for effectively treating inflammatory diseases. This study illustrates commonalities in inflammatory events at the skin and colon as well as providing preclinical evidence of a novel therapeutic approach.

Example 4

Animals and animal care. Cemip (KIAA1199) KO mice were generated using a gene targeting Cre-loxP system as described in the other report(Shimoda et al., 2017; Yoshino et al., 2017). Wildtype mice (C57BL/6 mice) and K14-cre transgenic mice were obtained from The Jackson Laboratory. K14-cre transgenic mice were bred with Scf$^{fl/fl}$ mice for the generation of K14-cre Scf$^{fl/fl}$ mice. K14-cre littermate controls were used in all experiments. All animal experiments were approved by the University of California, San Diego, Institutional Animal Care and Use committee. For all animal studies, animals were randomly selected without formal pre-randomization and quantitative measurements were done without the opportunity for bias.

Bacterial strains. S. aureus strain USA300 is a predominant community-associated Methicillin-resistant S. aureus (MRSA) strain and AH4807, a USA300 MRSA strain was tested.

Mouse model of S. aureus skin infection. Skin infection experiments were done as described previously (Nizet et al., 2001). S. aureus strain USA300 was used for infection. In brief, the backs of sex-matched and age-matched (8 week to 12 week) adult wildtype or Ella/Hyal1 mice were shaved and hair removed by chemical depilation (Nair) then injected subcutaneously with 100 μl of a mid-logarithmic growth phase of S. aureus ($2 \times 10^6$ CFU of bacteria) in PBS. Mice were sacrificed after day 3 and 8 mm skin punch biopsy comprising the center of the injection site was harvested. Infected skin surrounding the infection center (6-8 mm) void of center abscess was carefully dissected out for RNA extraction or CFU determination. Skin biopsies were homogenized in 1 ml Trizol (for RNA) or PBS (for CFU counting) with 2 mm zirconia beads in a mini-bead beater 16 (Biospect, Bartlesville, Okla.). To count CFU, homogenized skin samples were serially diluted, plated onto Tryptic Soy Agar, and enumerated after 18 hours to quantify the CFU per gram of tissue. For in vivo live bacterial imaging, mice were imaged under isoflurane inhalation anesthesia (2%). Photons emitted from luminescent bacteria were collected during a 1 min exposure using the Xenogen IVIS Imaging System and living image software (Xenogen, Alameda, Calif.). Bioluminescent image data are presented on a pseudocolor scale (blue representing least intense and red representing the most intense signal) overlaid onto a gray-scale photographic image. Using the image analysis tools in living image software, circular analysis windows (of uniform area) were overlaid onto regions of interest and the corresponding bioluminescence values (total flux) were measured.

Study approval. All animal experiments were approved by the University of California, San Diego, Institutional Animal Care and Use committee. For all animal studies, animals were randomly selected without formal pre-randomization and quantitative measurements were done without the opportunity for bias.

Chemicals and reagents. Rat anti-Cemip antibodies were provided by KAO company. Rabbit anti-CAMP antibodies were made as described previously (Dorschner et al., 2001); rabbit anti-PREF1/DLK antibodies are from Abcam (Cambridge, Mass.); BODIPY® FL dye was purchased from Thermo Fisher (Houston, Tex.). HA binding protein was purchased from Millipore., mouse-Hyal1, Hyal2, KIAA1199, TMEM2, HAS1, HAS2, HAS3, ZFP423, Pref1, PPARg, Adipoq, CEBPA, CAMP, IL6, TNF Taqman gene expression assay were purchased from Life Technologies Corporation (Grand Island, N.Y.).

Reverse transcription-quantitative PCR (RTqPCR) analyses. RTqPCR was used to determine the mRNA abundance as described previously (Morioka et al., 2008). Total cellular RNA was extracted using the PureLink RNA Mini Kit (Life Technologies Corporation, Grand Island, N.Y.) and mRNA were purified by using Dynabeads mRNA Purification Kit (Life technologies). 100 ng of mRNA was reverse transcribed to cDNA using iScript cDNA synthesis kit (Bio-Rad Laboratiries, Inc. Hercules, Calif.). Quantitative, real-time PCR was performed on the CFX96 real time system (Biorad) using predeveloped Taqman gene expression assay (Applied Biosystems). The expression of β-Actin gene was used as a house keeping gene to normalize data.

Histology and immunohistochemistry (IHC). Tissue biopsies were directly embedded in OCT compound or paraffin. Paraffin embedded tissues are used for Hematoxylin/Eosin (H&E) staining, and frozen sections were fixed in 4% PFA for 20 mins or 100% acetone prior to immunofluorescence staining. For IHC, fixed and permeabilized frozen tissue sections were blocked with Image-iT FX reagent (Invitrogen) before incubating with primary antibodies followed by appropriate 488- or 568-coupled secondary antibodies. Nuclei were counterstained with DAPI. All images were taken with an Olympus BX41 microscope (widefield) or Zeiss LSM510 confocal microscope as indicated.

Flow cytometry analyses. Colon collected from control or DSS-treated mice was cut into small pieces then digested with 2.5 mg/mL Collagenase D and 30 ng/mL DNAse1 for 2 hours at 37° C. then filtered through a 30 μm filter to generate single cell suspension for FACS analyses. Cells were then stained with zombie violet viability dye (BioLegend, 423114), blocked with anti-mouse CD16/32 (eBioscience, 14016185), followed by staining with antibody cocktails for preadipocytes or immune cells. The antibody cocktail for preadipocytes includes AF488-SMA (eBioscience, 53976082), PECy7-CD45 (BioLegend, 147704), PerCy5.5-CD31 (BioLegend, 102522), PE-Thy1 (BioLegend, 105308), APC-PDGFRa (eBioscience, 17140181), BV605-SCA1 (BioLegend, 108133) and AF700-CD24 (BioLegend, 108136). The antibody cocktail for immune cells includes PECy7-CD11b (BioLegend, 101216), FITC-Ly6G (eBioscience, 11593182), PE-F4/80 (eBioscience, 12480182), APC-CD11C (BioLegend, 117310), AF700-MHCII (eBioscience, 56532182), APC-Cy7-CD3 (BioLegend, 100222), Tbet (Fisher Scientific, 562467), GATA3 (BioLegend, 653807), RORgt (eBioscience, 12-6981-80), IFN-gamma (BioLegend, 505809), IL-17 (BioLegend, 506929), Foxp3 (eBioscience, 48-5773-80) and Fixable Viability Dye eFluor™ 506 (eBioscience, 65-0866-14) FACS analyses for surface expression of preadipocyte or immune cell markers were performed by the BD FACSCanto RUO machine and analyzed by FlowJo V10 software. Dead cells stained positive with zombie violet dye were excluded from the analyses.

Hyaluronan (HA) analysis. Glycosaminoglycan (GAGs), including HA were extracted from murine skin as previously described (Muto et al., 2014).Samples were homogenized and treated overnight with protease (0.16 mg/ml; Sigma-Aldrich) to degrade protein, followed by purification by anion exchange chromatography using DEAE Sephacel (Amersham Biosciences). Columns were washed with a low-salt buffer (0.15 M NaCl in 20 mM sodium acetate; pH 6.0) and eluted with 1 M NaCl. Glycans were desalted by PD10 (GE Healthcare). HA concentrations were measured ELISA Duo Set (R&D Systems). The size distribution of HA was analyzed by agarose gel electrophoresis (Lee and Cowman, 1994). The HA sample was mixed with TAE buffer containing 2 M sucrose and electrophoresed at 2 V/cm for 10 hours at room temperature. The gel was stained overnight under light-protective cover at room temperature in a solution containing 0.005% Stains-All in 50% ethanol, and destained in water. Hyalose ladders (Hyalose) were used for standards.

Statistics. Experiments were repeated at least three times with similar results. Statistical significance was determined using Student's unpaired two-tailed t test, or one-way ANOVA multiple comparison test as indicated in the legend ($*p<0.05$, $p<0.01$, $*p<0.001$).

Figure 36A:
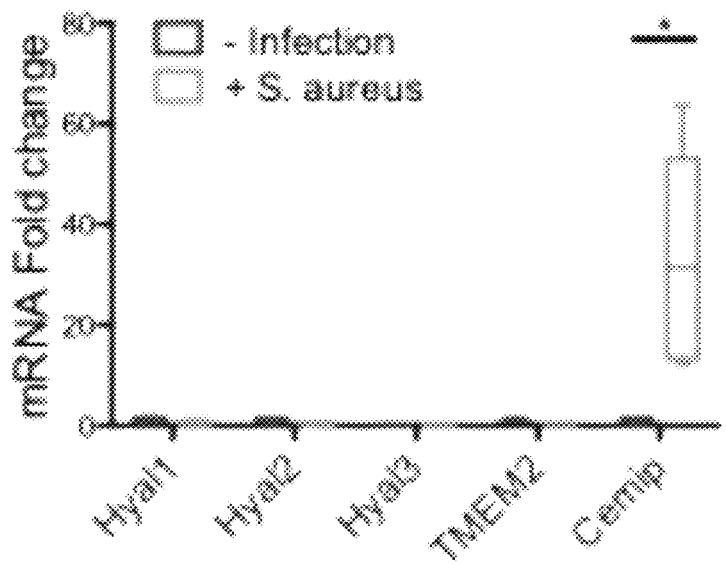
FIG. 36A-E shows Cemip is necessary for HA digestion after infection. (A) The expression of transcripts for 5 known mammalian hyaluronidases in murine skin is shown before and 3 days following infection by S. aureus. (n=4 control or 6 skin infection mice/group). (B) Mouse dermis stained for HA or Cemip or DAPI in representative sections of skin from control and Cemip$^{-/-}$ mice before and 3 days after S. aureus infection. Dotted lines outline regions of HA loss. Infection was to the upper right in all fields shown. Scale Bar=20 Microns (C) mRNA expression from skin measured by qPCR for Cemip (n=6 mice/group). (D) HA abundance measured by ELISA in skin extracts. (n=3 mice/group). (E) Gel electrophoresis and staining for HA. a: wild-type skin, b: Cemip$^{-/-}$ skin, c: wild-type skin 3 days after S. aureus, d: Cemip$^{-/-}$ 3 days after S. aureus. Arrow indicates accumulation of low molecular weight HA as only seen in control mice after S. aureus. All error bars indicate mean±SEM; *P<0.05P<0.01, *P<0.001 (t test).
Figure 36B:
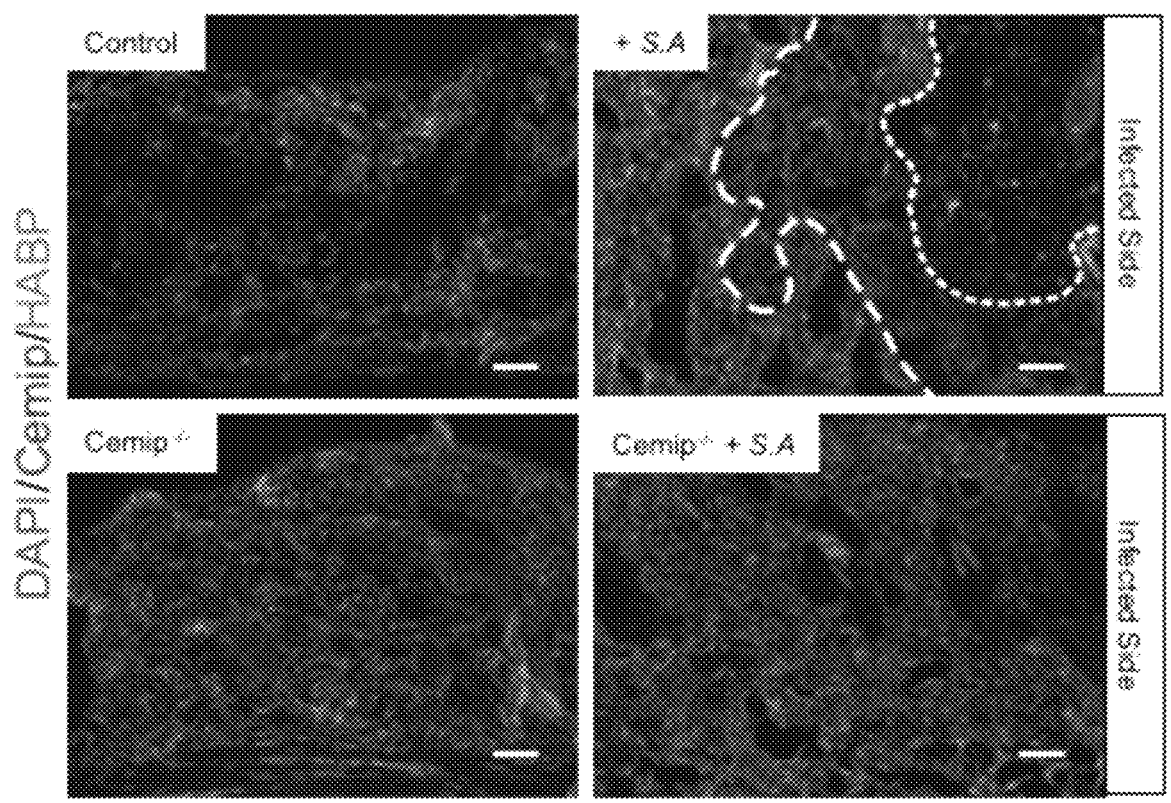
Figure 36C:
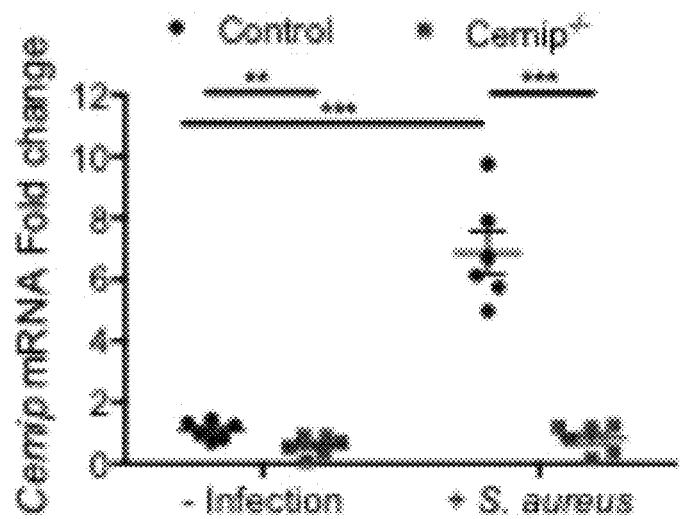
Figure 36D:
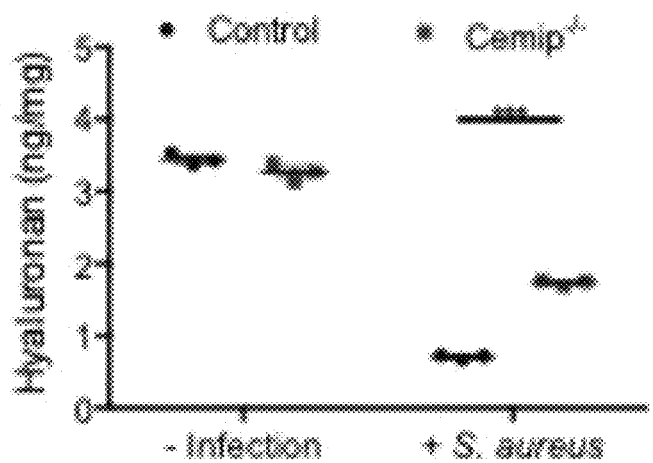
Figure 36E:
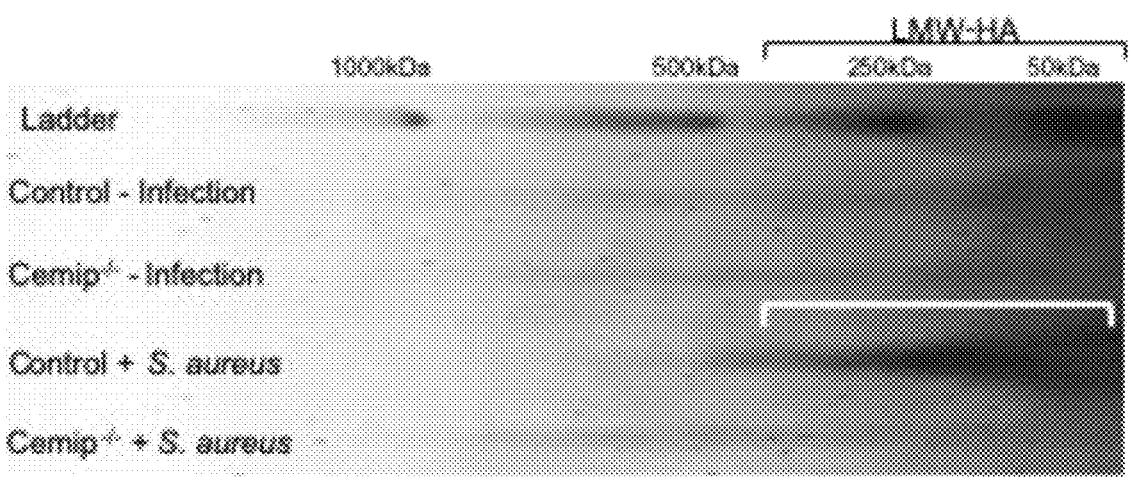
Figure 40A:
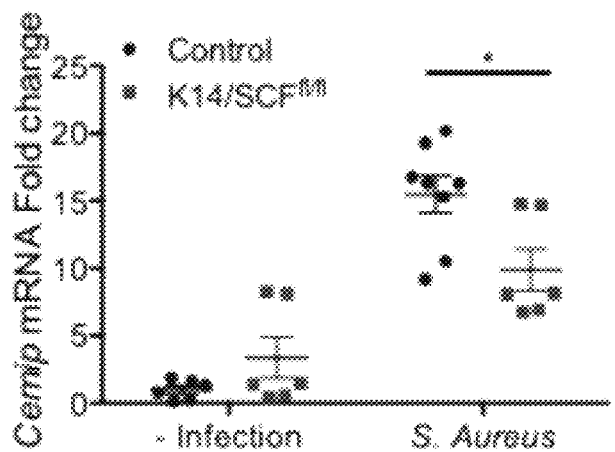
FIG. 40A-B shows Cemip expression in mast cell deficient mice. (A) mRNA expression from skin measured by qPCR of Cemip (n=6 mice/group). (B) Mouse dermis stained for Avidin (green) or Cemip (red) or DAPI (blue) in representative sections of skin from control and K14/SCF$^{fl/fl}$ mice 3 days after S. aureus infection. Dotted lines outline regions of HA loss. Scale Bar=20 Microns. All error bars indicate mean±SEM; *P<0.05, P<0.01, *P<0.001 (t test).
Figure 40B:
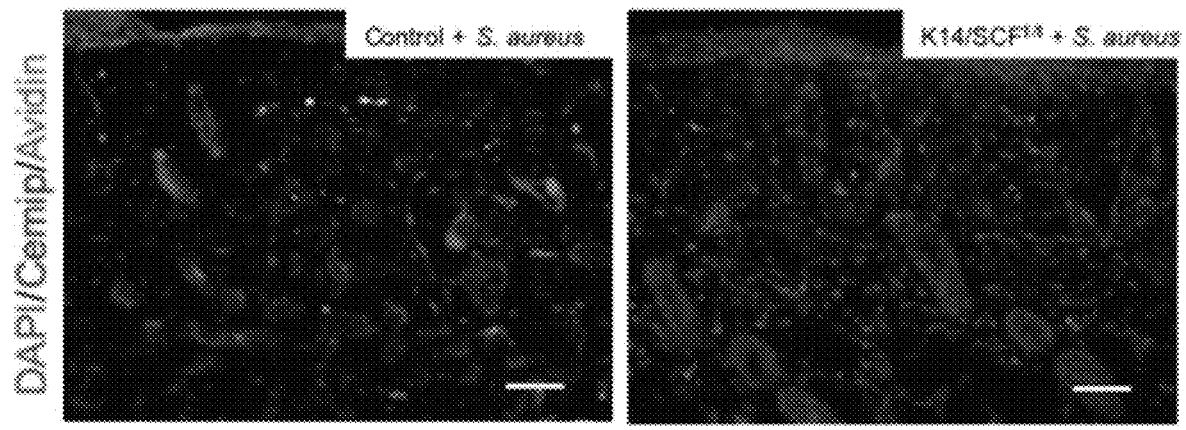
Figure 41A:
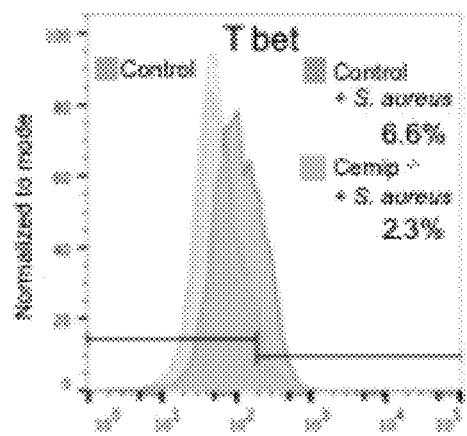
FIG. 41A-F shows loss of Cemip decreases the systemic response to S. aureus. (A to F) Flow cytometry analysis of single cell suspensions from the spleen showing expression of Tbet, GATA3, RORγt, INFγ and 1 IL-17 from control, Cemip-/-, control infection and Cemip-/- infection. Cells were gated on CD4 positive. Numbers represent the percentage of the cells in the indicated gate. (n=3) All error bars indicate mean±SEM; *P<0.05, P<0.01, *P<0.001 (t test).
Figure 41B:
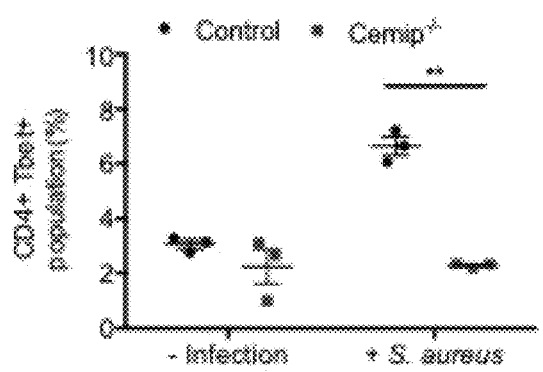
Figure 41C:
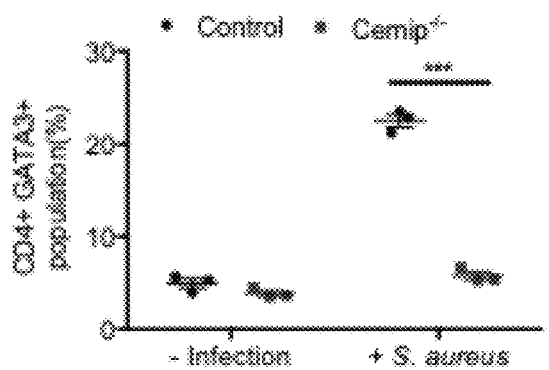
Figure 41D:
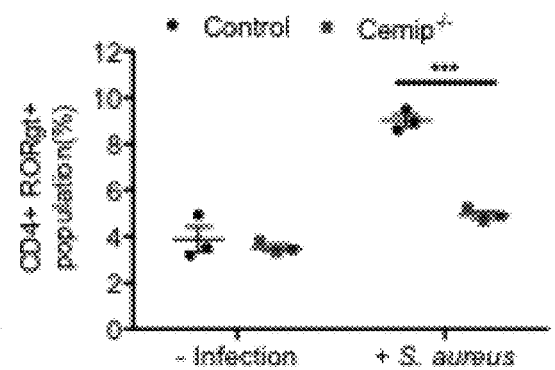
Figure 41E:
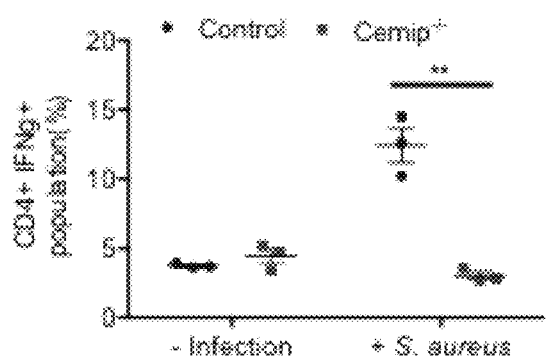
Figure 41F:
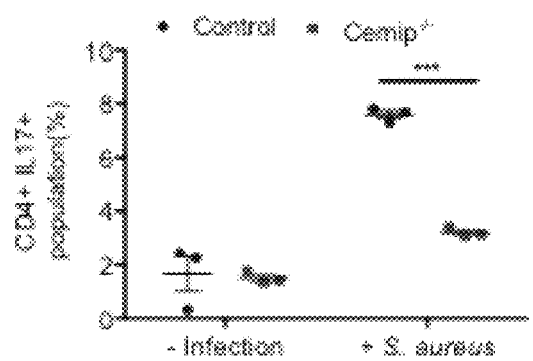

Cemip digests dermal hyaluronan during *S. aureus* skin infection. The expression of Cemip in mice was examined following inoculation of *S. aureus* into the dermis to test if this enzyme may be the hyaluronidase responsible for HA degradation during skin injury. *S. aureus* was chosen as the model skin pathogen over GAS as it does not synthesize HA itself, but does produce a secreted hyaluronidase that confers virulence (Ibberson et al., 2014). *S. aureus* infection significantly increased Cemip mRNA in whole skin, but the expression of other murine hyaluronidases (Hyal1, Hyal2, Hyal3 and transmembrane protein 2=TMEM2) were unchanged (FIG. 36A). Immunohistochemical analysis of locally infected tissue showed Cemip was increased in regions where HA staining was decreased (FIG. 36B). Cemip$^{-/-}$ mice failed to show an increase of Cemip mRNA and had a greater amount of HA in the dermis following skin infection (FIG. 36B-D). Furthermore, the decrease in size of HA that occurs following infection was abolished in Cemip$^{-/-}$ mice (lanes c and d of FIG. 36E). Mast cell deficient mice had less Cemip expression, a finding consistent with a role of histamine in the induction of Cemip (FIG. 40). These observations demonstrate that Cemip promotes digestion of HA in the skin during infection by *S. aureus*.

Figure 37A:
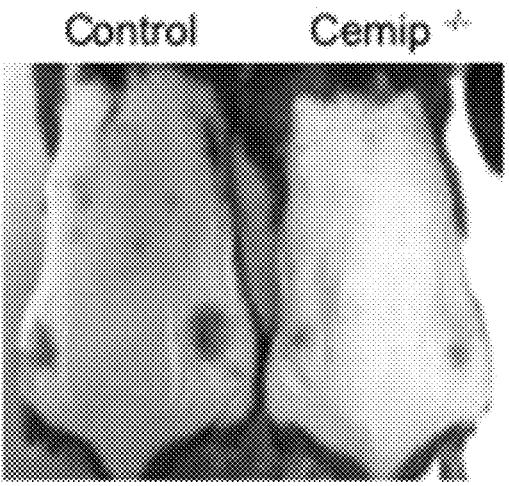
Figure 37B:
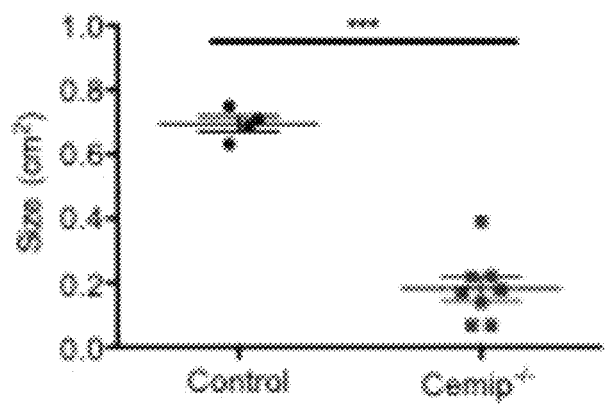
Figure 37C:
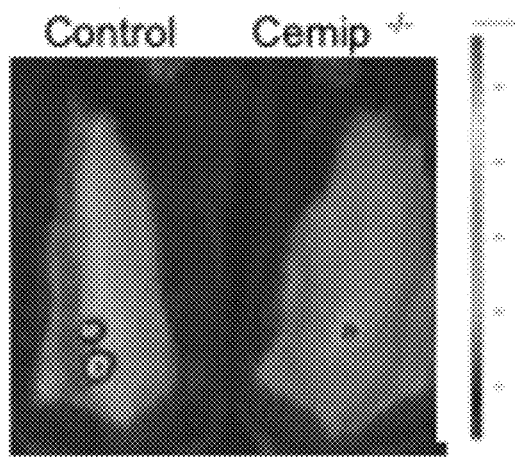
Figure 37D:
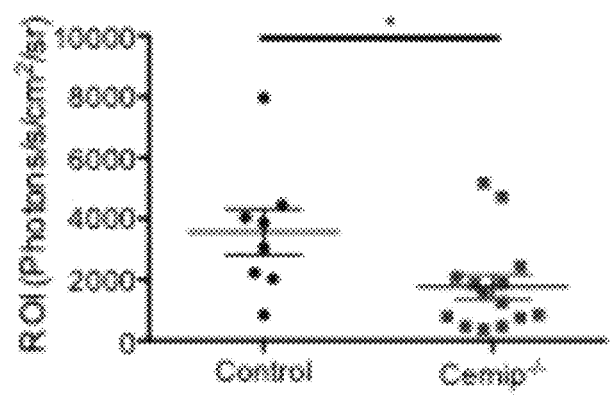
Figure 37E:
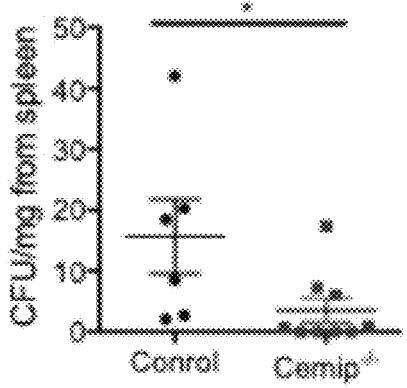
Figure 37F:
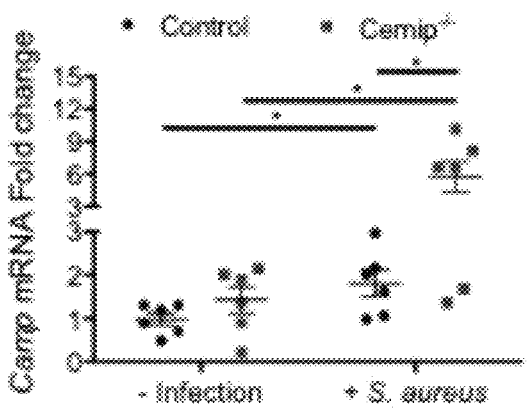
Figure 37G:
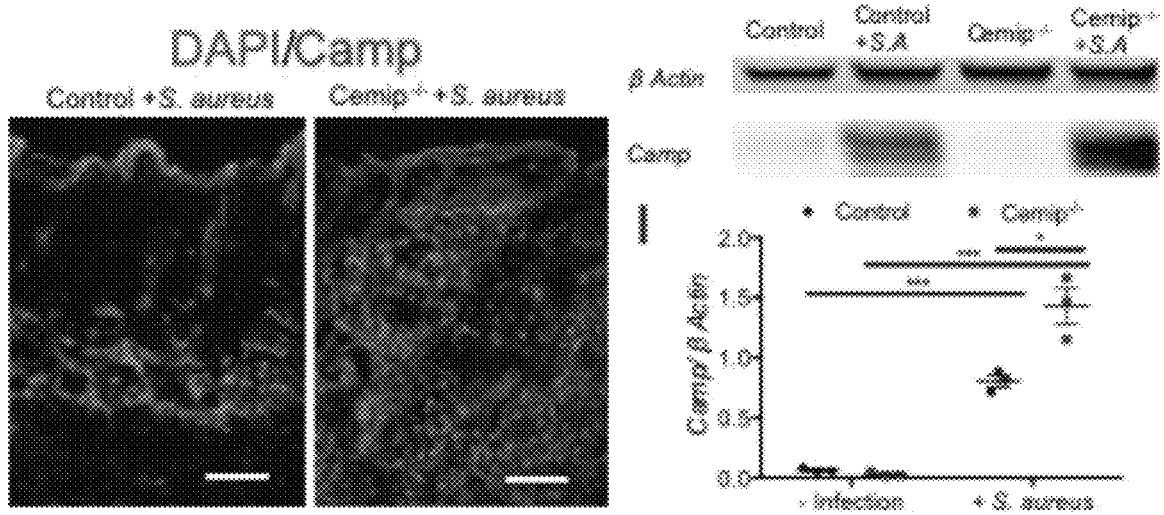

Loss of Cemip increases resistance against *S. aureus*. To evaluate the functional significance of HA digestion by Cemip, tissue injury and *S. aureus* survival was measured in the skin of Cemip$^{-/-}$ mice. Three days after *S. aureus* injection, necrotic lesions on Cemip$^{-/-}$ mice were significantly smaller (FIG. 37A, B) and less live bacteria were evident in the skin (FIG. 37C, D). A lower amount of bacteria were also detected in spleens from Cemip$^{-/-}$ mice (FIG. 37E). Since the expression of the cathelicidin antimicrobial peptide Camp is strongly associated with resistance to bacterial skin infections (Nizet et al., 2001), the relative expression of Camp in the skin of these mice was assessed. mRNA for Camp was significantly increased in tissue biopsies from the infected site of Cemip$^{-/-}$ mice (FIG. 37F) and more cathelicidin protein was observed in tissue surrounding the infected area of the dermis (FIG. 37G-I). These observations suggest that loss of Cemip function enabled increased Camp expression.

Figure 38A:
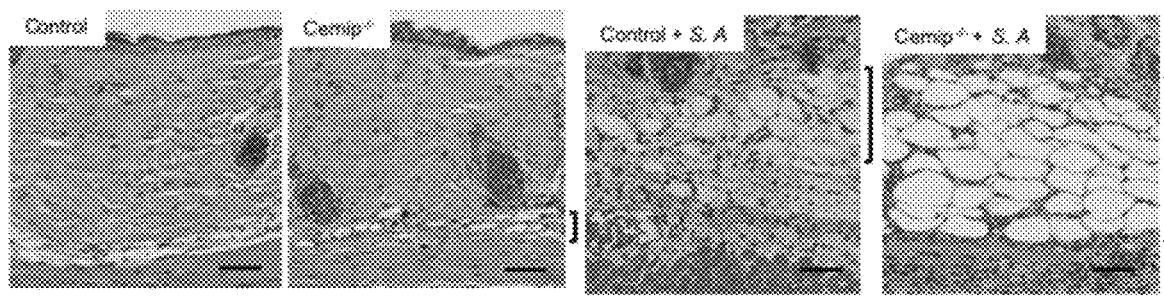
FIG. 38A-G shows loss of Cemip enhances reactive adipogenesis. (A) Representative histological images of skin from mice at day 0 and 3 days after infection with S. aureus. Tissue was stained with hematoxylin and eosin. Brackets delineate dermal region occupied by adipocytes. Scale Bar=50 Microns. (B) Quantification of the adipose tissue thickness indicated Scale Bar. (n=8 for Control and Cemip$^{-/-}$ infection mice/group). (C-E) RTqPCR of the relative abundance of transcripts for Pref1, PPARγ, Adipoq as normalized to β-actin (n=4 for normal condition n=8 for infection mice/group). (F, G) Flow cytometry analysis of single cell suspensions from the skin showing expression of PEGFRα from control, Cemip$^{-/-}$, control infection and Cemip$^{-/-}$ infection. Cells were gated on CD31-negative, CD45-negative, SCA-1 positive. Numbers represent the percentage of the cells in the indicated gate. All error bars indicate mean±SEM; * P<0.05, P<0.01, *P<0.001 (t test).
Figure 38B:
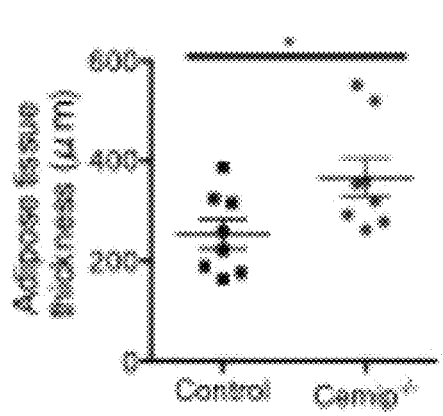
Figure 38C:
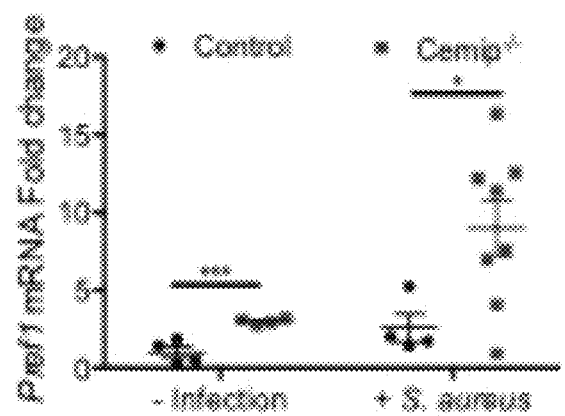
Figure 38D:
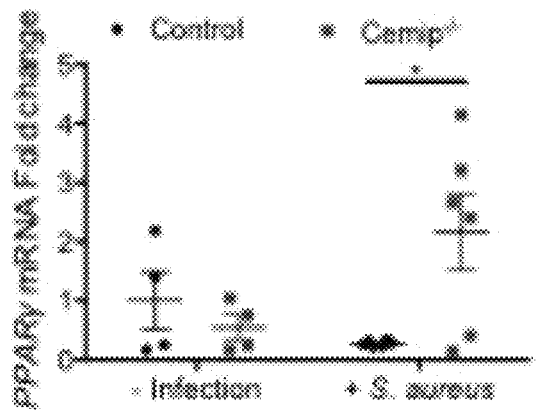
Figure 38E:
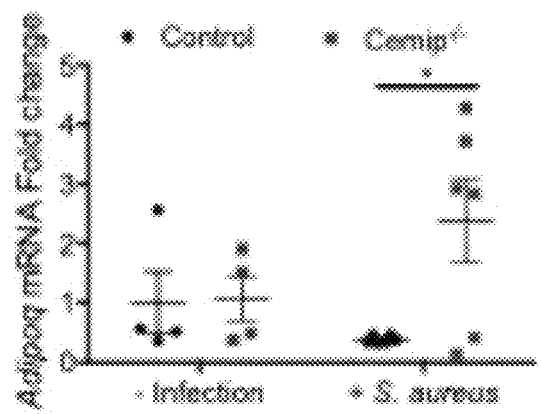
Figure 38F:
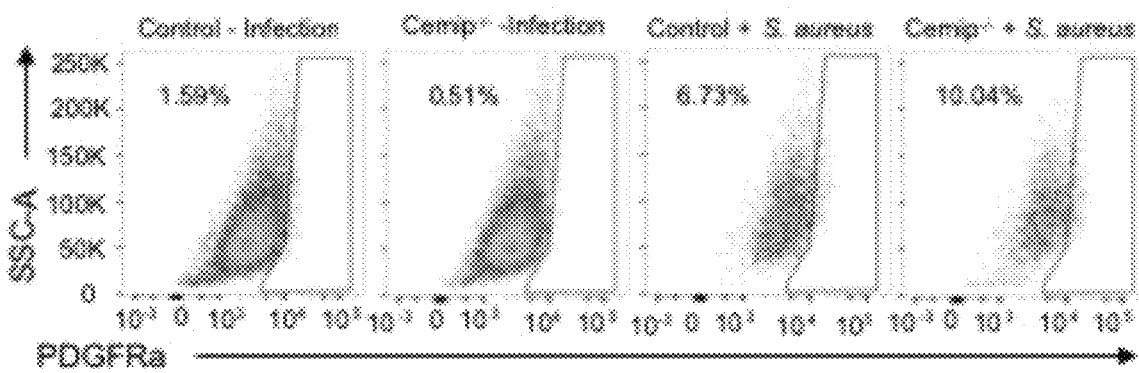
Figure 38G:
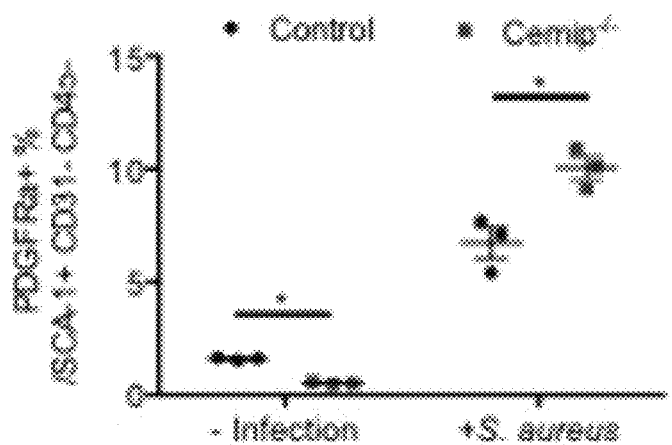

Loss of Cemip enhances reactive adipogenesis. A major source of cathelicidin expression in the skin comes from the local differentiation of preadipocyte fibroblasts into adipocytes, a process referred to as reactive adipogenesis (Zhang et al., 2015). Degradation of HA inhibits the capacity of preadipocytes to differentiate into mature adipocytes (Dokoshi et al., 2018; Ji et al., 2014). Therefore, it was hypothesized that the digestion of HA by Cemip may inhibit the local adipogenic response and thus suppress the expression of the antimicrobial peptide by these cells. Histological evaluation of the deep dermis showed a greater expansion of subcutaneous white adipose tissue (DWAT) after infection in Cemip$^{-/-}$ mice (FIG. 38A, B). Consistent with the observation of enhanced reactive adipogenesis by decreasing hyaluronidase activity, there was also significantly increased expression of genes associated with adipogenesis in Cemip$^{-/-}$ mice (Preadipocyte factor 1 (Pref-1), Peroxisome Proliferator Activated Receptor Gamma (PPARg) and Adiponectin) (FIG. 38C-E). FACS analysis of skin before and after *S. aureus* infection also showed an increase in the population of preadipocytes in the dermis of Cemip$^{-/-}$ mice as defined by CD31-negative, CD45-negative, Platelet-derived growth factor receptor-$\alpha$(PDGFR$\alpha$) positive and Spinocerebellar ataxia type 1 (SCA1) positive cells (FIG. 38F, G). Taken together, these data show that loss of Cemip results in an increase in dermal reactive adipogenesis.

Figure 39A:
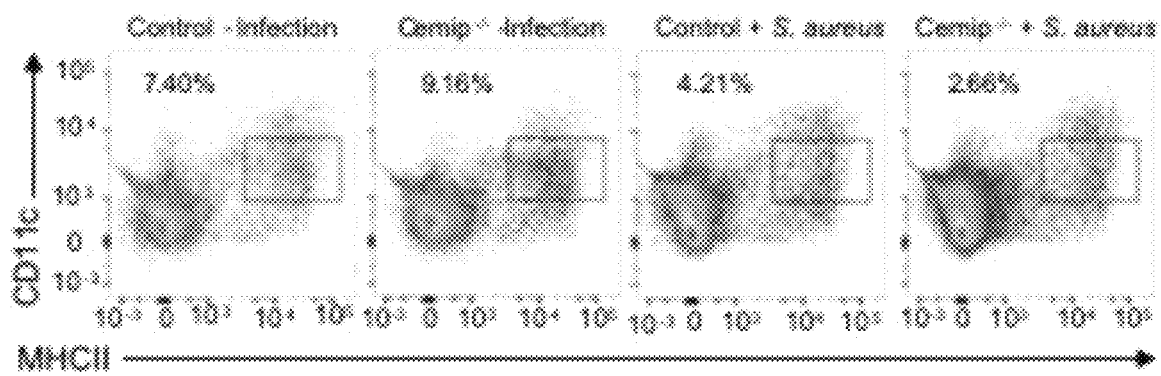
FIG. 39A-H shows loss of Cemip enhances local skin inflammation in response to S. aureus. (A to F) Flow cytometry analysis of single cell suspensions from the skin showing expression of CD11c/MHCII, Ly6G/CD11b, and LyG-C cells isolated from control, Cemip$^{-/-}$, control infection and Cemip$^{-/-}$ infection. Cells were gated on CD3-negative. Numbers represent the percentage of the cells in the indicated gate. (G) Representative sections of skin from control and Cemip$^{-/-}$ mice at 3 days after S. aureus infection. Tissues are stained with red with Gr-1 antibody and blue with DAPI. Scale Bar=20 Microns. (H) RTqPCR of the relative abundance of transcripts for IL-6 as normalized to β-actin (n=4 for normal condition n=8 for infection mice/group). All error bars indicate mean±SEM; *P<0.05, P<0.01, *P<0.001 (t test).
Figure 39B:
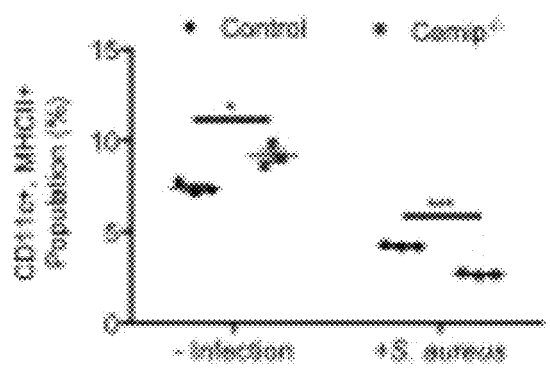
Figure 39C:
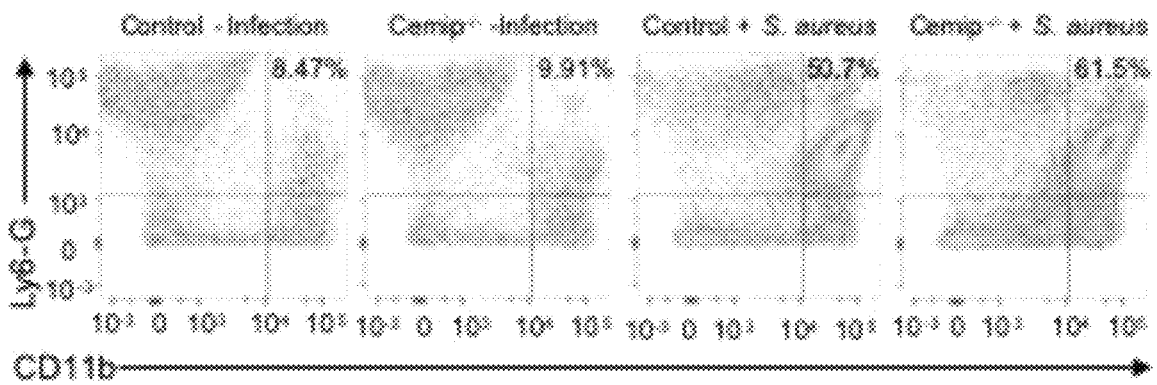
Figure 39D:
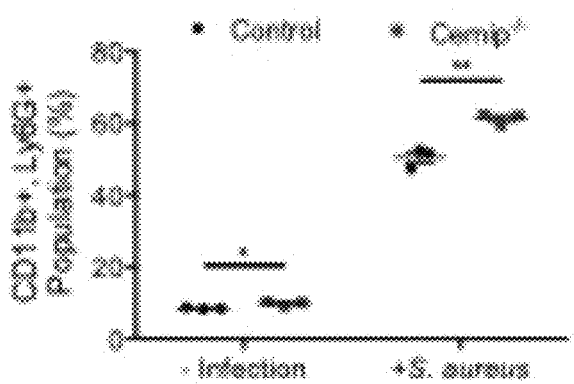
Figure 39E:
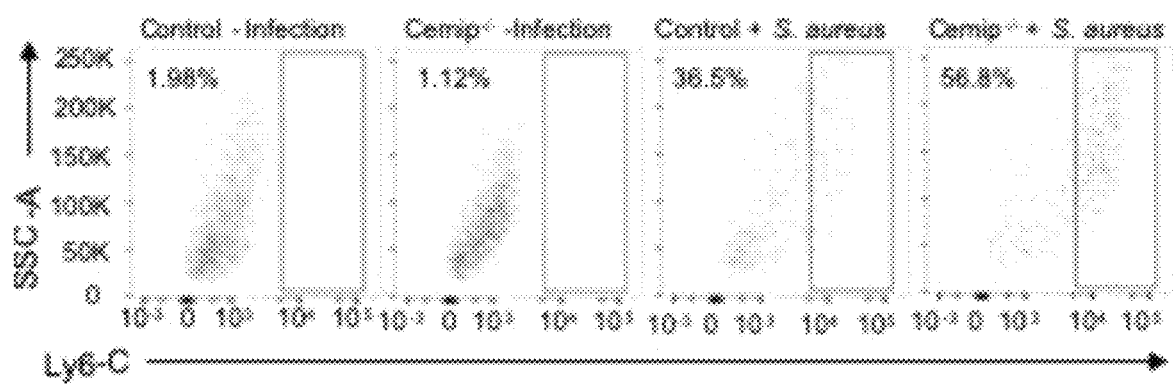
Figure 39F:
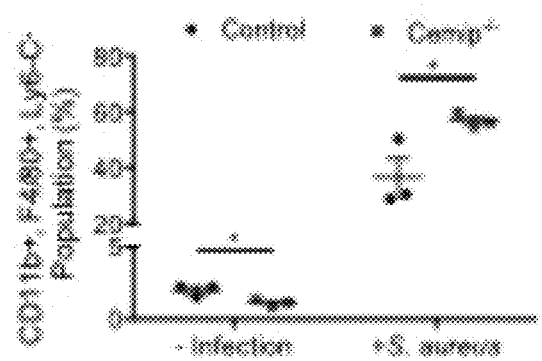
Figure 39G:
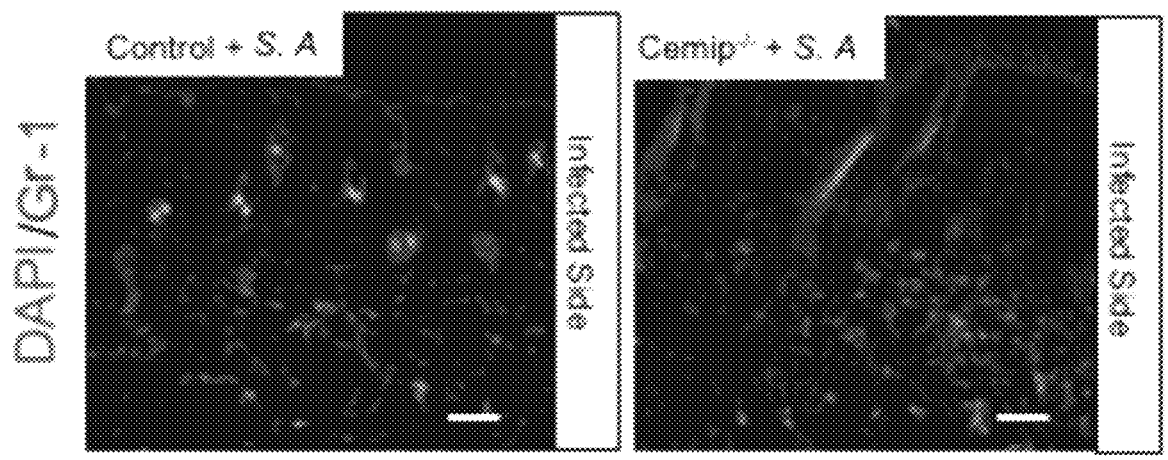
Figure 39H:
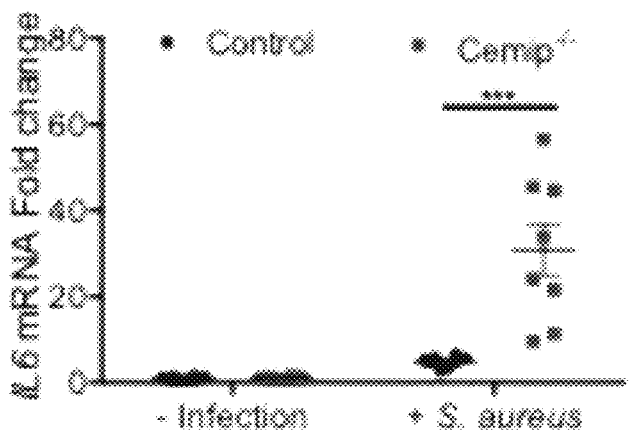

Loss of Cemip enhances the inflammatory response to infection. The expression of Camp and other products of reactive adipogenesis can influence inflammation that may amplify the host defense against *S. aureus* (Hancock et al., 2016; Zhang et al., 2016). Therefore, this was also investigated to determine the influence of Cemip on resident and circulating lymphoid populations. FACS analysis of resident skin lymphoid cells revealed that Cemip$^{-/-}$ mice had differences in the relative abundance of CD11c dendritic cells, LY6-G neutrophils and F4/80 /Ly6-C monocytes (FIG. 39A-F). Interestingly, under baseline conditions, dendritic cells and neutrophils were both slightly elevated in Cemip$^{-/-}$ mice. Following infection, Cemip$^{-/-}$ mice had relatively lower amounts of dendritic cells and higher numbers of the CD11b, LY6-G and F4/80/Ly6C positive populations. Neutrophils are a critical cell type for resistance to *S. aureus* infection, and increased numbers of LY6G positive neutrophils was evident by immunohistochemistry (FIG. 39G), and an increase in IL-6 mRNA as measured by qPCR (FIG. 39H) was detected in the skin of *S. aureus* infected Cemip$^{-/-}$ mice. The systemic responses in Cemip$^{-/-}$ mice infected by *S. aureus* was also examined. Cemip$^{-/-}$ mice showed significantly lower fractions of T-box transcription factor (Tbet)+, Retinoid-Related Orphan Receptor Gamma T (RORgt)+, Interferon Gamma (IFNg)+ and IL-17+ T cells in the spleen (FIG. 41A to F). Overall, the loss of Cemip expression resulted in an enhanced local inflammatory response and decreased systemic inflammatory response after *S. aureus* infection.

A number of embodiments of the invention have been described. Nevertheless, it will be understood that various modifications may be made without departing from the spirit and scope of the invention. Accordingly, other embodiments are within the scope of the following claims.

What is claimed is:

1. A composition comprising therapeutically effective amounts of substantially purified oligosaccharide fragments of hyaluronan (OligoHA) and/or therapeutically effective amounts of a substantially purified enzyme that degrades hyaluronan into oligosaccharide fragments, wherein the composition comprises 60% or more by weight of a combination of tri-, tetra- and hexa-saccharide fragments of hyaluronan.

2. The composition of claim 1, wherein the composition comprises 80% or more by weight or by composition of a combination of tri-, tetra-, and hexa-saccharide fragments of hyaluronan.

3. The composition of claim 1, wherein the composition is formulated for topical or oral administration to a subject in need thereof.

4. The composition of claim 1, wherein the composition comprises OligoHA and an enzyme that degrades hyaluronan into oligosaccharide fragments, wherein the enzyme is selected from the group consisting of: a hyaluronidase derived from humans, a hyaluronidase derived from Streptomyces, a hyaluronidase SD, a chondroitinase ACI, a chondroitinase ACIII, a chondroitinase ABC and an endoglucuronidase derived from leeches.

5. A method to reduce or inhibit inflammation in a subject in need of treatment thereof, comprising:
administering a therapeutically effective amount of the composition of claim 1 to the subject.

6. The method of claim 5, wherein the inflammation is associated with an inflammatory disease or disorder, or associated with a bacterial infection.

7. The method of claim 6, wherein the inflammatory disease or disorder is selected from the group consisting of ulcerative colitis, inflammatory bowel disease, Crohn's disease, dermatitis, psoriasis, sinusitis, active hepatitis, asthma, rheumatoid arthritis, osteoarthritis, vasculitis, lupus, and fibromyalgia.

8. A method to reduce or inhibit adipogenesis and/or adipocyte differentiation in a subject in need of treatment thereof, comprising:
administering a therapeutically effective amount of the composition of claim 1 to the subject.

9. The method of claim 8, wherein the composition is topically administered to reduce or inhibit adipogenesis and/or adipocyte differentiation in dermal and/or hypodermal tissue.

10. The method of claim 8, wherein the composition is orally administered to reduce or inhibit adipogenesis and/or adipocyte differentiation in the gastrointestinal track.

11. The method of claim 10, wherein the adipogenesis and/or adipocyte differentiation in the gastrointestinal track is associated with an inflammatory gastrointestinal disorder or disease.

12. A method to promote sensitization to an antigen/allergen in a subject, comprising:
administering a therapeutically effective amount of the composition of claim 1 to the subject; and
delivering an antigen/allergen to the subject.

13. The method of claim 12, wherein the composition is administered prior to, simultaneously with, or immediately after delivering the antigen/allergen to the subject.

14. The method of claim 12, wherein administration of the composition prior to the delivering the antigen/allergen induces anergy in the subject.

15. The method of claim 13, wherein the composition is administered within 1 minute to 30 minutes of the delivery of the antigen/allergen to the subject.

16. The method of claim 12, wherein administration of the composition induces dendritic cell maturation and/or migration.

* * * * *

SEQUENCE LISTING

<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: pcDNA3.1 BGH polyadenylation forward primer

```
<400> SEQUENCE: 1
gtggtctaga gctcggtacc aagc                                              24

<210> SEQ ID NO 2
<211> LENGTH: 35
<212> TYPE: DNA
<213> ORGANISM: Artificial Sequence
<220> FEATURE:
<223> OTHER INFORMATION: pcDNA3.1 BGH polyadenylation reverse primer

<400> SEQUENCE: 2
ccctctagag ccagatctgg ttctttccgc ctcag                                  35
```